(12) United States Patent
Tacha et al.

(10) Patent No.: US 9,428,576 B2
(45) Date of Patent: Aug. 30, 2016

(54) ANTI-P40 ANTIBODIES SYSTEMS AND METHODS

(71) Applicant: Biocare Medical LLC, Concord, CA (US)

(72) Inventors: David Tacha, San Ramon, CA (US); Weimin Qi, Martinez, CA (US)

(73) Assignee: Biocare Medical, LLC, Concord, CA (US)

( * ) Notice: Subject to any disclaimer, the term of this patent is extended or adjusted under 35 U.S.C. 154(b) by 0 days.

(21) Appl. No.: 14/839,744

(22) Filed: Aug. 28, 2015

(65) Prior Publication Data

US 2016/0009795 A1    Jan. 14, 2016

Related U.S. Application Data

(63) Continuation of application No. PCT/US2014/019705, filed on Feb. 28, 2014.

(60) Provisional application No. 61/770,956, filed on Feb. 28, 2013.

(51) Int. Cl.
| | |
|---|---|
| *C07K 16/30* | (2006.01) |
| *C07K 16/18* | (2006.01) |
| *G01N 33/574* | (2006.01) |
| *G01N 33/50* | (2006.01) |
| *C07K 16/28* | (2006.01) |
| *G01N 33/577* | (2006.01) |

(52) U.S. Cl.
CPC ............... *C07K 16/18* (2013.01); *C07K 16/28* (2013.01); *G01N 33/5017* (2013.01); *G01N 33/574* (2013.01); *G01N 33/577* (2013.01); *G01N 33/57484* (2013.01); *G01N 33/57488* (2013.01); *C07K 2317/34* (2013.01)

(58) Field of Classification Search
CPC  C07K 14/47; C07K 14/705; C07K 14/4727; C07K 16/28; C07K 2317/34; C07K 16/18; C07K 16/30; C07K 2317/56; C07K 2319/01; C07K 2319/10; C07K 14/65; C07K 16/1232; G01N 2333/705; G01N 33/574
See application file for complete search history.

(56) References Cited

U.S. PATENT DOCUMENTS

| | | |
|---|---|---|
| 4,145,406 A | 3/1979 | Schick et al. |
| 4,254,082 A | 3/1981 | Schick et al. |
| 4,687,732 A | 8/1987 | Ward et al. |
| 4,690,890 A | 9/1987 | Loor et al. |
| 4,792,521 A | 12/1988 | Shochat |
| 4,863,875 A | 9/1989 | Bailey et al. |
| 5,089,423 A | 2/1992 | Diamandis et al. |
| 5,108,896 A | 4/1992 | Philo et al. |
| 5,252,487 A | 10/1993 | Bacus et al. |
| 5,482,698 A | 1/1996 | Griffiths |
| 5,487,975 A | 1/1996 | Miller et al. |
| 5,565,332 A | 10/1996 | Hoogenboom et al. |
| 5,620,845 A | 4/1997 | Gould et al. |
| 5,691,154 A | 11/1997 | Callstrom et al. |
| 5,719,063 A | 2/1998 | Block |
| 5,869,274 A | 2/1999 | Tsao et al. |
| 5,891,658 A | 4/1999 | Klainer et al. |
| 6,008,057 A | 12/1999 | Glass et al. |
| 6,051,693 A | 4/2000 | Handley et al. |
| 6,252,053 B1 | 6/2001 | Ohbayashi et al. |
| 6,403,769 B1 | 6/2002 | Larochelle et al. |
| 6,409,990 B1 | 6/2002 | Vera |
| 6,476,206 B1 | 11/2002 | Sidransky et al. |
| 6,537,745 B2 | 3/2003 | Chien et al. |
| 6,580,056 B1 | 6/2003 | Tacha |
| 6,723,506 B2 | 4/2004 | Fletcher et al. |
| 6,946,256 B1 | 9/2005 | McKeon et al. |
| 7,422,739 B2 | 9/2008 | Anderson et al. |
| 7,468,425 B2 | 12/2008 | Sidransky et al. |
| 7,674,605 B2 | 3/2010 | Lin et al. |
| 7,785,803 B2 | 8/2010 | Achen et al. |
| 7,846,726 B2 | 12/2010 | Li et al. |
| 7,846,762 B2 | 12/2010 | Rana et al. |
| 7,875,705 B2 | 1/2011 | Iwaneri et al. |
| 7,935,794 B2 | 5/2011 | Pullen |
| 7,935,795 B2 | 5/2011 | Nakajima |
| 7,935,796 B2 | 5/2011 | Lee et al. |
| 7,973,138 B2 | 7/2011 | Liang et al. |
| 8,153,126 B2 | 4/2012 | Violette et al. |
| 8,168,409 B2 | 5/2012 | Calzone et al. |
| 8,338,576 B2 | 12/2012 | Paralkar et al. |
| 8,603,765 B2 | 12/2013 | Tacha |
| 8,852,592 B2 | 10/2014 | Qi et al. |
| 9,005,612 B2 | 4/2015 | Ledbetter et al. |

(Continued)

FOREIGN PATENT DOCUMENTS

| | | |
|---|---|---|
| EP | 2402370 A1 | 1/2012 |
| WO | 2005076005 A2 | 8/2005 |
| WO | 2005083802 A1 | 9/2005 |
| WO | 2010124689 A1 | 11/2010 |
| WO | 2012154983 | 11/2012 |
| WO | 2012154983 A3 | 11/2012 |
| WO | 2014052672 A1 | 4/2014 |
| WO | 2014100220 A2 | 6/2014 |
| WO | 2014134587 A1 | 9/2014 |

OTHER PUBLICATIONS

Tacha et al. 'A 6-Anitbody Panel for the Classification of Lung Adenocarcinoma Versus Squamous Cell Carcinoma.' Appl Immunohistochem Mol Morphol. 20(3): 201-7, May 2012.

Brown, et al. 'Tissue Preserving Antibody Cocktails to Differentiate Primary Squamous Cell Carcinoma, Adenocarcinoma, and Small Cell Carcinoma of Lung.' Arch Pathol Lab Med. 137(9):1274-81. Jan. 4, 2013.

(Continued)

*Primary Examiner* — Shafiqul Haq
*Assistant Examiner* — Carmencita M Belei
(74) *Attorney, Agent, or Firm* — Santangelo Law Offices, P.C.

(57) ABSTRACT

The present invention is related to the anti-p40 antibodies, kits, cocktails, and use of anti-p40 antibodies for detection of cancer.

13 Claims, 36 Drawing Sheets

(56) References Cited

U.S. PATENT DOCUMENTS

| | | | |
|---|---|---|---|
| 9,156,915 | B2 | 10/2015 | Waldman et al. |
| 2002/0106685 | A1 | 8/2002 | Henning et al. |
| 2002/0173053 | A1 | 11/2002 | Damaj et al. |
| 2003/0017491 | A1 | 1/2003 | Shi et al. |
| 2005/0186642 | A1 | 8/2005 | Tacha |
| 2006/0148063 | A1 | 7/2006 | Fauzzi et al. |
| 2007/0015908 | A1 | 1/2007 | Fischer et al. |
| 2007/0041972 | A1 | 2/2007 | Rother et al. |
| 2009/0191190 | A1 | 7/2009 | Barghorn et al. |
| 2010/0047825 | A1 | 2/2010 | Tacha |
| 2010/0092457 | A1 | 4/2010 | Aburatani et al. |
| 2012/0082999 | A1 | 4/2012 | Liao et al. |
| 2012/0245051 | A1 | 9/2012 | Rimm et al. |
| 2012/0321557 | A1 | 12/2012 | Kimura |
| 2014/0004542 | A1 | 1/2014 | Qi et al. |
| 2014/0057803 | A1 | 2/2014 | Tacha |
| 2015/0056635 | A1 | 2/2015 | Qi et al. |
| 2015/0152180 | A1 | 6/2015 | Davis et al. |

OTHER PUBLICATIONS

Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162.

Savci-Heijink C. D., et al. The role of desmoglein-3 in the diagnosis of squamous cell carcinoma of the lung. Am J Pathol. 2009;174(5): 1629-1637.

Ring B. Z., et al. A novel five-antibody immunohisto-chemical test for subclassification of lung carcinoma. Mod Pathol. 2009;22(8): 1032-1043.

Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 5/6. Am J Surg Pathol, 2011; 35(1): 15-25.

Bishop J. A., 'p40 (ΔNp63) is superior to p63 for the diagnosis of pulmonary squamous cell carcinoma, Modern Pathology (2011), 1-11; republished Mar. 2012;25(3):405-15.

Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. Feb. 2, 2006;6:31.

Chopra, N. et al. 'Inducing Protectice Antibodies Against Ring-Infected Erythrocyte Surface Peptide Antigen of Plasmodium Falciparum Using Immunostimulating Complex (Iscoms) Delivery.' Med Microbiol. Immunol. Nov. 2000 vol. 189, No. 2: pp. 75-83.

Calbiochem-Novabiochem International. P40(Ab-1) Cat# PC373 [datasheet]. USA 2000; 2 pages.

Abcam. Understanding Secondary Antibodies: Fragment Antigen Binding Antibodies and Isotopes. USA 2012; 12 pages.

Yamaguchi, K. et al. Circulating Antibodies to P40AIS in the Sera of Respiratory Tract Cancer Patients. Int. J. Cancer. Nov. 20, 2000. vol. 89 No. 6; 5 pages.

Vaidyanathan, P. Aperio-Definins Digital Pathology Solutions [Presentation]. Jul. 7, 2011. Aperio Webinar. <http://www.aperio.com/sites/default/files/events/070611_Spectrum_Plus_ppt_for_webinar_on_integration.pd>; 10 pages.

Jain, et al. Atypical ductal hyperplasia: interobserver and intraobserver variability. Mod. Pathol. (2011) 24, 917-923.

Tacha, et al. "An Immunohitochemical Analysis of a Newly Developed Mouse Monocloncal p40 (BC28) in Lung, Bladder, Skin, Breast, Prostate, and Head and Neck Cancers" 2014 College of American Pathologists, Early Online Release, Arch Pathol. Lab Med. 8 pages, postes Feb. 2014.

Barbareschi, et al. 'p63, a p53 homologue, is a selective nuclear marker of myoepithelial cells of the human breast. Am J Surg. Pathol 25(8): 1054-1060, Aug. 2001.

Di Como, et al. 'p63 Expression Profiles in Human Normal and Tumor Tissues'. Clinical Cancer Research. vol. 8, 494-501.

Hibi, et al. 'AIS is an oncogene amplified in squamous cell carcinoma'. Pro Natl Acad Sci U.S.A, May 9, 2000, vol. 97, No. 10, 5462-5467. Feb. 2002.

Kaghdad, et al. Monoallelically Expressed Gene Related to p53 a 1p36, a Region Frequently Deleted in Neuroblastoma and Other Human Cancers. Cell, vol. 90(4), 809-819, Aug. 22, 1997.

Karni-Schmidt, et al. Distinct Expression Profiles of p63 Variants during Urothelial Development and Bladder Cancer Progression. Am J Pathol vol. 178, No. 3, Mar. 2011, 1350-60.

Khoury, et al. "p53 Isoforms: An Intracellular Microprocessor?" Genes & Cancer, 2(4), 2011, 453-465.

Murray-Zmijewski, et al. p53/p63/p73 isoforms: an orchestra of isoforms to harmonise cell differentiation and response to stress. Cell Death and Differentiation (Jun. 2006); 13(6), 962-972.

Nobre, et al. 'p40: A p63 isoform useful for lung cancer diagnosis—a Review of the Physiological and Pathological Role of p63'. Acta Cytologica 2012; 57(1):1-8.

Nonaka, 'A study of Np63 expression in lung non-small cell carcinomas'. Am J Surg Pathol vol. 36 No. 6 Jun. 2012 895-9.

Nylander, et al. 'Differential expression of p63 isoforms in normal tissues and neoplastic cells'. J Pathol 2002; 198: 417-427.

Osada, et al. Cloning and functional analysis of human p51, which structurally and functinoally resembles p53, Nat Med. Jul. 1998; 4(7): 839-43.

Pelosi, et al. 'Np63 (p40) and Thyroid Transcription Factor-1 Immunoreactivity on small biopsies or cellblocks for typing non-small cell lung cancer'. Journal and Thoracic Oncology, vol. 7(2), No. 2, Feb. 2012, 281-90.

Senoo et al. 'A second p53-Related Protein, p73L, with High Homology to p73'. Biophys Res Commun. Jul. 30, 1998; 248(3), 603-607.

Trink, et al. A new human p53 homologue, Nat Med. Jul. 1998; 4(7): 747-8.

Signoretti, Sabina 'p63 is a prostate basal cell marker and is required for prostate development'. Am J Pathol, vol. 157, No. 6, Dec. 2000, 1769-75.

Yang, et al. 'p63, a p53 homolog at 3q27-29, encodes multiple products with transactivating, death-inducing, and dominant-negative activities'. Molecular Cell, vol. 2(3), 305-316, Sep. 1998.

Bowen, et al. 'Emerging roles for PAX8 in ovarian cancer and endosalpingeal development.' Gynecologic Oncology, vol. 104, No. 2, Feb. 2007, 331-337.

Kobel M. et al. Ovarian carcinoma subtypes are different diseases: Implications for biomarker studies. PLoS Med. Dec. 2, 2008; 5(12): e232.

Nonaka D. et al. Expression of PAX8 as useful marker in distinguishing ovarian carcinomas from mammary carcinomas. Am J Surg Pathol. Oct. 2008; 32(10):1566-71.

Tong G. X. et al. Expression of PAX8 in nephrogenic adenoma and clear cell adenocarcinoma of the lower urinary tract: evidence of related histogenesis? Am J Surg Pathol. Sep. 2008; 32(9):1380-7.

Tong G. X. et al. Expression of PAX8 in normal and neoplastic renal tissues: an immunohistochemical study. Mod. Pathol. Sep. 2009; 22 (9):1218-27.

Mazal P. R. et al. Expression of aquaporins and PAX-2 compared to CD10 and cytokeratin 7 in renal neoplasms: a tissue microarray study. Mod. Pathol. Apr. 2005; 18(4):535-40.

Avery A. K. et al. Use of antibodies to RCC and CD10 in the differential diagnosis of renal neoplasms. Am J Surg Pathol. Feb. 2000; 24(2):203-10.

Zhou M. et al. The usefulness of immunohistochemical markers in the differential diagnosis of renal neoplasms. Clin Lab Med. Jun. 2005; 25(2):247.

Kuehn A. et al. Expression analysis of kidney-specific cadherin in a wide spectrum of traditional and newly recognized renal epithelial neoplasms: diagnostic and histogenetic implications. Am J Surg Pathol. Oct. 2007; 31(10):1528-33.

Mazal P. R. et al. Expression of kidney-specific cadherin distinguishes chromophobe renal cell carcinoma from renal oncocytoma. Hum Pathol. Jan. 2005; 36(1):22-8.

(56) References Cited

OTHER PUBLICATIONS

Zhu W. et al. WT1, monoclonal CEA, TTF1, and CA125 antibodies in the differential diagnosis of lung, breast, and ovarian adenocarcinomas in serous effusions. Diag Cytopathol. Jun. 2007; 35(6):370-5.
Tornos C. et al. Expression of WT1, CA 125, and GCDFP-15 as useful markers in the differential diagnosis of primary ovarian carcinomas versus metastatic breast cancer to the ovary. Am J Surg Pathol. Nov. 2005; 29(11):1482-9.
Lee A. H. et al. The expression of Wilms' tumour-1 and CA125 in invasive micropapillary carcinoma of the breast. Histopathology. Dec. 2007; 51(6):824-8.
Reid-Nicholson M. et al. Immunophenotypic diversity of endometrial adenocarcinomas: implications for differential diagnosis. Mod Pathol. Aug. 2006; 19(8):1091-100.
Zhang P. et al. Immunohistochemical analysis of thyroid-specific transcription factors in thyroid tumors. Pathol Int 2006;56:240-245.
Ozcan A. et al. PAX 8 expression in non-neoplastic tissues, primary tumors, and metastatic tumors: a comprehensive immunohistochemical study. Mod Pathol 2011;24:751-764.
Laury A.R. et al. A comprehensive analysis of PAX8 expression in human epithelial tumors. Am J Surg Pathol 2011;35:816-826.
Moretti L. et al. N-terminal PAX8 polyclonal antibody shows cross-reactivity with N-terminal region of PAX5 and is responsible for reports of PAX8 positivity in malignant lymphomas. Mod Pathol 2011.
Long K. B. et al. PAX8 Expression in well-differentiated pancreatic endocrine tumors: correlation with clinicopathologic features and comparison with gastrointestinal and pulmonary carcinoid tumors. Am J Surg Pathol 2010;34:723-729.
Baty et al. 'Gene profiling of Icinical routine biopsies and prefiction of survival in non-small cell lung cancer.' Am J Respir Crit Care Med. 181(2):181-8.Oct. 15, 2009.
Haynes C. M. et al. PAX8 is expressed in pancreatic well-differentiated neuroendocrine tumors and in extrapancreatic poorly differentiated neuroendocrine carcinomas in fine-needle aspiration biopsy specimens. Cancer Cytopathol 2011;119:193-201.
Sangoi A. R. et al. PAX8 expression reliably distinguishes pancreatic well-differentiated neuroendocrine tumors from ileal and pulmonary well-differentiated neuroendocrine tumors and pancreatic acinar cell carcinoma. Mod Pathol 2011;24:412-424.
Lorenzo P.I. et al. Immunohistochemical assessment of Pax8 expression during pancreatic islet development and in human neuroendocrine tumors. Histochem Cell Biol 2011;136:595-607.
Ye J. et al. Diagnostic utility of PAX8, TTF-1 and napsin A for discriminating metastatic carcinoma from primary adenocarcinoma of the lung. Biotech Histochem 2011.
Albadine R. et al. PAX8 (+)/p63 (−) immunostaining pattern in renal collecting duct carcinoma (CDC): a useful immunoprofile in the differential diagnosis of CDC versus urothelial carcinoma of upper urinary tract. Am J Surg Pathol 2010;34:965-969.
Laury A.R. et al. PAX8 reliably distinguishes ovarian serous tumors from malignant mesothelioma. Am J Surg Pathol 2010;34:627-635.
Turque N. et al. Pax-QNR/Pax-6, a paired box- and homeobox-containing gene expressed in neurons, is also expressed in pancreatic endocrine cells. Mol Endocrinol 1994;8:929-938.
Nonaka, D. et al. Diagnostic Utility of Thyroid Transcription factors PAX8 and TTF-2 in Thyroid Epithelial Neoplasms. Mod Pathol. Feb. 2008; 21(2): 192-2004.
Panka et al. Variable region framework differences result in decreased or increased affinity of variant anti-digoxin antibodies. Proc. Natl. Acad. Sci. USA, vol. 85, pp. 3080-3084, May 1988.
Tockman et al, Consideration in Bringing a Cancer Biomarker to Clinical Application. Cancer Research vol. 52 p. 2711s (1992).
Janicke et al., Urokinase-type Plasminogen Activator (u-PA) Antigen in a Predictor of Early Relapse in Breast Cancer. Fibrinolysis vol. 4 p. 69 (1990).
Paul, Structure and Function of Immunoglobulins. Fundamental Immunology, 3rd Edition, 1993, pp. 292-295.

Rudikoff et al Single Amino Acid Substitution Altering Antigen-binding Specificity (Proc. Natl. Acad. Sci. USA 1982 vol. 79: p. 1979-82).
de Pascalis et al., Grafting of "Abbreviated" Complementarity-Determining Regions Containing Specificity-Determining Residues Essential for Ligand Contact to Engineer a Less Immunogenic Humanized Monoclonal Anitbody. (The Journal of Immunology (2002) 169,3076-3084).
Brown et al. Tolerance to Single, but Not Multiple, Amino Acid Replacements in Anitbody VH CDR2. (J. Immunol. May 1996; 156(9):3285-3291.
Casset et al. A Peptide Mimetic of an Anti-CD4 Monoclonal Antibody by Rational Design. (2003) BBRC 307, 198-205.
Brown, H. M. Et al. Uroplakin-III to Distinguish Primary Vulvar Paget Disease From Paget Disease Secondary to Urothelial Carcinoma, Human Path. 2002;33:545-548.
Koga, F. et al. Impaired p63 Expression Associates with Poor Prognosis and Uroplakin III Expression in Invasive Urothelial Carcinoma of the Bladder, Clin Cancer Res. 2003;9:5501-5507.
Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003;27:1434-1441.
Matsumoto, K. et al. Loss Expression of Uroplakin III is Associated with Clinicopathologic Features of Aggressive Bladder Cancer, Urology. 2008;72:444-449.
Mhawech, P. et al. Immunohistochemical Profile of High-Grade Urothelial Bladder Carcinoma and Prostate Adenocarcinoma, Human Path. 2002;33:1136-1140.
Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract. Am J Pathol. 1999;155:1047-1050.
Ohtsuka, Y. et al. Loss of uroplakin III expression is associated with a poor prognosis in patients with urothelial carcinoma of the upper urinary tract, BJU International, 2006;97:1322-1326.
Parker, D. C. et. al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003;27:1-10.
Wu, X. R. et. al. Mammalian Uroplakins, A group of highly conserved urothelial differentiation-related membrane proteins, J Biol Chem. 1994;269:13716-13724.
Moll, R. et al. Uroplakins, Specific Membrane Proteins of Urothelial Umbrella Cells, as Histological Markers of Metastatic Transitional Call Carcinomas. Am J Pathol, vol. 147, No. 5, Nov. 1995.
Kaufmann, O. et al. Uroplakin III Is a Highly Specific and Moderately Sensitive Immunohistochemical Marker for Primary and Metastatic Urothelial Carcinomas, Am J Clin Pathol 2000;113:683-687.
Wu, RL et al. Uroplakin II Gene is expressed in transitional cell carcinoma but not in bilharzial bladder squamous cell carcinoma: alternative pathways of bladder epithelial differentiation and tumor formation. Cancer Research, Mar. 15, 1998, vol. 58, No. 6, pp. 1291-1297.
Yu, C et al. PSA and NIKX3.1: A Comparative IHC Study of Sensitive and Specificity in Prostate Cancer. BioCareMedical, Presented at USCAP, Abstract #1070, Mar. 19-21, 2012. <uri: http://biocare.net/wp-content/uploads/PSANKX100.pdf>.
Wu XR, Kong XP, Pellicer A, Kreibich G, Sun TT.; Uroplakins in urothelial biology, function, and disease; Kidney Int. Jun. 2009;75(11):1153-65.
Wu X, Kakehi Y, Zeng Y, Taoka R, Tsunemori H, Inui M. J ; Uroplakin II as a promising marker for molecular diagnosis of nodal metastases from bladder cancer: comparison with cytokeratin 20.; Urol. Dec. 2005;174(6):2138-4.
Olsburgh J, Harnden P, Weeks R, Smith B, Joyce A, Hall G, Poulsom R, Selby P, Southgate J.J; Uroplakin gene expression in normal human tissues and locally advanced bladder cancer Pathol. Jan. 2003;199(1):41-9.

(56) References Cited

OTHER PUBLICATIONS

Lu JJ, Kakehi Y, Takahashi T, Wu XX, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. Aug. 2000;6(8):3166-71.

Li, S. M. et al. Detection of circulating uroplakin-positive cells in patients with transitional cell carcinoma of the bladder; .J Urol. Sep. 1999;162(3 Pt 1):931-5.

Kong XT, Deng FM, Hu P, Liang FX, Zhou G, Auerbach AB, Genieser N, Nelson PK, Robbins ES, Shapiro E, Kachar B, Sun TT.; Roles of uroplakins in plaque formation, umbrella cell enlargement, and urinary tract diseases. J Cell Biol. Dec. 20, 2004;167(6):1195-204.

Okegawa T, Kinjo M, Nutahara K, Higashihara E.; Value of reverse transcription polymerase chain assay in peripheral blood of patients with urothelial cancer. J Urol. Apr. 2004;171(4):1461-6.

Hong-Ying Huang, Shahrokh F. Shariat, * Tung-Tien Sun, Herbert Lepor, Ellen Shapiro, Jer-Tsong Hsieh, Raheela Ashfaq, Yair Lotan, and Xue-Ru Wu, ; Persistent Uroplakin Expression in Advanced Urothelial Carcinomas: Implications in Urothelial Tumor Progression and Clinical Outcome. Hum Pathol. Nov. 2007; 38(11): 1703-1713.

Lai, Y. et al. UPK3A: A promising novel urinary marker for the detection of bladder cancer, Urology 76(2), 2010.

Saeb, Parsy, et al. 'Diagnosis of Bladder Cancer by Immunocytochemical detection of minichromosome maintenance protein-2 in cells retrieved from urine' British Journal of Cancer (2012) 107, 1384-1391.

Harris et al. Assessing Genetic Heterogeneity in Production Cell Lines: Detection by Peptide Mapping of a Low Tyr to Gln Sequence Variant in a Recombinant Antibody. Biotechnology, vol. 11 p. 1293-1297, Nov. 1993.

Okazaki et al. Hydronephrosis associated with antiurothelial and antinuclear autoantibodies in BALB/ c-Fcgr2b-/-Pdcd1-/-mice. The Journal of Experimental Medicine. vol. 202, No. 12, pp. 1643-1648, Dec. 19, 2005.

Bondurand, et al. The role of SOX10 during enteric nervous system development. Dev Bioi. Epub May 2, 2013, 382(1):330-43.

GenBank Accession No. CAG30470. SOX10 (*Homo sapiens*). Oct. 16, 2008. (Retrieved from the Internet Dec. 4, 2014: <http://www.ncbi.nlm.nih.gov/protein/CAG30470.1>] 2 pages.

International Application No. PCT/US14/19705, entitled Anti-p40 Antibodies Systems and Methods, filed Feb. 28, 2014, Search Report, dated May 23, 2014. 7 pages.

International Application No. PCT/US14/19705, entitled Anti-p40 Antibodies Systems and Methods, filed Feb. 28, 2014, Written Opinion, dated May 23, 2014. 27 pages.

Sanderson, SO et. al., "An Analysis of the p63/α-Methylacyl Coenzyme A Racemase Immunohistochemical Cocktail Stain in Prostrate Needs Biopsy Speciments and Tissue Microarrays", Am. J. Clin. Path., 2004; 121:220-225.

Zhou, Ming. al., "Basal Cell Cocktail (34βE12 + p63) Improves the Detection of Prostate Basal Cells", Am. J. Surg. Path., 2003: 27(3), 365-371.

Zhou, Ming et al., "Expression and Disgnostic Utility of Alpha-Methylacyl-CoA-Racemase (P504S) in Foamy Gland and Pseudohyperplastic Prostate Cancer", Am. J. Surgical Pathology 27(6): 772-778, 2003.

Anonymous: "PIN cocktail-2 (P504S+p63)", Biocarta. May 4, 2003, pp. 1-2. XP 002667408, Retrieved from the Internet: URL:http://www.biocarta.com/TDS/PM205DSH.pdf [retrieved on Jan. 18, 2012].

Anonymous: "Double vision. The double stain, polymer detection system", Biocare Medical, Aug. 2, 2003, pp. 1-3, XP002667409, retrieved from the Internet: URL: htt12 ://web/archive. org/web/20030802112943/httQ :1/biocare. net/Detection. htm [retrieved Jan. 18, 2012].

Anonymous: "Double vision, The double stain, polymer detection system", Biocare Medical, Oct. 2, 2003, pp. 1-3, XP002667410, retrieved from the Internet: URL:htt12 ://web/archive .org/web/20031 002060452/httQ ://biocare. net/Detection. htm [retrieved Jan. 18, 2012).

Anonymous: "Double vision, The double stain, polymer detection system", Biocare Medical, Jan. 1, 2004, pp. 1-5, XP002667411, retrieved from the Internet: URL: htt12 ://web/archive .org/web/20040 1 01180833/httQ :1/biocare. net/ Detection. htm [retrieved Jan. 18, 2012].

Susan Van Noorden., "Immunocytochemistry for light microscopy a technical update", The biomedical Scientist, XP-002522654, Aug. 2003, pp. 808-811.

Rami Suzuki. et al., "Proliferation and differentiation in the human breast during pregnancy", Differentiation. vol. 66, No. 2-3, XP-002522647, Oct. 2000, pp. 106-115.

BioGenex datasheet, Rabbit Anti-PIN4 Cocktail—AB448ME, release date Aug. 17, 2007.

van der Loos, "Immunoenzyme Multiple Staining Methods", Microscopy Handbooks 45, (1999); Bios Scientific Publishers Ltd: Oxford, UK.

Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.

David Y. Mason, et al., "Double immunofluorescence labelling of routinely processed paraffin sections", Journal of Pathology, vol. 191, No. 4. XP-002522649, Aug. 2000, pp. 452-461.

Susan Van Noorden., "Advances in immunocytochemistry", Folia Histochemica et Cytobiologica, vol. 40, No. 2, XP-008104795, 2002, pp. 121-124.

Van der Loos, et al., "Immunohistochemical Detection of Interferon-y: Fake or Fact?", The Journal of Histochemistry & Cytochemistry, vol. 49, No. 6, XP-002522653, Jun. 2001. pp. 699-709.

Van der loos. et al. "The Animal Research Kit (ARK} Can Be Used in a Multistep Double Staining Method for Human Tissue Specimens", The Journal of Histochemistry & Cytochemistry, vol. 48, (10}: 1431-1437 (2000).

Van der Loos, et al, "Multiple immunoenzyme staining techniques Use of fluoresceinated, biotinylated and unlabeled monoclonal antibodies", Journal of Immunological Methods, 117 (1989), pp. 45-52.

Van der loos. et al. "An Immunoenzyme Triple-staining Method Using Both Polyclonal and Monoclonal antibodies from the same Species. Application of combined direct, Indirect, and Avidin-Biotin Complex (ABC) Technique", The Journal of Histochemistry and Cytochemistry, vol. 35, No. 11, pp. 1199-1204 (1987).

Van der Loos, et al. "Practical suggestions for successful immunoenzyme double-staining experiments", Histochemical Journal (25), pp. 1-13 (1993).

Brunangelo Falin!, et al., "Double Labeled-Antigen Method for Demonstration of Intracellular Antigens in Paraffin-embedded Tissues", The Journal of Histochemistry and Cytochemistry. vol. 30, No. 1, pp. 21-26 (1982).

Data Sheet Fast Red Stubsrate Pack and Compponents for Use with Alakline Phosphatase Detection Kits & BioGenex Automated Staining Systems Jul. 1, 2003 accessed from web.archive.org/web/20030701115828/http://www.bioQenex.com/biOQenex h.html.

Vector Red Alkaline Phosphatase Substrate Kit I Cat. No. SK-5100, Oct. 31, 2000, accessed from web.archive.org/web/20031202200453/http://www.vector.labs.com/protocols.asp.

Cordell et al, Journal of Histochemistry and Cytochemistry, 1984, vol. 32, No. 2 pp. 219-229 attached online version htte://jhc.sageeub.com/content/32/2/219.

Instructions for Universal Alkaline Phosphatase Immunostaining Kit (For Mouse and Rabbit Primary Antibodies) Cat. #KA-50F Apr. 7, 2003 Accessed from web.archive.org/web/20030407222427/http:I/dbiosys.com/new/index.asp?fuse=dsp cat&id=5.

Elias, Immunohistopathology—A Practical Approach to Diagnosis, 2nd Ed. , American Society for Clinical Pathology Press: Chicago, © 2003, p. 36.

Molinie, V. et. al., Mod. Pathol., 2004, 17, 1180.

(56) References Cited

OTHER PUBLICATIONS

Paner, GP, . et. al., Best Prac. In Diag. Immunohist.: Prostate, 2008, 132, 1388.
Rubin, MA et. al., JAMA, 2002,287, 1662.
Shah, RB et. al., Am. J. Surg. Path., 2002, 26, 1161.
Zeta Corporation IVD Data Sheet (Rev 052014) p40 (Clone ZR8), 7 pages.
Tacha, DE and Miller, RT, Appl. Immunohistochem. Mol. Morph .. 2004, 12, 75.
Tavora. F and Epstein, JI, Am. J. Surg. Path., 2008, 32, 1060.
Yang, Y et. al., Am. J. Path., 1997, 150, 693.
Abrahams, NA, et. a f., Histopathology, 2002, 41, 35.
Adley, BP et. al., Am. J. Clin. Path., 2006, 126, 849.
Beach, R et. al., Am. J. Surg. Path., 2002, 26, 1588.
Bostwick, DG and Qian, J., Mod. Pathol., 2004, 17, 360.
Dako Press Release Sep. 14, 2009, New Duoflex Cocktail Antibodies.
Dako Screen Shot DuoFlex Cocktail, Anti-AMACR, Anti-Cytokeratin HMW, Anti-Cytoderatin 5/6: Oct. 5, 2009.
Herawi, M and Epstein, JI, Am. J. Surg. Path., 2007, 31, 889.
Jiang, Z et. al., Am. J. Clin. Path., 2004, 122, 275.
Jiang, Z et. al., Am. J. Clin. Path., 2005, 123,231.
Jiang, Z et. al., Am. J. Surg. Path., 2001, 25, 1397.
Luo, J et. al., Cancer. Res., 2002, 62, 2220.
Reis-Filho et al, Virchows Arch. (2003) vol. 443, pp. 122-132.
12 pages from catalog: "product information form the Sigma-Aldrich Online Catalog" at sigmaaldrich.com/ .. ./ ProductDetail.do?l . . . accessed Feb. 14, 2011.
8 pages from catalog: "product information form the Sigma-Aldrich Online Catalog" at sigmaaldrich.com/. . ./ProductDetail.do?l . . . .accessed Feb. 16, 2011.
Epstein, JI, and Netto, GJ., Biopsy interpretation of the prostate, 2008, Lippincott, Williams & Wilkins: Philadelphia, p. 99.
BioSB p40 IHC of p40 on an FFPE Prostate Tissue, http://www.biosb.com/p40-page, Jul. 29, 2015, 4 pages.
U.S. Appl. No. 61/770,956 entitiled "Systems and Methods for Anti-p40 Antibodies" filed Feb. 28, 2013.
European Patent App. No. 14178215.1 Examination Report dated Dec. 15, 2015, 5 pages.
European Patent App. No. 14178215.1 Search Report dated Dec. 1, 2014, 11 pages.
Cartron, et al. Therapeutic activity of humanized anti-DC20 monoclonal antibody and polymorphism in IgG Fc receptor gene. www.bloodjournal.org, Jan. 21, 2016. 6 pages.
Creative Biolabs, Chimeric IgG construction; (c) 2007-2016 Creative Biolabs, 2 pages.
Foran, James M. et al. European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma. Journal of Clinical Oncology, vol. 18, No. 2/317; Jan. 1, 2000, 7 pages.
Eng, Hui-Yan, et al. Enhanced antigen detection in immunohistochemical staining using a 'digitized' chimeric antibody. Oxford, Protein Engineering, Design & Selection, 2016, vol. 29 No. 1, pp. 11-21. Sep. 25, 2015, 11 pages.
Carter, Paul J. Potent antibody therapeutics by design. Nature Reviews, Immunology. vol. 6, May 2006. pp. 343-357. 15 pages.

ANTI-P40 ANTIBODIES SYSTEMS AND METHODS

This application is a continuation of International Patent Application Number PCT/US2014/019705 filed 28 Feb. 2014 which claims priority to and the benefit of U.S. Provisional Application No. 61/770,956 filed Feb. 28, 2013, each application hereby incorporated by reference herein in its entirety.

TECHNICAL FIELD

This invention relates to the novel anti-p40 antibodies, compositions, cocktails, and kits comprising the antibodies and methods for using the antibodies.

BACKGROUND OF THE INVENTION

Microscopic examination of tissue samples, particularly those obtained by biopsy, is a common method for diagnosis of disease. In particular, immunohistochemistry (IHC), a technique in which specific antibodies are used to detect expression of specific proteins in the tissue sample, may be a valuable tool for diagnosis, particularly for the detection and diagnosis of cancer.

p53 is a tumor suppressor gene that may be mutated in numerous human cancers. (e.g., see article, "p53 Isoforms: An Intracellular Microprocessor?" Khoury M P, Bourdon J C. *Genes Cancer.* 2011 April; 2(4):453-65, and article "p53/p63/p73 isoforms: an orchestra of isoforms to harmonise cell differentiation and response to stress." Murray-Zmijewski F, Lane D P, Bourdon J C. *Cell Death Differ.* 2006 June; 13(6):962-72, each hereby incorporated by reference herein.) Inactivation of p53 may be one of the most common genetic alterations in human cancers and may even be present in about 50% of all human cancers. p53 may respond to a wide variety of cellular stresses, including DNA damage, hypoxia, and metabolic changes, perhaps by activating cellular pathways that may result in cell cycle arrest or apoptosis. p73 may have been cloned and identified as a member of the p53 family, based on sequence homology with key regions of p53. p73 may have demonstrated similar transcriptional activities to p53; however, p73 may not exhibit different activities than p53. (e.g., see article, "Monoallelically expressed gene related to p53 at 1p36, a region frequently deleted in neuroblastoma and other human cancers." Kaghad M, Bonnet H, Yang A, Creancier L, Biscan J C, Valent A, Minty A, Chalon P, Lelias J M, Dumont X, Ferrara P, McKeon F, Caput D. *Cell.* 1997 Aug. 22; 90(4):809-19, each hereby incorporated by reference herein.)

Using PCR primers based on the DNA binding domains of p53 and p73, a gene may have been cloned and the cloned genetic sequence may even have corresponded to a protein of approximately 40-kDa. Therefore, this newly identified gene, an additional member of the p53 family may have been identified as p40. (e.g., see article, "A new human p53 homologue." Trink B, Okami K, Wu L, Sriuranpong V, Jen J, Sidransky D. *Nat Med.* 1998 July; 4(7):747-8, hereby incorporated by reference herein.) Other isoforms of the same gene may have been cloned and their products may have been referred to as p51, p63, or p73L. (e.g., see articles, "Cloning and functional analysis of human p51, which structurally and functionally resembles p53." Osada M, Ohba M, Kawahara C, Ishioka C, Kanamaru R, Katoh I, Ikawa Y, Nimura Y, Nakagawara A, Obinata M, Ikawa S. *Nat Med.* 1998 July; 4(7):839-43, and article "p63, a p53 homolog at 3q27-29, encodes multiple products with transactivating, death-inducing, and dominant-negative activities." Yang A, Kaghad M, Wang Y, Gillett E, Fleming M D, Dötsch V, Andrews N C, Caput D, McKeon F. *Mol Cell.* 1998 September; 2(3):305-16, and article, "A second p53-related protein, p73L, with high homology to p73." Senoo M, Seki N, Ohira M, Sugano S, Watanabe M, Inuzuka S, Okamoto T, Tachibana M, Tanaka T, Shinkai Y, Kato H. *Biochem Biophys Res Commun.* 1998 Jul. 30; 248(3):603-7, and article, "Cloning and functional analysis of human p51, which structurally and functionally resembles p53." Osada M, Ohba M, Kawahara C, Ishioka C, Kanamaru R, Katoh I, Ikawa Y, Nimura Y, Nakagawara A, Obinata M, Ikawa S. *Nat Med.* 1998 July; 4(7):839-43, each hereby incorporated by reference herein.) Each of these isoforms may differ by the presence or even absence of an N-terminal transcriptional activating domain. p40, ΔNp63 and p73L may lack this domain.

The p40/p63/p51/p73L gene may have been found to be overexpressed in cell lines of head and neck squamous cell carcinomas and primary lung squamous cell carcinomas. (e.g., see article, "AIS is an oncogene amplified in squamous cell carcinoma." Hibi K, Trink B, Patturajan M, Westra W H, Caballero O L, Hill D E, Ratovitski E A, Jen J, Sidransky D. *Proc Natl Acad Sci USA.* 2000 May 9; 97(10):5462-7, hereby incorporated by reference herein.) Due to this amplification in squamous cell carcinomas, the p40/p63/p51/p73L gene may be referred to as AIS (amplified in squamous cell carcinoma). The longest isoforms of the p40/p63/p51/p73L gene, perhaps including transcriptional activation domains, may be those cloned and named as p63. (e.g., see article, "p63, a p53 homolog at 3q27-29, encodes multiple products with transactivating, death-inducing, and dominant-negative activities." Yang A, Kaghad M, Wang Y, Gillett E, Fleming M D, Dötsch V, Andrews N C, Caput D, McKeon F. *Mol Cell.* 1998 September; 2(3):305-16, hereby incorporated by reference herein.)

Therefore, for simplicity, the p40/p63/p51/p73L gene may frequently be referred to as p63; however, it should be noted that p40, p63, p51, p73L, and AIS are all terms for the same gene, which may produce transcripts of various lengths, perhaps resulting in protein isoforms of correspondingly various lengths.

The full length of the p63 gene may encode an N-terminal transcriptional activation domain, a DNA binding domain, and a carboxy-oligomerization domain. p63 may have two promoters, which perhaps results in two distinctly different classes of proteins, where one class may contain the trans-activation domain (TA) (perhaps known as p63 or TAp63) and the other class may lack the N-terminal transactivation domain (perhaps known as p40 or ΔNp63). (e.g., see article, "p40: A p63 Isoform Useful for Lung Cancer Diagnosis—A Review of the Physiological and Pathological Role of p63." Nobre A R, Albergaria A, Schmitt F. *Acta Cytol.* 2013; 57(1):1-8, hereby incorporated by reference herein.) The p40 protein may act as a dominant negative factor for transcription by either competing for DNA binding sites or directly binding to p53, p63, or p73 isoforms, perhaps inhibiting their ability to induce transcription. However, in some instances, p40 may activate transcription of genes that are perhaps otherwise not activated by the TA forms of p53, p63, or p73. In one view, the p63 gene may be thought of as producing a family of opposing molecules: perhaps proteins containing a N-terminal transactivation domain, with p53-like tumor suppressor properties, and perhaps proteins lacking an N-terminal domain, with oncogenic properties.

In normal tissue of adults, expression of p63 isoforms may be restricted to the nuclei of basal cells of normal epithelia, such as skin, esophagus, and urothelium or the like, and basal cells of glandular structures in prostate, breast and bronchi or the like. In these cells, expression of p40 may be found to be perhaps about 100-fold higher than that of TAp63. Although p40 and TAp63 may exhibit overlapping tissue distributions, TAp63 may be more expressed in differentiated cells and perhaps less expressed in basal cells, relative to p40 expression. Differences in expression patterns for the isoforms may perhaps indicate different roles for each isoform in development and disease. (e.g., see article, "p40: A p63 Isoform Useful for Lung Cancer Diagnosis—A Review of the Physiological and Pathological Role of p63." Nobre A R, Albergaria A, Schmitt F. *Acta Cytol.* 2013; 57(1):1-8, hereby incorporated by reference herein.)

Determining expression levels of the TAp63 and p40 isoforms may have been useful in diagnosis of cancer. In particular, IHC, using antibodies that bind the TAp63 and/or p40 proteins may have been useful for detecting protein expression and perhaps diagnosing cancer, particularly lung, prostate, breast, and bladder cancer. A rabbit polyclonal (RP) anti-p40 antibody may have been produced and used in an IHC method to identify expression of p40 in head and neck squamous cell carcinoma cell lines and primary lung tumors of the squamous cell carcinoma type. (e.g., see article, "A new human p53 homologue." Trink B, Okami K, Wu L, Sriuranpong V, Jen J, Sidransky D. *Nat Med.* 1998 July; 4(7):747-8, hereby incorporated by reference herein.) A mouse monoclonal anti-p63 antibody (4A4) may also have been produced and used in an IHC method to detect isoforms of p63 protein. (e.g., see article, "p63, a p53 homolog at 3q27-29, encodes multiple products with transactivating, death-inducing, and dominant-negative activities." Yang A, Kaghad M, Wang Y, Gillett E, Fleming M D, Dötsch V, Andrews N C, Caput D, McKeon F. *Mol Cell.* 1998 September; 2(3):305-16, hereby incorporated by reference herein.) Importantly, the RP anti-p40 antibody may bind an epitope sequence that is unique to the p40 isoform, a sequence that is perhaps not present in TAp63. In contrast, the anti-p63 antibody 4A4 may bind an epitope sequence that may be common to both the TA and p40 isoforms, perhaps resulting in 4A4 exhibiting properties of a pan-p63 marker by recognizing both classes of proteins derived from the p63 gene, whereas the RP anti-p40 antibody may recognize only the p40 isoform and may perhaps be a more selective marker.

Lung cancer is the leading cause of cancer death for both men and women. More people die of lung cancer than of colon, breast, and prostate cancers combined. Non-small cell lung carcinoma (NSCLC) comprises approximately 80% of lung cancers and may be classified into several histological types, most commonly may include adenocarcinoma (ADC) or even squamous cell carcinoma (SCC). Classification of lung carcinomas into histological types may be performed by morphological examination using hematoxylin and eosin (H&E) or IHC, and in some cases even, mucin stains; however, accurate classification can be difficult with poorly differentiated or even undifferentiated lung carcinoma. Diagnosis can be further complicated by the use of needle core biopsies, which may provide limited amounts of tissue for both immunohistochemistry and molecular testing, and may include crush artifacts. Additionally, cytology specimens may lack morphological features necessary for diagnosis with H&E alone.

Although the majority of lung cancers (particularly grades I and II) can be diagnosed with only H&E staining, with the advent of targeted therapies, diagnostic needs have changed, and an improved method for classification of a greater number of NSCLC cases is needed. In the past, histologic subtyping of NSCLCs had limited diagnostic value, due to the fact that the same treatment may have been provided to the patient, perhaps regardless of NSCLC subtype. However, the availability of targeted therapies has created a need for accurate subtyping of NSCLC. For example, bevacizumab, a therapeutic humanized monoclonal antibody targeting vascular endothelial growth factor, may be a common treatment for NSCLC patients; however, patients with the SCC subtype should not receive bevacizumab, perhaps due to about 30% mortality rate by fatal pulmonary hemorrhage. Furthermore, enhanced efficacy may have been demonstrated with the addition of premextred to conventional chemotherapy in non-squamous cell carcinomas, but may not in SCC. Therefore, accurate methods for subtyping NSCLC specimens may be useful for the best patient care, with optimal therapeutic efficacy and minimal adverse effects.

IHC may be commonly used to assist pathologists in determining histologic subtype of NSCLC specimens, perhaps particularly discriminating ADC from SCC, as well as from Small Cell Carcinomas of the lung. In particular, IHC antibodies to p40 may be useful in the diagnosis of lung cancer, and perhaps in discriminating histologic subtypes, such as ADC and SCC. Using the RP anti-p40 antibody, expression of p40 protein in primary lung SqCC may have been identified by IHC; whereas, p40 protein may not have been detected in cases of lung adenocarcinoma. (e.g., see article, "AIS is an oncogene amplified in squamous cell carcinoma." Hibi K, Trink B, Patturajan M, Westra W H, Caballero O L, Hill D E, Ratovitski E A, Jen J, Sidransky D. *Proc Natl Acad Sci USA.* 2000 May 9; 97(10):5462-7, hereby incorporated by reference herein.)

Further studies may have shown that the RP anti-p40 antibody may be superior to the pan-p63 antibody 4A4 for the diagnosis of squamous cell carcinoma, and that perhaps the RP anti-p40 antibody may be more specific. In one study, both the RP anti-p40 antibody and pan-p63 antibody stained all 81 cases of SCC that were evaluated, perhaps indicating that both antibodies exhibit equal sensitivity in SCC. In contrast, the pan-p63 antibody stained 74/237 (about 31%) of ADC cases, while the RP anti-p40 antibody stained only 7/205 (about 3%) of ADC cases, perhaps indicating that the RP anti-p40 antibody may be more specific than the pan-p63 4A4. Furthermore, the pan-p63 4A4 antibody stained 82/152 (about 54%) of the large cell lymphoma cases tested, whereas, the RP anti-p40 antibody lacked staining in any of these cases, perhaps resulting in improved specificity for the RP anti-p40 antibody. This study may have shown that IHC detection of p40 instead of detection of multiple p63 isoforms with 4A4 prevents misinterpretation of poorly differentiated ADC or lymphoma as SCC. (e.g., see article, "p40 (ΔNp63) is superior to p63 for the diagnosis of pulmonary squamous cell carcinoma." Bishop J A, Teruya-Feldstein J, Westra W H, Pelosi G, Travis W D, Rekhtman N. *Mod Pathol.* 2012 March; 25(3):405-15 and article, "A study of ΔNp63 expression in lung non-small cell carcinomas." Nonaka D. *Am J Surg Pathol.* 2012 June; 36(6):895-9, each hereby incorporated by reference herein.)

Other studies may also have reported use of the RP anti-p40 antibody in identifying SCC, perhaps in combination with an anti-TTF-1 antibody, which may be a marker for ADC. In one such study, using IHC of small tissue samples from biopsy specimens, 45/46 (about 98%) cases of ADC and SCC were diagnosed, using a combination of RP anti-p40 and anti-TTF-1 antibodies (e.g., see article, "ΔNp63 (p40) and thyroid transcription factor-1 immunoreactivity on small biopsies or cellblocks for typing non-small cell lung cancer: a novel two-hit, sparing-material approach." Pelosi G, Fabbri A, Bianchi F, Maisonneuve P, Rossi G, Barbareschi M, Graziano P, Cavazza A, Rekhtman N, Pastorino U, Scanagatta P, Papotti M. *J Thorac Oncol.* 2012 February; 7(2):281-90, hereby incorporated by reference herein.)

In a similar study, an antibody cocktail containing the RP anti-p40 antibody and an anti-TTF-1 antibody resulted in about 92% sensitivity and about 93% specificity of the RP anti-p40 antibody for SCC, and about 77% sensitivity and about 100% specificity of anti-TTF-1 for ADC. (e.g., see article, "Tissue-Preserving Antibody Cocktails to Differentiate Primary Squamous Cell Carcinoma, Adenocarcinoma, and Small Cell Carcinoma of Lung." Brown A F, Sirohi D, Fukuoka J, Cagle P, Policarpio-Nicolas M, Tacha D, Jagirdar J. *Arch Pathol Lab Med.* 2013 Jan. 4, hereby incorporated by reference herein.)

In normal bladder tissue, TAp63 may be expressed in basal and intermediate urothelial cells, whereas p40 may not be detected. In contrast, p40 expression may be detected by IHC in urothelial carcinoma, perhaps in 29/147 (about 19.7%) of non-invasive cases, and possibly 23/55 (about 41.8%) cases of invasive carcinoma. (e.g., see article, "Distinct expression profiles of p63 variants during urothelial development and bladder cancer progression." Karni-Schmidt O, Castillo-Martin M, Shen T H, Gladoun N, Domingo-Domenech J, Sanchez-Carbayo M, Li Y, Lowe S, Prives C, Cordon-Cardo C. *Am J Pathol.* 2011 March; 178(3):1350-60, hereby incorporated by reference herein.) Expression of p40 may also be a prognostic factor in urothelial carcinoma. For example, cases of muscle invasive urothelial carcinoma that demonstrate expression of p40 may exhibit a median±SD overall survival of perhaps about 11.6±about 1.3 months, perhaps indicating that p40 expression is a predictor of poor prognosis. In contrast, cases of invasive urothelial carcinoma that lack p40 expression may have demonstrated a longer median±SD overall survival of perhaps about 25±about 6.4 months, perhaps indicating that a lack of p40 expression is a predictor of better prognosis. Notably, total p63 expression may not be a prognostic indicator in invasive carcinoma, perhaps because TAp63 and p40 isoforms exhibit opposing biological activities. As a result, a marker that is specific for the p40 isoform may be used for urothelial carcinoma, compared to a pan-p63 marker.

Loss of expression of p40, which may normally be expressed in basal cells of prostate glands, may commonly be used as an indicator adenocarcinoma of the prostate. Specifically, the quantity of p40 mRNA transcript may be lower, perhaps approximately about 2000-times lower or perhaps even undetectable, in prostate cancer cell lines compared to the amount of TAp63 mRNA. Therefore, perhaps p40 is virtually absent in prostate cancer cell lines, whereas TAp63 mRNA is detectable at various levels. In the differential diagnosis of benign and malignant prostate tissue, a method that may detect the loss of p40 may be preferred over a method that may detect TAp63 (e.g., see article, "p63 is a prostate basal cell marker and is required for prostate development." Signoretti S, Waltregny D, Dilks J, Isaac B, Lin D, Garraway L, Yang A, Montironi R, McKeon F, Loda M. *Am J Pathol.* 2000 December; 157(6): 1769-75, and article, "Differential expression of p63 isoforms in normal tissues and neoplastic cells." Nylander K, Vojtesek B, Nenutil R, Lindgren B, Roos G, Zhanxiang W, Sjöström B, Dahlqvist A, Coates P J. *J Pathol.* 2002 December; 198(4):417-27, each hereby incorporated by reference herein.)

In normal breast ducts, myoepithelial cells may form a continuous basal rim along the epithelial structure. The gradual loss of continuity of this basal boundary may be indicative of carcinoma in situ, and the total loss of myoepithelial cells may often be observed in invasive breast carcinoma. Benign lesions may typically retain their continuous myoepithelial layer, while morphologically resembling a malignant lesion. Nuclear staining of myoepithelial cells by IHC may be observed using an anti-p40 antibody. In this manner, an anti-p40 antibody may be useful for evaluating the continuity of the myoepithelial cells in the basal layer and thus aid in the diagnosis of breast lesions. (e.g., see article, "p63, a p53 homologue, is a selective nuclear marker of myoepithelial cells of the human breast." Barbareschi M, Pecciarini L, Cangi M G, Macrì E, Rizzo A, Viale G, Doglioni C. *Am J Surg Pathol.* 2001 August; 25(8):1054-60, hereby incorporated by reference herein.)

Therefore, a clear need exists for a sensitive and even specific anti-p40 antibody for use in cancer diagnosis. Embodiments of the present invention provide an anti-p40 mouse monoclonal antibody [clone BC28] which may be highly sensitive and may even be highly specific. An example of the present invention provides a mouse monoclonal anti-p40 antibody that may detect the presence or absence of p40 protein in certain cancers, including but not limited to SCC, bladder, breast and prostate cancer or the like. In cases of NSCLC, an example of the present invention may have demonstrated excellent sensitivity for lung SCC (about 65/67, about 97%) with perhaps even excellent specificity versus lung ADC (about 0/71, about 0%). When compared to the RP anti-p40 antibody, the mouse monoclonal anti-p40 BC28 may have typically demonstrated cleaner staining patterns, perhaps with fewer artifacts, as well as a lack of staining of macrophages, while even offering the advantages of a monoclonal antibody. BC28 also may not stain some specimens of lung ADC, which may have been stained by the RP anti-p40 antibody, perhaps indicating the superior specificity of BC28 over alternatives. Therefore, a monoclonal anti-p40 antibody, such as BC28, may be preferred for diagnosis, compared to other pan-p63 markers or alternative anti-p40 antibodies.

The development of an anti-p40 antibody may aid in the diagnosis of primary and even metastatic cancers, particularly lung SCC, urothelial carcinoma, prostate adenocarcinoma, and breast carcinoma or the like, and may even aid in distinguishing protein expression of p40 versus TAp63. New anti-p40 antibodies such as mouse monoclonal anti-p40 antibody [BC28], with perhaps equal or superior staining sensitivity, and perhaps even superior staining specificity such as compared to the pan-p63 marker 4A4 and the RP anti-p40 antibody, have been provided in the present invention.

DISCLOSURE OF THE INVENTION

General embodiments of the present invention may include monoclonal antibodies for recognizing p40, methods for their preparation, use in immunohistochemistry, or the like. In embodiments, anti-p40 antibody clones such as the anti-p40 antibody clone BC28 can be obtained by immunizing Balb/C mice with one or more peptides corresponding to a subset of amino acids 1-17 of the human p40 protein.

The p40 peptide may be injected into the BALB/c mice, with an adjuvant, via intraperitoneal injections, perhaps about 5 times at about three week intervals. The immune reactivity to p40 may be assessed by direct ELISA on recombinant p40 protein. Mice with the highest titer may be chosen for developing hybridomas by cell fusion. A hybridoma clone demonstrating the best reactivity to p40 on human tissues may be chosen and may be designated as BC28. The BC28 clone may be tested for isotype and may be identified as a mouse IgG1/kappa. The BC28 antibody may be produced by large scale tissue culture of the hybridoma cells and by ascites in BALB/c mice. The supernatant and antibody ascites may be collected and the antibody may be purified by Protein A affinity column. BC28 may demonstrate specific reactivity to human p40 protein by ELISA, Western blotting, and even human tissues.

Anti-p40 antibodies such as the mouse monoclonal anti-p40 antibody BC28 may be useful for the detection of p40 in tissue samples, perhaps with several significant, but unexpected advantages over currently known antibodies to TAp63 and p40 isoforms. When used in traditional immunohistochemistry procedures, anti-p40 antibodies such as the mouse anti-p40 antibody BC28 may result in nuclear staining of p40 with sensitivity perhaps similar to that of known anti-p63 and anti-p40 antibodies. However, anti-p40 antibodies such as BC28 may exhibit increased specificity, perhaps as compared to anti-p63 antibodies and other known anti-p40 antibodies, which may offer significant improvements. In addition to the possible advantages of being derived from a monoclonal source, anti-p40 antibodies such as BC28 may also offer cleaner staining, with fewer artifacts, and greater cell-type specificity, for example perhaps not staining macrophages, when compared to other known anti-p40 and anti-p63 antibodies. With anti-p40 antibodies such as BC28, analysis of the sample may be simplified and p40 expression in tumor cells may be readily identifiable, allowing diagnosis in cases that may otherwise be difficult, ambiguous, or not even possible, to diagnose.

MODE(S) FOR CARRYING OUT THE INVENTION

Figure 1:
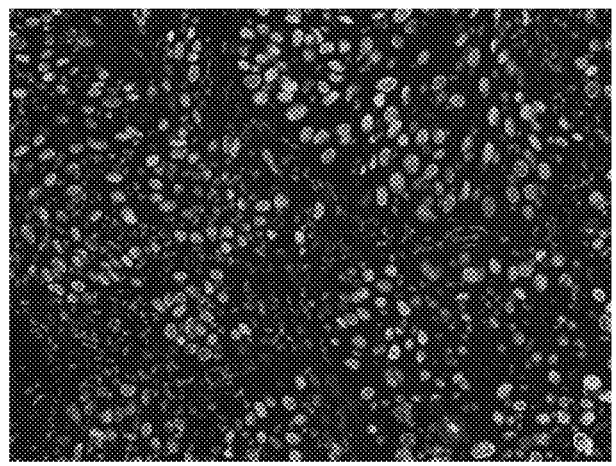
FIG. 1 shows a black and white version of an example of anti-p40 antibody BC28 staining a case of lung squamous cell carcinoma.

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may provide monoclonal antibodies and methods thereof that specifically bind to p40 and may be used for the detection of p40 in the diagnosis for several types of cancers. The monoclonal antibody may be an antibody fragment, a mouse monoclonal antibody, a rabbit monoclonal antibody, a chimeric antibody, a humanized monoclonal antibody, a human monoclonal antibody, an antibody labeled with a detectable signal or stain, an antibody labeled with a toxin, or the like. Systems and methods of the present invention may relate to the monoclonal antibody or its antigen binding portion capable of binding to p40.

Mouse monoclonal antibodies may be commonly used in immunoassay methods to identify specific analytes, including as primary antibodies in immunohistochemistry procedures. Mouse monoclonal antibodies specific for the protein target of interest can be produced using generally known procedures. Generally, exposing a mouse to the antigen of interest (e.g. a peptide fragment of the desired target or the full-length protein target) may induce an immune response in which the mouse generates multiple antibodies that bind the antigen, each of which may be produced by a particular B-cell. These B-cells may be isolated from the mouse spleen and the antibodies produced may be evaluated for their suitability as primary antibodies in IHC. After selecting the optimal antibody, the associated B-cell may be fused with a tumor cell using known procedures, perhaps resulting in a hybridoma, a new cell line that can endlessly replicate and may continuously produce the desired antibody.

Monoclonal antibodies may be preferred in certain embodiments over polyclonal antibodies for several reasons. In particular, monoclonal antibodies may be derived from a single B-cell and as such may recognize a single epitope, perhaps resulting in greater specificity. Monoclonal antibodies may also be conveniently and reproducibly generated in cell culture, perhaps resulting in a constant supply of the desired antibody. Of course, polyclonal antibodies may be utilized in other embodiments.

Anti-p40 antibodies such as a mouse monoclonal anti-p40 antibody BC28 may be produced using these general procedures and may be evaluated by immunohistochemistry for sensitivity and specificity on a variety of normal and neoplastic tissues, perhaps particularly in comparison to the previously known RP anti-p40 antibody and anti-p63 antibody [4A4].

Example of Peptide Preparation: A p40 peptide from amino acid sequence 1 to 17aa, corresponding to the sequence MLYLENNAQTQFSEPQY, may be synthesized on a semi-automatic peptide synthesizer. Similarly, a p40 peptide from amino acid sequence 5 to 17aa, corresponding to the sequence ENNAQTQFSEPQY, may be synthesized on a semi-automatic peptide synthesizer. The peptide may be covalently conjugated to a carrier molecule. In one embodiment, a keyhole limpet haemocyanin (KLH) carrier molecule may be used. The peptide may be also conjugated to goat gamma globulin (GGG) for immunoassay.

Example of Host Immunization: Female BALB/c (about 6 to about 8 weeks old) mice may be immunized intraperitoneally (i.p.) with about 100 µg of human p40 peptide per mouse in complete Freund's adjuvant. p40 peptides used for immunization may correspond to the amino acid sequence of 1-17 from p40, the amino acid sequence of 1-9 from p40, a mixture of the amino acid sequences 1-17 with 5-17 from p40, or any portion of this sequence, and all permutations and combinations thereof. A single peptide may be used as the immunogen, or perhaps a mixture of peptides derived from the amino acid sequence of 1-17, 1-9, a mixture of 1-17 with 5-17, or the like. In certain embodiments, an immunogen that includes the amino acid at position 4, or perhaps includes the amino acids in position 1, 2 or 3, may be used and may produce antibodies with advantageous properties, such as those observed with BC28. About three weeks later, the mice may be boosted with another about 100 µg human p40 per mouse in incomplete Freund's adjuvant about 4 more times in about 3 week intervals. Mice may be bled from the tails, and sera may be collected and stored at about −20° C. for later analysis of antibody titers by enzyme-linked immunosorbent assay (ELISA). Antibodies based from amino acid sequence 5-17 of the p40 protein were not successful and may not have allowed good fusion. Therefore, it may not be desirable to utilize the amino acid sequence 5-17 of the p40 protein to develop an antibody therefrom.

Example of Hybridomas: Hybridomas producing antibodies to p40 may be generated by standard techniques from splenocytes of p40-immunized BALB/c mice. For example, splenocytes from p40-immunized mice may be fused to P3-X63-Ag 8.653 myeloma cells (non-secreting myeloma cells derived from Balb/c mouse) by incubation with about 50% polyethylene glycol at a ratio of about 4:1. Following incubation, cells may be pelleted by centrifugation perhaps at about 300×g for about 10 minutes, washed in about 25 ml of PBS, recentrifuged, and the cell pellet may be resuspended in about 100 ml of fresh Dulbecco's Medium containing about 20% fetal bovine serum (Hyclone, Logan, Utah). Aliquots of about 100 µl can be added to each well of about ten 96-well microtiter plates (Corning, Lowell, Mass.). About twenty four hours later, about 100 µl DMEM culture medium supplemented with hypoxanthine-aminopterin-thymidine (HAT) can be added to each microtiter well. Media may be replaced perhaps after about 4 days with complete media (perhaps containing hypoxanthine-thymidine (HT)). Over the following about 10 days, media may be removed and replaced with fresh media with reduced or perhaps even no HT added. Hybridoma supernatants may be screened by ELISA for antibody reactivity to p40, and hybridoma clones may then be selected and stabilized perhaps by cloning twice by limiting dilution.

Hybridoma cells referred to as Anti-human p40 hybridoma clone BC28 Lot:011713 have been deposited at American Type Culture Collection (ATCC) in Manassas, Va. on Jan. 29, 2013 and has received ATCC Patent Deposit Designation No. PTA-120163 as shown in the attached exhibit entitled, "Budapest Restricted Certificate of Deposit" hereby incorporated by reference herein. Embodiments of the present invention may provide an antibody or fragment thereof produced by the hybridoma deposited at the ATCC and may even include a method for producing a monoclonal antibody by culturing the hybridoma cell which produces the monoclonal antibody capable of specifically recognizing p40 and even allowing the hybridoma to produce monoclonal antibodies.

ELISA: Host anti-sera immune responses to p40 may be measured by ELISA. For example, a solution of p40 (about 1 µg/ml) in phosphate-buffered saline (PBS) may be used to coat about 96-well flat bottom polystyrene plates. The plates may then be blocked with about 1% bovine serum albumin (BSA)-PBS. Either diluted immune sera or hybridoma supernatants may be added and incubated at about 37° C. for about 1 hour. After washing the plates with PBS, the plates may be incubated with goat anti-mouse-HRP reagents (Jackson Labs). Incubations may be done at about 37° C. for about 30 minutes. ABTS substrate may be added to develop color and the absorbance at about 405 nm (A405) may be measured in a microtiter plate reader.

Isotype of monoclonal antibodies: Anti-p40 antibodies such as the BC28 monoclonal antibody may be isotyped using a mouse monoclonal antibody isotyping kit (Invitrogen, Carlsbad Calif.). For example, about 100 µl of supernatant from mouse monoclonal antibody [BC28] cells may be added to the plate coated goat anti mouse IgG1, IgG2A, IgG2B, IgG3, IgM, and IgA heavy chains, kappa and lambda light chains. After about 30 minutes incubation, the plate may be washed about 3 times with PBS and may be incubated with goat anti mouse Ig-HRP reagent. ABTS substrate may be added to develop color and the absorbance at about 405 nm (A405) may be measured in a microtiter plate reader. The BC28 clone may be tested for isotype and may be identified as a mouse IgG1/kappa.

Antibody Production and purification: The selected hybridoma cells from clone BC28 may be cultured with DMEM culture medium supplemented with about 10% FBS or any serum-free medium. The culture supernatants may be further purified by protein A affinity column. The hybridoma cells may also be injected into pristane-primed BALB/c mice to produce antibody ascites. The antibody ascites may be further purified by protein A affinity column. IgG concentration may be measured spectrophotometrically using the extinction coefficient for human IgG of about 1.4 at about 280 nm. The purity of IgG may be determined by SDS-PAGE.

Figure 48:
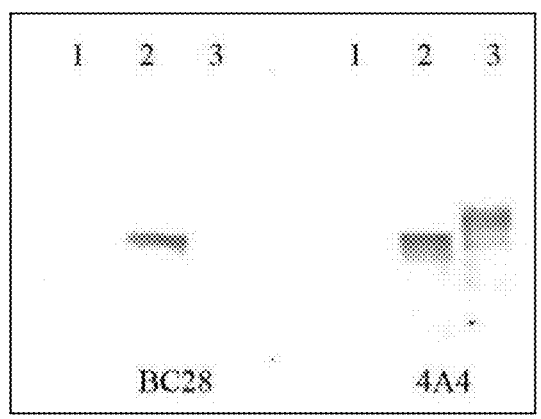
FIG. 48 shows a black and white version of the reactivity of anti-p40 antibody BC28 with p40 protein (left panel, lane 2) and TAp63 protein (left panel, lane 3) by Western blot. The right panel shows the reactivity of anti-p63 antibody 4A4 with p40 protein (right panel, lane 2) and TAp63 protein (right panel, lane 3) by Western Blot. Lane 1 is control lysate in both panels.
Figure 98:
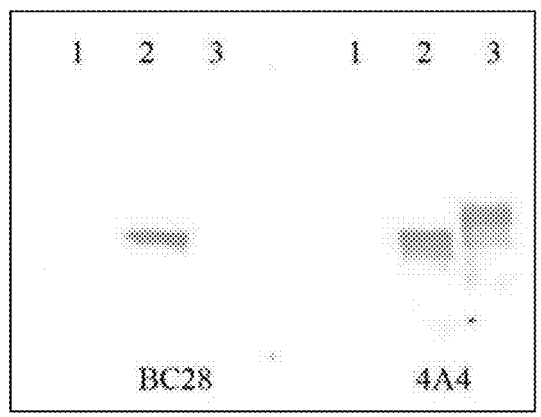
FIG. 98 shows the color version of FIG. 48 of the reactivity of anti-p40 antibody BC28 with p40 protein (left panel, lane 2) and TAp63 protein (left panel, lane 3) by Western blot. The right panel shows the reactivity of anti-p63 antibody 4A4 with p40 protein (right panel, lane 2) and TAp63 protein (right panel, lane 3) by Western Blot. Lane 1 is control lysate in both panels.

Cross-reactivity tested by Western Blotting: The purified monoclonal antibody [BC28] may be characterized by Western Blotting (FIGS. 48 and 98). Full-length p40 or TAp63 transfected cell lysates (Origene, Rockville, Md.) may be subjected to protein gel electrophoresis using about 4 to about 12% SDS-PAGE with Tris-glycine buffer and may be transferred onto nitrocellulose filters in Tris-glycine buffer. Proteins on the blots may be visualized by incubating p63 monoclonal antibody 4A4 or BC28 antibody for about 60 minutes in room temperature after blocking with blocking buffer, perhaps followed by incubating with peroxidase-conjugated goat anti-mouse immunoglobulins. The blots may be detected using TMB chromogen.

Determination of VH and VL sequences: Total RNA may be extracted from hybridomas using Qiagen kit (USA, Gaithersburg, Md.) as per the manufacturer's instructions. First-round RT-PCR may be carried out with QIAGEN® OneStep RT-PCR Kit. RT-PCR may be performed with primer sets specific for the heavy and light chains. For each RNA sample, about 12 individual heavy chain and about 11 light chain RT-PCR reactions can be set up using degenerate forward primer mixtures covering the leader sequences of variable regions. Reverse primers may be located in the constant regions of heavy and light chains. Restriction sites may not be engineered into the primers. The RT-PCR products from the first-round reactions may be amplified in the second-round PCR. About 12 individual heavy chain and about 11 light chain RT-PCR reactions can be set up using semi-nested primer sets specific for antibody variable regions. The amplified cDNAs can be gel purified and may then be sequenced.

BC28 variable domains were sequenced to provide isolated polynucleotides that comprise nucleic acid sequences encoding the amino acid sequences of one or more of the CDRs of the light and/or heavy chain variable regions of a monoclonal antibody described herein that binds to the p40 epitope MLYLENNAQTQFSEPQY identified as SEQ ID NO: 3 or MLYLENNAQ identified as SEQ ID NO: 4. The sequence of the variable region of the heavy chain is identified as SEQ ID NO: 1 and the sequence of the variable region of the light chain is identified as SEQ ID NO: 2. An antibody or fragment thereof may include a polypeptide of the amino acid sequence encoded by the nucleic acid sequence of SEQ ID NO: 1 and/or SEQ ID NO: 2. An antibody or fragment thereof may include a light chain variable region having an amino acid sequence encoded by the nucleic acid sequence of SEQ ID NO: 2 and may even include a heavy chain variable region having an amino acid sequence encoded by a nucleic acid sequence of SEQ ID NO: 1. An antibody or fragment thereof may specifically bind to at least one polypeptide of an amino acid sequence of SEQ ID NO: 3 and/or SEQ ID NO:4. As mentioned herein, a fragment thereof may include an antigen binding fragment thereof.

In embodiments, an antibody or fragment thereof, or even an isolated and purified nucleic acid sequence may have an amino acid sequence of at least about 70% identical to an amino acid sequence encoded by a nucleic acid sequence of SEQ ID NO: 1 and/or SEQ ID NO: 2 and/or the amino acid sequence of SEQ ID NO: 3 and/or SEQ ID NO: 4. An antibody or fragment thereof may specifically bind to at least one polypeptide with an amino acid sequence that is at least about 70% identical to residues of SEQ ID NO: 3 and/or SEQ ID NO: 4. Other percentages may include, but are not limited to, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and perhaps even at least about 99%, or the like.

Epitope Mapping of the mouse anti-p40 [BC28] Binding Sequence: In order to determine the peptide sequence of p40 that is recognized by anti-p40 antibodies such as BC28, epitope mapping may be conducted perhaps using two assays: direct ELISA and even dot blot. In an ELISA assay, the sensitivity and specificity of the anti-p40 [BC28] antibody may be determined by measuring the antibody titer at about 1:500 and about 1:1000. Overlapping peptides at a length of about 15 amino acids each, covering the human p40 protein sequence from perhaps 1 to 17 amino acids, may be used to determine a sequence of BC28 binding.

One of the epitopes for BC28 may include the residues 1-17 amino acids of p40, which is MLYLENNAQTQFSEPQY identified as SEQ ID NO: 3. Another epitope may include the residues 1-9 amino acids of p40, which is MLYLENNAQ identified as SEQ ID NO:4. Yet another epitope may include a mixture of SEQ ID NO:4 and the residues 5-17 amino acids of p40 which is ENNAQTQFSEPQY identified as SEQ ID NO:5. Antibodies may be generated using as an immunogen a peptide sequence of SEQ ID NO: 3, SEQ ID NO:4, or perhaps even a mixture of SEQ ID NO.3 with SEQ. ID NO: 5. The epitope of the mouse monoclonal p40 [BC28] antibody, or a portion thereof, may be a useful antigen for the production of new monoclonal antibodies, including production in species other than mouse (e.g. rabbit, goat, horse, chicken, etc.). Of course, a polyclonal antibody may specifically bind to an epitope in SEQ ID NO: 3, SEQ NO ID:4, or perhaps even a mixture of SEQ ID NO: 4 and SEQ ID NO. 5, or any combination or permutation thereof.

For direct ELISA protocol, the plates may be first coated with about 100 µl of p40 peptides at about 5 µg/mL in coating buffer (pH about 9.5) overnight at about 4° C., followed by blocking (about 3% BSA) at about 200 Owen for about 1 hour at room temperature. The plates may be incubated with purified p40 antibody at about 100 ng/mL and about 200 ng/mL separately for about 1 hour at about room temperature on an ELISA-plate shaker. Then the plates may be washed perhaps five times with PBST (about 300 µl/well) followed by the addition of goat anti-mouse IgG-HRP to the plates and incubation for about 1 hour on a plate-shaker. The plates may then be washed with PBST (about 300 µl/well) and blotted to dry, and TMB may be added at about 100 µl/well, developed for about 5 min on a shaker, and may even be followed by a stop solution (about 50 µl/well). Absorbance may be measured at about 450 nm on an ELISA plate reader perhaps according to the manufacturer's recommendation.

For the dot blot assay, a nitrocellulose membrane may be blotted with about 1 µl at a concentration of about 1 mg/ml the peptide, quadruplicates per peptide. This membrane may be incubated for about 1 hour at room temperature until it may be completely dry. The membrane may be blocked with about 3% BSA in TBST (e.g., about 50 mM Tris, about 0.5 M NaCl, about 0.05% Tween-20, pH about 7.4) for about 1 hour at room temperature, then mouse anti p40 antibody

[BC28] may be added at about 200 ng/ml for about 1 hr at RT in TBST. Then the membrane may be washed for about 3 times (about 10 minutes each) in TBST on an orbital shaker, followed by incubating with secondary antibody goat anti mouse IgG1-AP for about 1 hour at room temperature in TBST. The membrane may be washed perhaps about 3 times (about 10 minutes each) in TBST on a rocker. The binding may be detected by adding Western Glo Chemiluminescent detection reagents and exposing to film.

IHC method with anti-p40 BC28: Immunohistochemistry using anti-p40 antibodies such as the mouse monoclonal anti-p40 antibody BC28 may be performed on formalin-fixed paraffin embedded (FFPE) tissue samples using procedures generally known to those in the art, as generally exemplified by the following non-limiting examples (e.g., washes with Tris-buffered saline, pH about 7.6, between steps):

1) Sections (~5 μm) of formalin fixed paraffin-embedded tissues may be mounted on commercially available microscope slides perhaps coated with polylysine.
2) Sections may be deparaffinized (using xylenes or a xylene-substitute) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Diva, Decloaking Chamber; Biocare Medical) and may be heated to about 125° C. for about 30 seconds. [Other antigen retrieval methods known to those skilled in the art (e.g., steamer, microwave oven, enzyme, or the like) may also be acceptable.] Tissues may be allowed to cool for about 10 minutes and then may be rinsed with deionized water.
4) The p40 antibody BC28 may be applied in a phosphate-buffered solution (pH about 6.0) with bovine serum albumin as carrier protein for about 30 minutes. The p40 antibody BC28 may be diluted perhaps 1:500.
5) Detection of the p40 antibody perhaps with a horseradish peroxidase (HRP) conjugated secondary antibody (MACH 4 Universal HRP-Polymer Detection, Biocare Medical) may be accomplished in two steps. An initial application of a rabbit anti-mouse IgG antibody for about 10 minutes may be followed by incubation with a goat anti-rabbit-HRP conjugate for about 10 minutes.
6) In perhaps a final detection step, 3,3'-diaminobenzidine (DAB) in buffer perhaps containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of sites of p40 expression.
7) Slides may be briefly counterstained perhaps in a modified Mayer's hematoxylin.

Results of IHC Staining with mouse monoclonal anti-p40 antibody BC28: Using the above protocol, a variety of normal and neoplastic tissues were evaluated for p40 expression using BC28 and in some cases compared to staining patterns using a RP anti-p40 antibody and a mouse monoclonal anti-p63 antibody [4A4]. All antibodies were optimized for titer (e.g., concentration) using methods well known to those in the art. For example, various antibody titers were evaluated to maximize staining intensity, perhaps while minimizing or even eliminating background staining. For each antibody, the titer that provided the maximum staining intensity, perhaps with the minimal background staining, was used.

Figure 2:
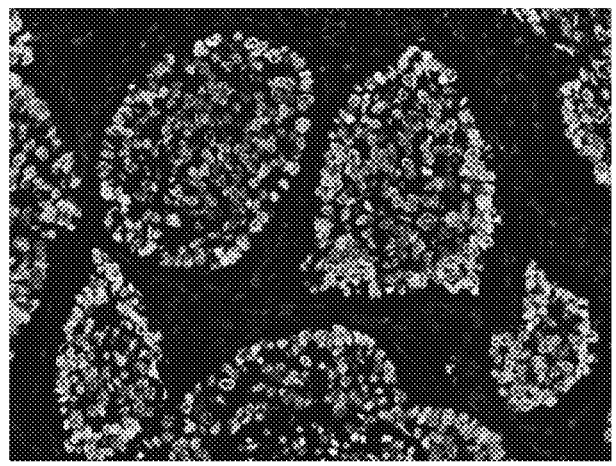
FIG. 2 shows a black and white version of an example of anti-p40 antibody BC28 staining a case of lung squamous cell carcinoma.
Figure 3:
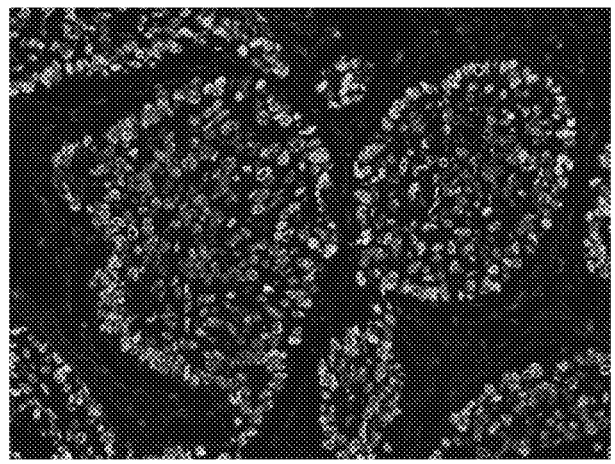
FIG. 3 shows a black and white version of an example of RP anti-p40 antibody staining the same case of lung squamous cell carcinoma as shown in FIG. 2.
Figure 51:
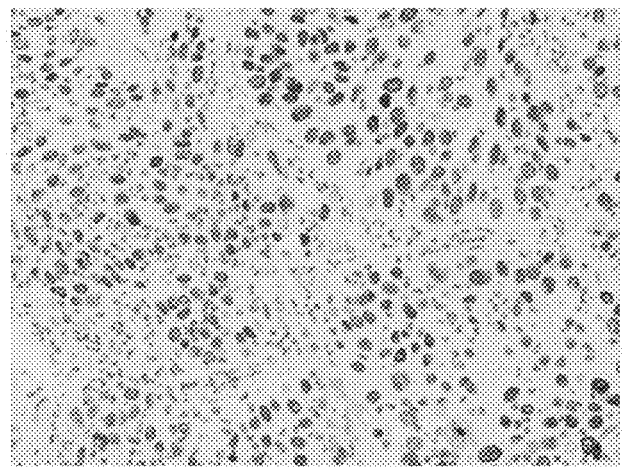
FIG. 51 shows the color version of FIG. 1 of an example of anti-p40 antibody BC28 staining a case of lung squamous cell carcinoma.
Figure 52:
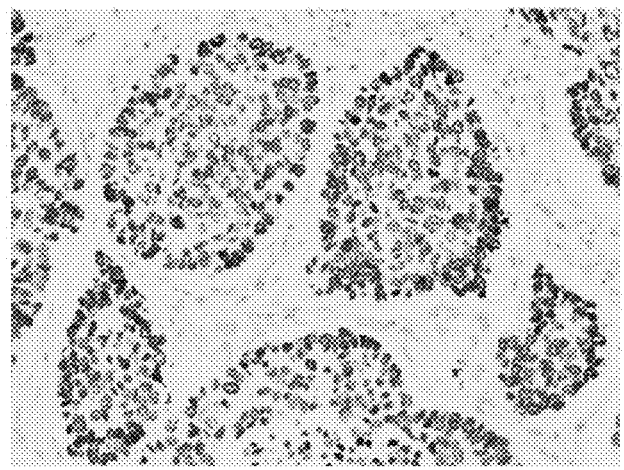
FIG. 52 shows the color version of FIG. 2 of an example of anti-p40 antibody BC28 staining a case of lung squamous cell carcinoma.
Figure 53:
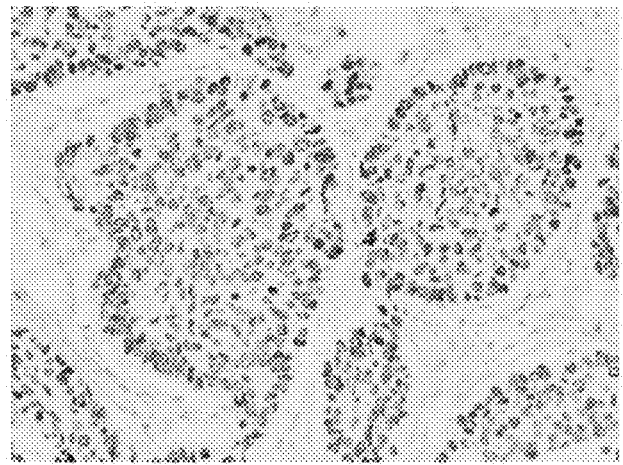
FIG. 53 shows the color version of FIG. 3 of an example of RP anti-p40 antibody staining the same case of lung squamous cell carcinoma as shown in FIG. 52.

FIGS. 1 and 51 shows staining of a FFPE specimen of lung squamous carcinoma by anti-p40 antibody [BC28]. Nuclear staining of p40 is observed, as expected, with no apparent background staining. A different case of lung squamous cell carcinoma stained with BC28 is shown in FIGS. 2 and 52. Staining of p40 with BC28 may be notably strong, perhaps even with no apparent background or non-specific staining. In contrast, staining the same case with RP anti-40 antibody may result in less intense staining and noticeably light background staining in the stromal tissue (FIGS. 3 and 53).

Figure 4:
FIG. 4 shows a black and white version of an example of anti-p40 antibody BC28 on a case of lung adenocarcinoma, with no staining by BC28.
Figure 5:
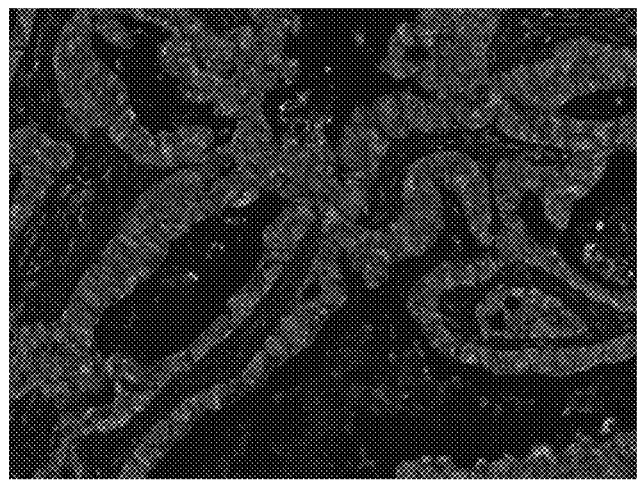
FIG. 5 shows a black and white version of an example of RP anti-p40 antibody staining the same case of lung adenocarcinoma as shown in FIG. 4.
Figure 54:
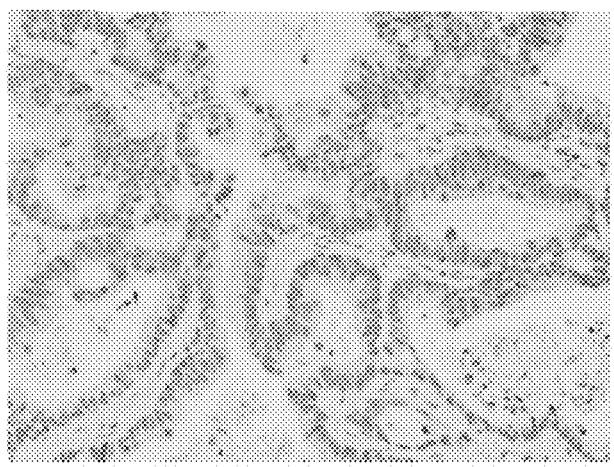
FIG. 54 shows the color version of FIG. 4 of an example of anti-p40 antibody BC28 on a case of lung adenocarcinoma, with no staining by BC28.
Figure 55:
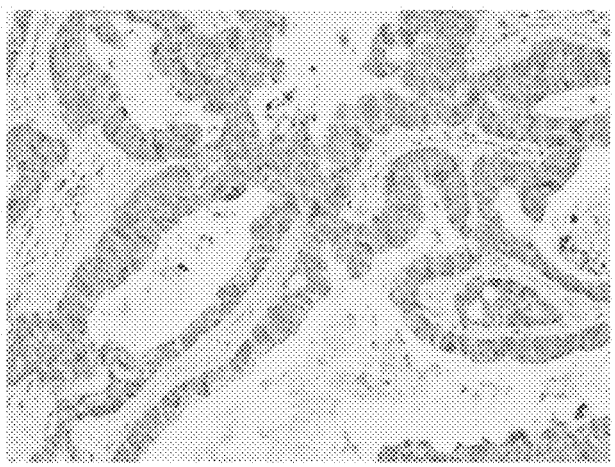
FIG. 55 the color version of FIG. 5 of an example of RP anti-p40 antibody staining the same case of lung adenocarcinoma as shown in FIG. 54.

In FIGS. 4 and 54, BC28 was applied to a case of lung adenocarcinoma, with perhaps no visible staining. This may be a useful result, as p40 may not be expected to be significantly expressed in lung adenocarcinoma, therefore negative staining may be preferred. Staining the same case of lung adenocarcinoma with RP anti-p40 antibody may result in positive cytoplasmic staining of moderate intensity, a potentially ambiguous result that makes it more difficult for interpretation (FIGS. 5 and 55).

Figure 6:
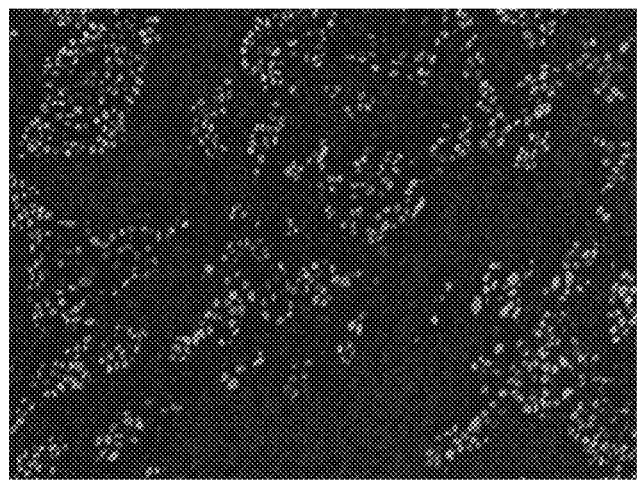
FIG. 6 shows a black and white version of an example of anti-p40 antibody BC28 staining a case of bladder cancer.
Figure 7:
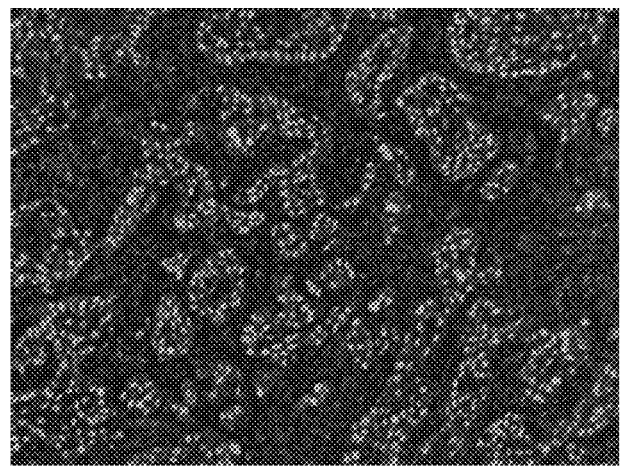
FIG. 7 shows a black and white version of an example of anti-p63 antibody 4A4 staining the same specimen of bladder cancer as shown in FIG. 6.
Figure 8:
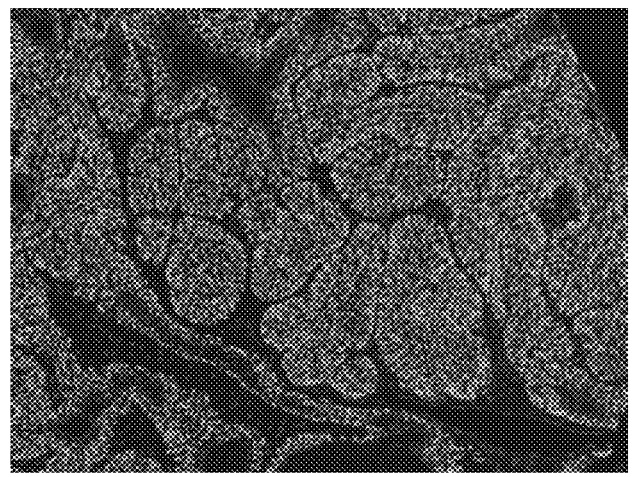
FIG. 8 shows a black and white version of an example of anti-p40 antibody BC28 staining a case of bladder cancer.
Figure 56:
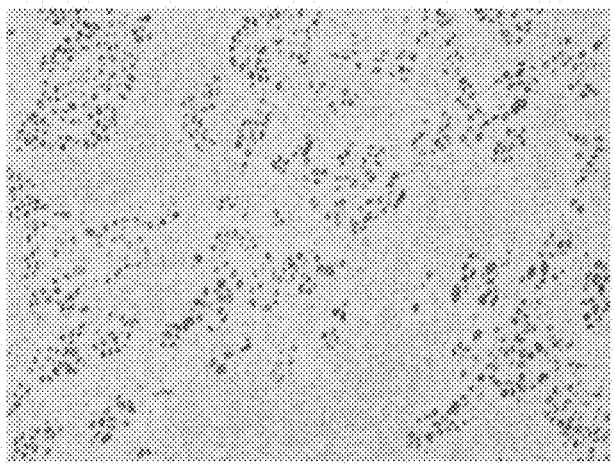
FIG. 56 shows the color version of FIG. 6 of an example of anti-p40 antibody BC28 staining a case of bladder cancer.
Figure 57:
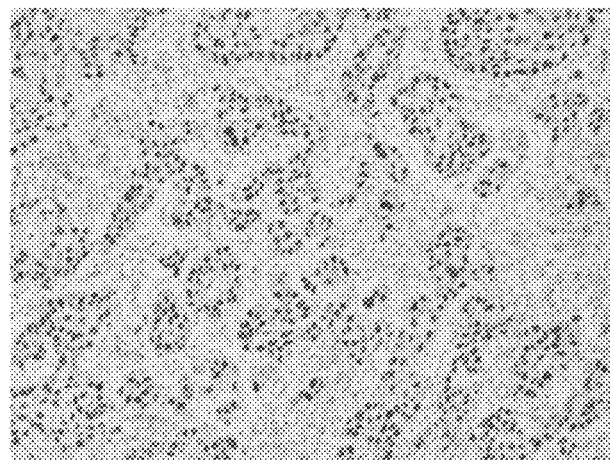
FIG. 57 shows the color version of FIG. 7 of an example of anti-p63 antibody 4A4 staining the same specimen of bladder cancer as shown in FIG. 56.
Figure 58:
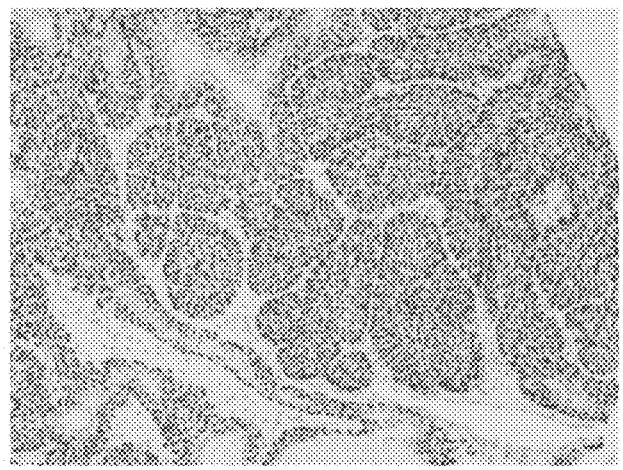
FIG. 58 shows the color version of FIG. 8 of an example of anti-p40 antibody BC28 staining a case of bladder cancer.

FIGS. 6, 7, 56 and 57 show examples of staining by BC28 and RP anti-p40 on a case of bladder cancer (transitional cell carcinoma of the bladder, or urothelial carcinoma). In FIGS. 6 and 56, strong nuclear staining of p40 may be observed, perhaps even with minimal or no background staining. In FIGS. 7 and 57, lighter nuclear staining of p63 is observed with cytoplasmic background staining. FIGS. 8 and 58 shows an example of strong staining with BC28 in urothelial carcinoma.

Figure 9:
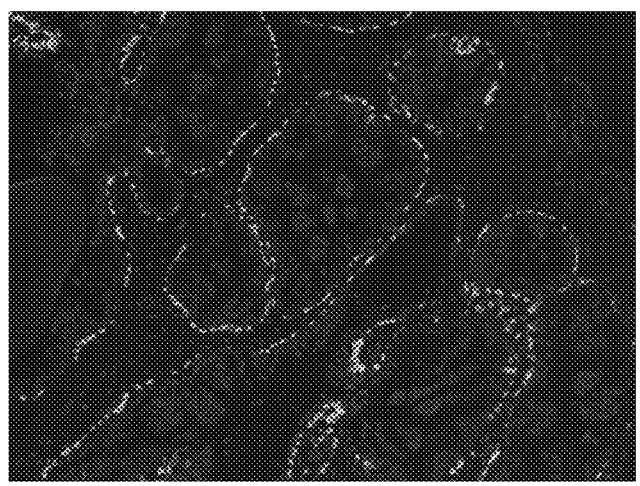
FIG. 9 shows a black and white version of an example of anti-p40 antibody BC28 staining normal prostate glands.
Figure 10:
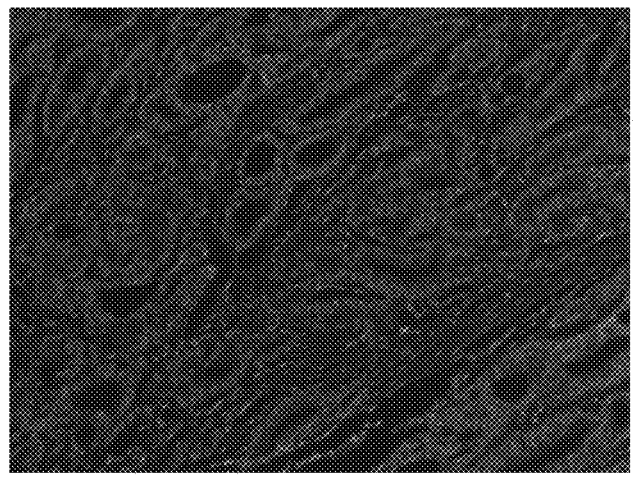
FIG. 10 shows a black and white version of an example of anti-p40 antibody BC28 on a case of prostate adenocarcinoma, with no staining by BC28.
Figure 59:
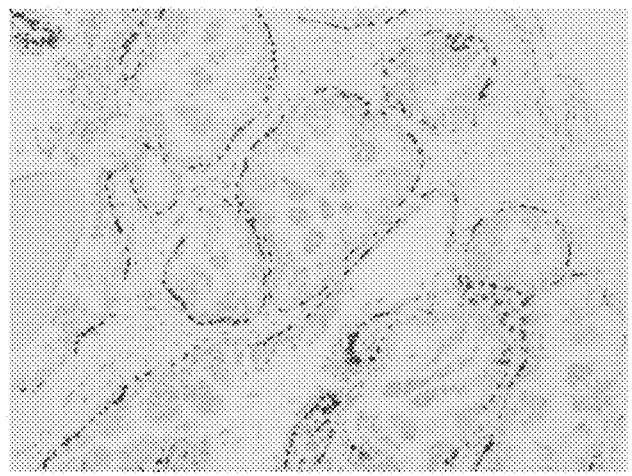
FIG. 59 shows the color version of FIG. 9 of an example of anti-p40 antibody BC28 staining normal prostate glands.
Figure 60:
FIG. 60 shows the color version of FIG. 10 of an example of anti-p40 antibody BC28 on a case of prostate adenocarcinoma, with no staining by BC28.

Expression of p40 may be expected in the basal cells of prostate glands, perhaps consistent with the staining observed in normal prostate with BC28 (FIGS. 9 and 59). Progression from pre-malignant lesions such as prostatic intraepithelial neoplasia (PIN) to invasive prostatic adenocarcinoma may result in the loss of expression of p40 in basal cells. As a result, a lack of staining with BC28 may be a useful marker for the absence of p40 in prostate cancer, as shown in FIGS. 10 and 60. In some cases of prostate, BC28 may provide more intense, sharper staining, and perhaps stain a greater number of basal cells than alternative antibodies, such as 4A4 (FIGS. 22 and 72, and 23 and 73, respectively). FIGS. 24, 74, 25 and 75 show examples of prostate tissue stained with BC28 and 4A4, respectively, at low-power magnification. In this case, BC28 and 4A4 demonstrate similar overall staining patterns, perhaps with more intense and sharper staining by BC28.

Figure 11:
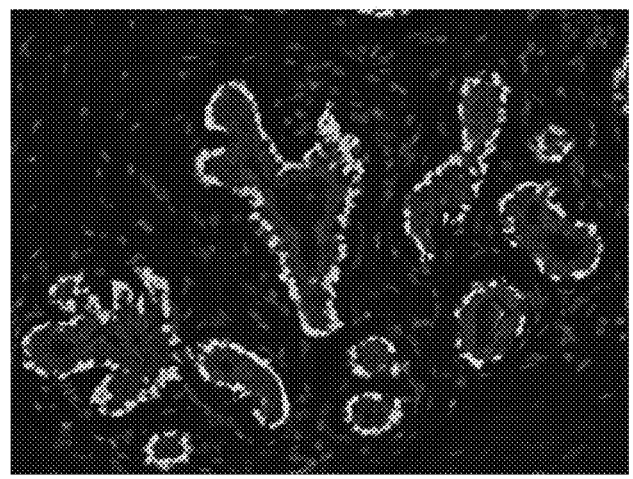
FIG. 11 shows a black and white version of an example of anti-p40 antibody BC28 staining normal breast ducts.
Figure 12:
FIG. 12 shows a black and white version of an example of anti-p40 antibody BC28 staining a case of breast ductal carcinoma in situ (DCIS).
Figure 61:
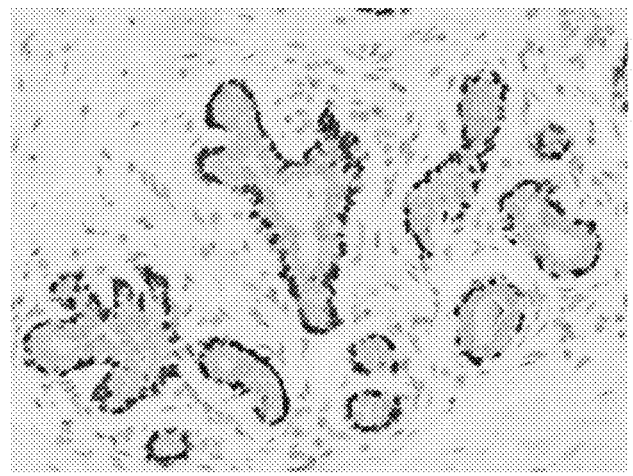
FIG. 61 shows the color version of FIG. 11 of an example of anti-p40 antibody BC28 staining normal breast ducts.
Figure 62:
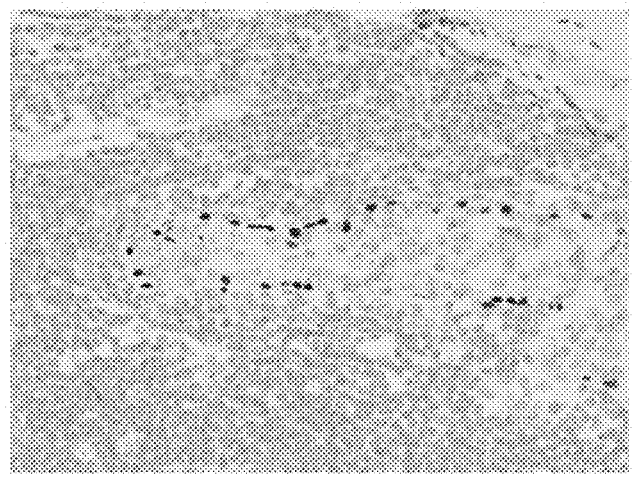
FIG. 62 shows the color version of FIG. 12 of an example of anti-p40 antibody BC28 staining a case of breast ductal carcinoma in situ (DCIS).

Similar to prostate, expression of p40 may be observed in the myoepithelial cells of normal breast ducts, with the gradual loss in early lesions, and may have ultimate absence in invasive breast carcinoma. Staining of p40 in myoepithelial cells of the basal layer of normal breast ducts may beis observed with BC28 (FIGS. 11 and 61). In cases of ductal carcinoma in situ, the integrity of the basal layer may be compromised and staining of p40 with BC28 may become discontinuous (FIGS. 12 and 62). In some cases, alternative antibodies, such as 4A4 may produce anomalous cytoplasmic staining in breast tissue, which is absent with BC28 (FIGS. 20, 70, 21, and 71). This cytoplasmic staining with 4A4 may be widespread. The absence of cytoplasmic staining with BC28 may be an advantage.

Figure 13:
FIG. 13 shows a black and white version of an example of anti-p40 antibody BC28 staining a case of basal cell carcinoma of the skin.
Figure 14:
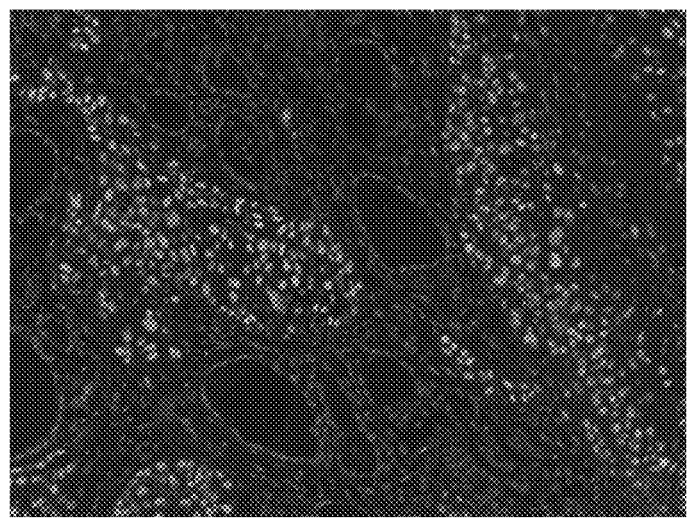
FIG. 14 shows a black and white version of an example of anti-p40 antibody BC28 staining a case of squamous cell carcinoma of the larynx.
Figure 15:
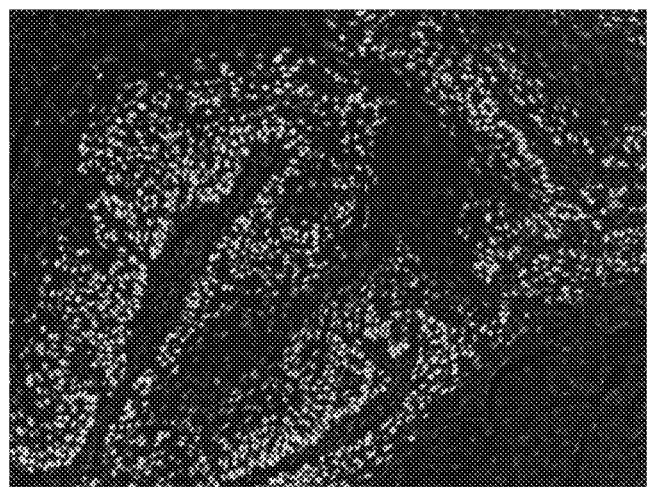
FIG. 15 shows a black and white version of an example of anti-p40 antibody BC28 staining a case of squamous cell carcinoma of the epiglottis.
Figure 63:
FIG. 63 shows the color version of FIG. 13 of an example of anti-p40 antibody BC28 staining a case of basal cell carcinoma of the skin.
Figure 64:
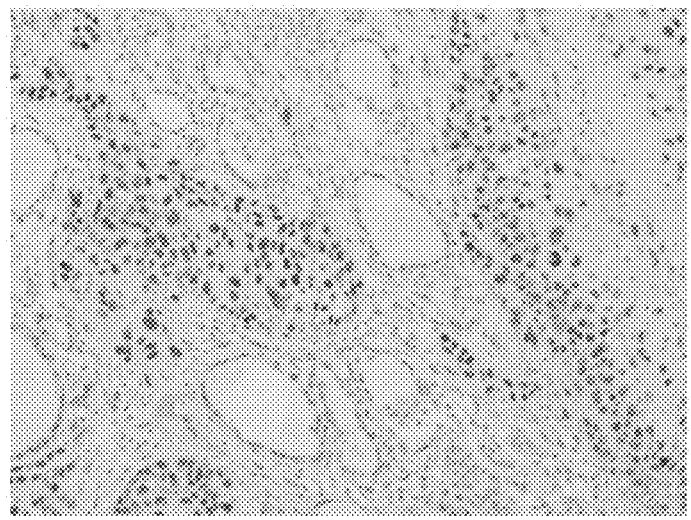
FIG. 64 shows the color version of FIG. 14 of an example of anti-p40 antibody BC28 staining a case of squamous cell carcinoma of the larynx.
Figure 65:
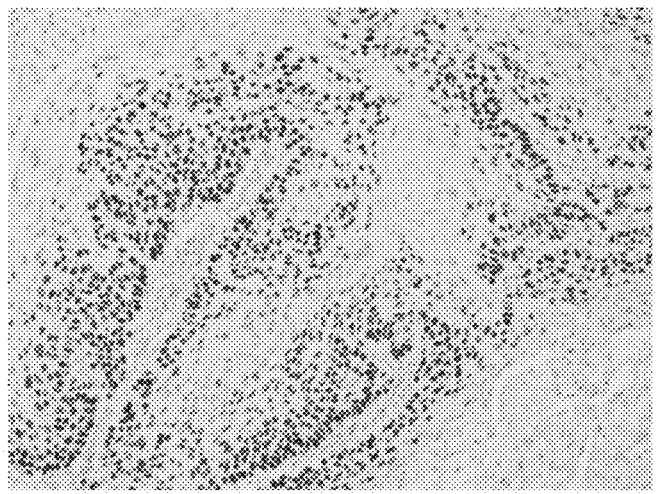
FIG. 65 shows the color version of FIG. 15 of an example of anti-p40 antibody BC28 staining a case of squamous cell carcinoma of the epiglottis.

In basal cell carcinoma of the skin, staining with BC28 may be a useful marker to identify tumor cells by p40 expression (FIGS. 13 and 63). Similarly, staining with BC28 can be useful for identifying p40 expression in squamous cell carcinomas, perhaps even such as those of the larynx or epiglottis (FIGS. 14 and 64 and 15 and 65, respectively).

Figure 16:
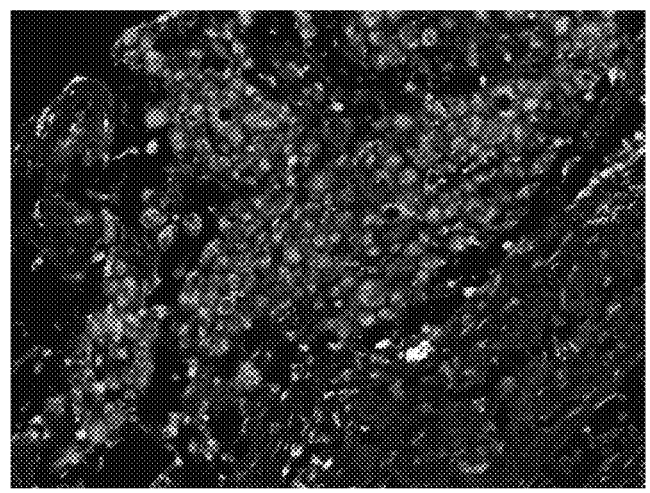
FIG. 16 shows a black and white version of an example of moderate staining of intraalveolar macrophages in the same specimen of lung in FIG. 17, by the RP anti-p40 antibody.
Figure 17:
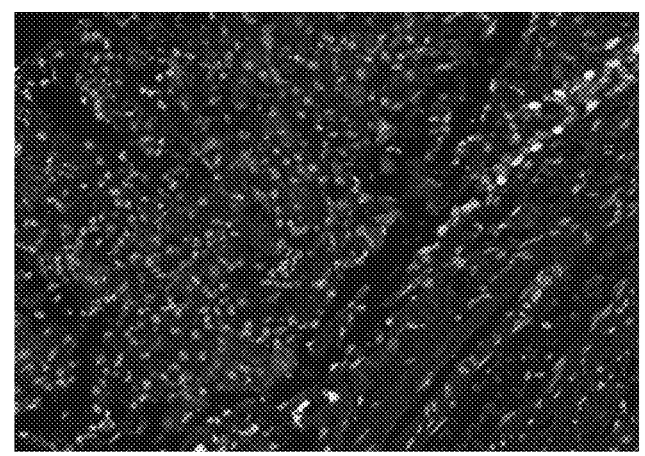
FIG. 17 shows a black and white version of an example of very weak, or perhaps the absence of staining of intraalveolar macrophages in the lung by anti-p40 antibody BC28.
Figure 66:
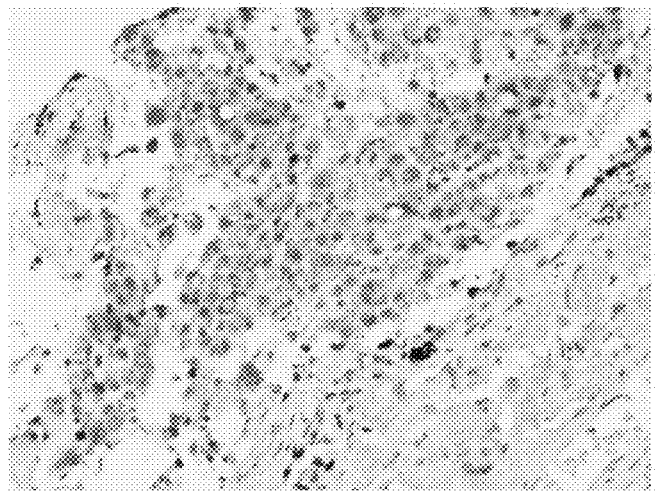
FIG. 66 shows the color version of FIG. 16 of an example of moderate staining of intraalveolar macrophages in the same specimen of lung in FIG. 67, by the RP anti-p40 antibody.
Figure 67:
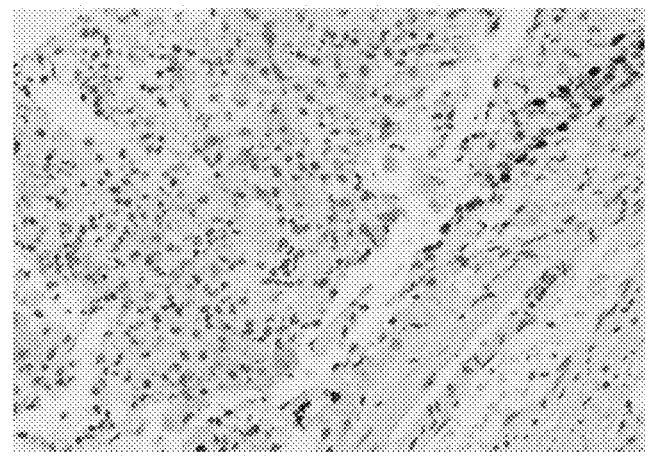
FIG. 67 shows the color version of FIG. 17 of an example of very weak, or perhaps the absence of staining of intraalveolar macrophages in the lung by anti-p40 antibody BC28.

One disadvantage of anti-p40 antibodies other than BC28 may be the staining of intraalveolar macrophages in lung tissue. Positive staining of macrophages may lead to a false positive or an incorrect diagnosis due to erroneous staining. For example, moderate staining of intraalveolar macrophages may be observed with the RP anti-p40 antibody (FIGS. 16 and 66). In contrast, BC28 may not stain intralveloar macrophages in the same manner, perhaps a distinct advantage (FIGS. 17 and 67). The lack of staining of intraalveloar macrophages by BC28 may simplify a diagnostic interpretation and may even eliminate the potential error of a false positive or incorrect diagnosis perhaps due to inaccurate staining of macrophages.

BC28 may provide similar or even superior staining to alternative antibodies. For example, staining of prostate glands with BC28 may be perhaps stronger and even possibly may stain more cells in the basal layer than the anti-p63 antibody 4A4 (FIGS. 22, 72 and 23 and 73, and FIGS. 24 and 74 and 25 and 75).

Figure 18:
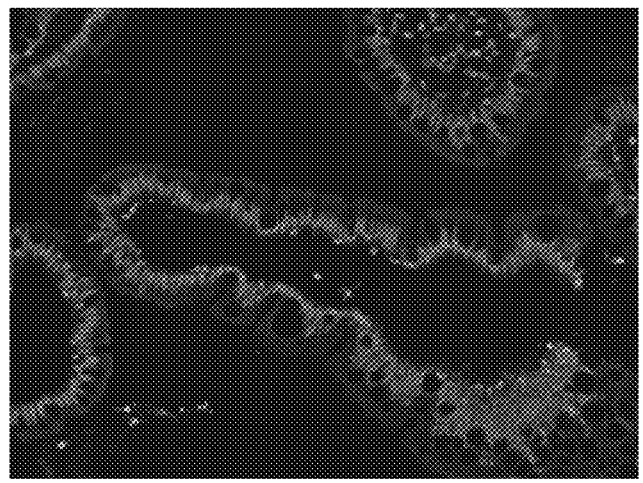
FIG. 18 shows a black and white version of an example of anti-p40 antibody BC28 staining small intestine, with very weak, or perhaps the absence of background staining.
Figure 19:
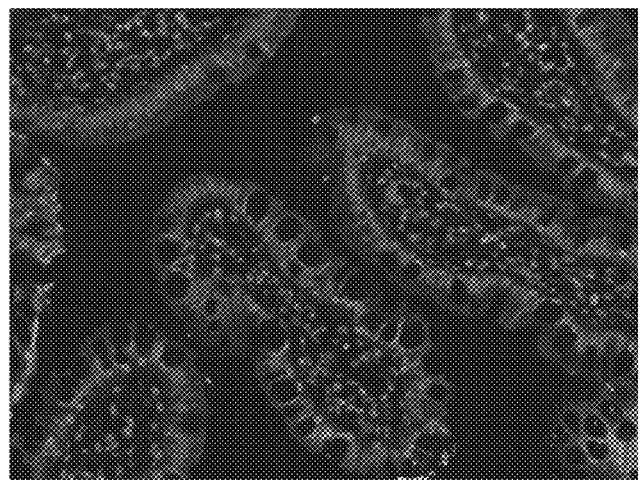
FIG. 19 shows a black and white version of an example of anti-p63 antibody 4A4 staining the same case of small intestine as shown in FIG. 18, where background staining is present.
Figure 20:
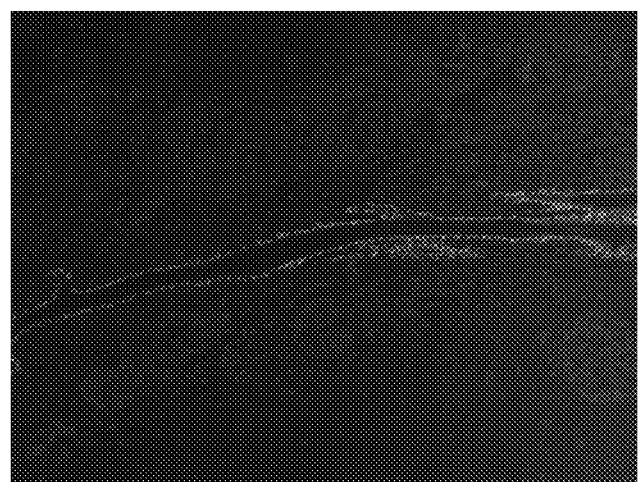
FIG. 20 shows a black and white version of an example of anti-p40 antibody BC28 staining nuclei of myoepithelial cells of a breast duct, without cytoplasmic staining.
Figure 21:
FIG. 21 shows a black and white version of an example of anti-p63 antibody 4A4 staining the same breast specimen of FIG. 20; however, strong, cytoplasmic staining is present.
Figure 22:
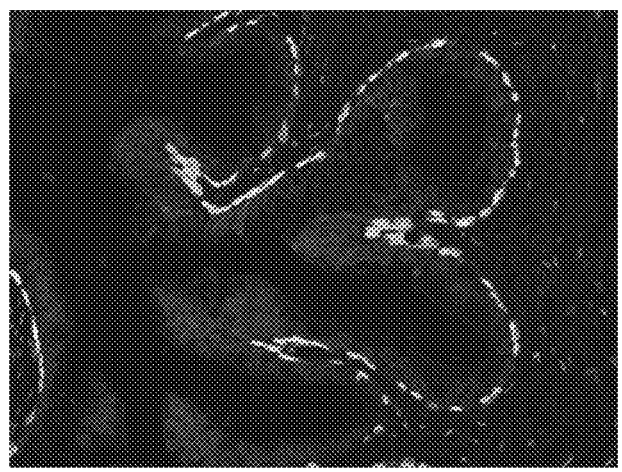
FIG. 22 shows a black and white version of an example of anti-p40 antibody BC28 staining prostate tissue, perhaps a specimen of prostatic intraepithelial neoplasia (PIN), with strong nuclear staining of the basal cells of the gland. Staining is slightly more intense and sharper than that of FIG. 23.
Figure 23:
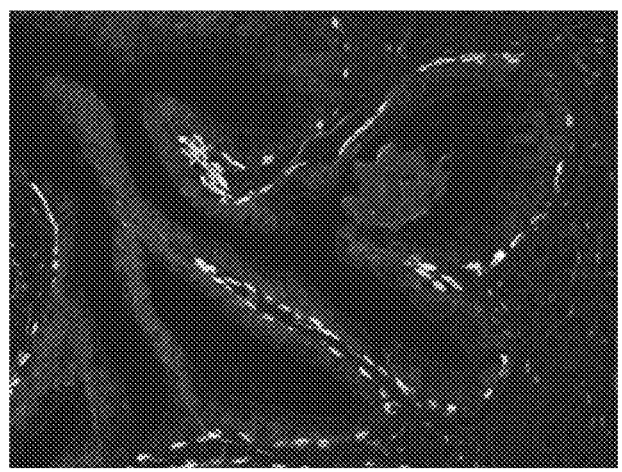
FIG. 23 shows a black and white version of an example of anti-p63 antibody 4A4 staining the same prostate specimen of FIG. 22, with strong nuclear staining of the basal cells of the gland. Staining is slightly less intense and less sharp than that of BC28 in FIG. 22. Also, fewer basal cells are stained by 4A4 than BC28.
Figure 24:
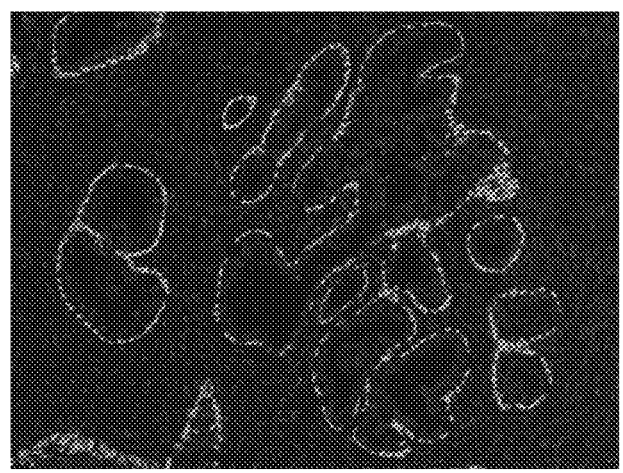
FIG. 24 shows a black and white version of an example of anti-p40 antibody BC28 staining prostate tissue, perhaps a specimen of pro static intraepithelial neoplasia (PIN), with strong nuclear staining of the basal cells of the gland.
Figure 25:
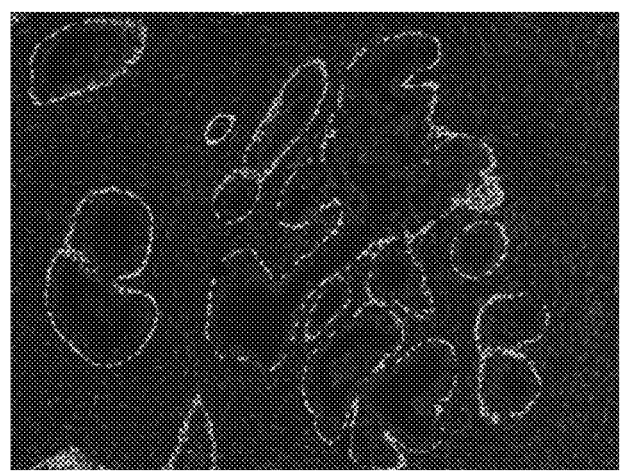
FIG. 25 shows a black and white version of an example of anti-p63 antibody 4A4 staining the same prostate specimen of FIG. 22, with strong nuclear staining of the basal cells of the gland.
Figure 68:
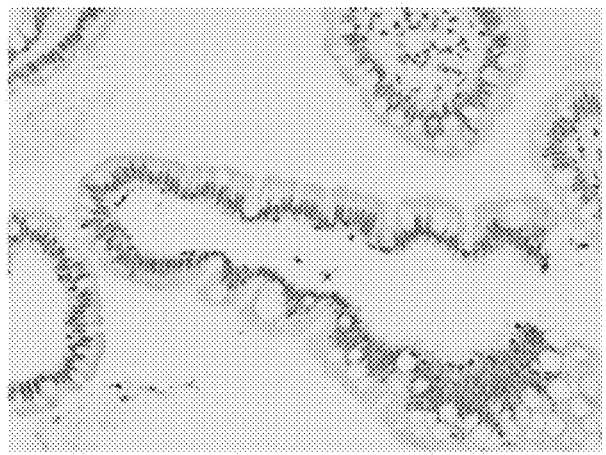
FIG. 68 shows the color version of FIG. 18 of an example of anti-p40 antibody BC28 staining small intestine, with very weak, or perhaps the absence of background staining.
Figure 69:
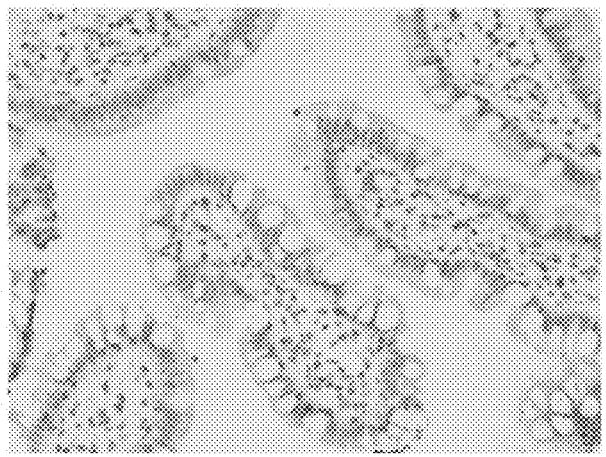
FIG. 69 shows the color version of FIG. 19 of an example of anti-p63 antibody 4A4 staining the same case of small intestine as shown in FIG. 18, where background staining is present.
Figure 70:
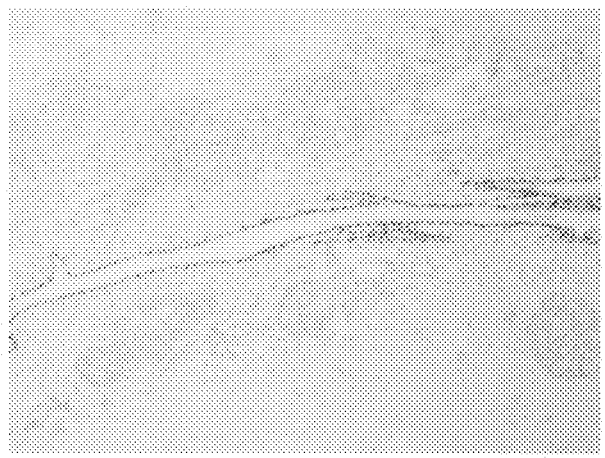
FIG. 70 shows the color version of FIG. 20 of an example of anti-p40 antibody BC28 staining nuclei of myoepithelial cells of a breast duct, without cytoplasmic staining.
Figure 71:
FIG. 71 shows the color version of FIG. 21 of an example of anti-p63 antibody 4A4 staining the same breast specimen of FIG. 70; however, strong, cytoplasmic staining is present.
Figure 72:
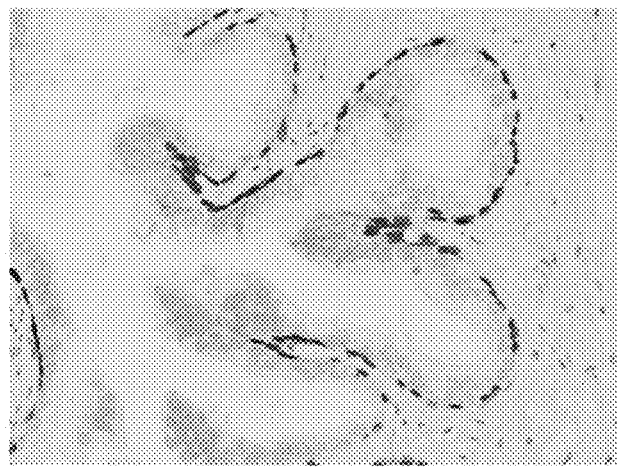
FIG. 72 shows the color version of FIG. 22 of an example of anti-p40 antibody BC28 staining prostate tissue, perhaps a specimen of prostatic intraepithelial neoplasia (PIN), with strong nuclear staining of the basal cells of the gland. Staining is slightly more intense and sharper than that of FIG. 73.
Figure 73:
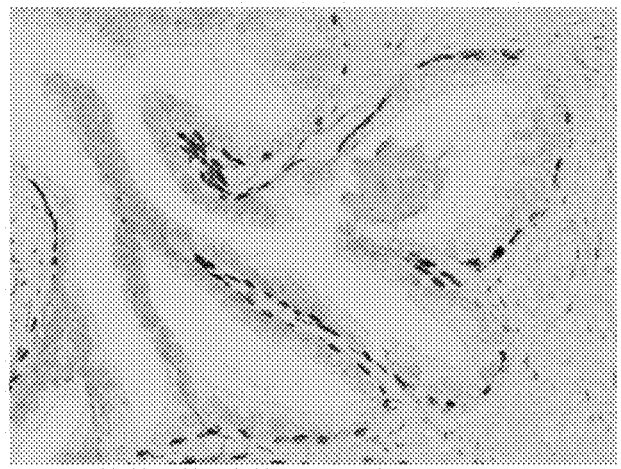
FIG. 73 shows the color version of FIG. 23 of an example of anti-p63 antibody 4A4 staining the same prostate specimen of FIG. 72, with strong nuclear staining of the basal cells of the gland. Staining is slightly less intense and less sharp than that of BC28 in FIG. 72. Also, fewer basal cells are stained by 4A4 than BC28.
Figure 74:
FIG. 74 shows the color version of FIG. 24 of an example of anti-p40 antibody BC28 staining prostate tissue, perhaps a specimen of prostatic intraepithelial neoplasia (PIN), with strong nuclear staining of the basal cells of the gland.
Figure 75:
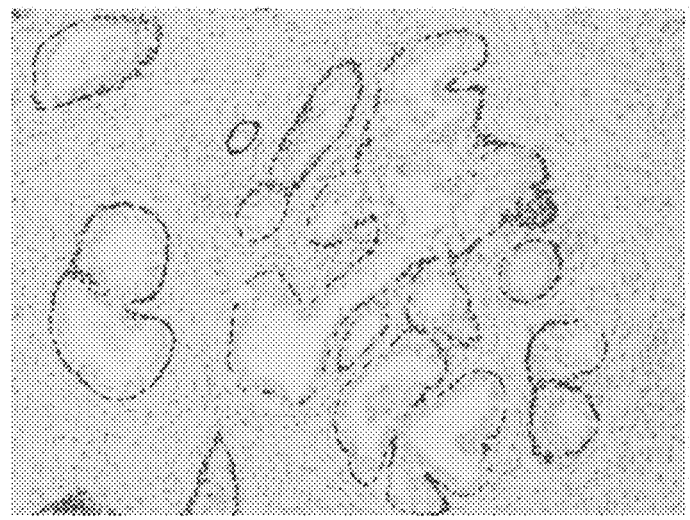
FIG. 75 shows the color version of FIG. 25 of an example of anti-p63 antibody 4A4 staining the same prostate specimen of FIG. 72, with strong nuclear staining of the basal cells of the gland.

When staining nuclear markers, such as p40 or p63, cytoplasmic staining may be a complicating factor for accurate diagnosis. In some cases, BC28 may have the advantage of providing cleaner nuclear staining, perhaps even without cytoplasmic staining. For example, BC28 may stain a case of bladder cancer with clear, nuclear staining, and no cytoplasmic staining (FIGS. 6 and 56), compared to 4A4 which may stain the same specimen with weak to moderate cytoplasmic staining (FIGS. 7 and 57). Similarly, BC28 may be negative in an example of small intestine (FIGS. 18 and 68); whereas, 4A4 may show distinct cytoplasmic staining in the same case (FIGS. 19 and 69). In one example, BC28 also may not produce cytoplasmic staining in breast tissue (FIGS. 21 and 71), whereas cytoplasmic staining is observed with 4A4 (FIGS. 20 and 70). The absence of cytoplasmic staining in cases such as these may be a distinct advantage of BC28.

Table 1 shows the sensitivity of anti-p40 antibody [BC28] staining 67 cases of lung squamous cell carcinoma, using a tissue microarray (TMA) of FFPE tissue. Employing a cut-off of ≥about 5% of tumor cells staining as the criteria to determine a case as "positive" for p40, and conversely <about 5% of tumor cells staining as the criteria to determine a case "negative," 65 of 67 (about 97%) were found to be positive for p40 [BC28]. Diagnosis of tumors of higher grade can sometimes be a challenge. In these specimens, anti-p40 antibody [BC28] identified 35 of 35 (about 100%) of Grade II tumors, and 26 of 28 (about 92.9%) of Grade III tumors.

Table 2 shows an example of the specificity of anti-p40 antibody [BC28] staining 71 specimens of lung adenocarcinoma carcinoma, using a tissue microarray (TMA). Employing a cut-off of ≥about 5% of tumor cells staining as the criteria to determine a case as "positive" for p40, and conversely<about 5% of tumor cells staining as the criteria to determine a case "negative," 0 of 71 (about 0%) were found to be positive for p40 [BC28].

TABLE 1

Anti-p40 Antibody [BC28] staining lung SCC

| Grade | Number of Specimens | Number of Positive Specimens | % Positive | Number of Negative Specimens | % Negative |
|---|---|---|---|---|---|
| Grades I, II & III | 67 | 65 | 97% | 2 | 3% |
| Grade I | 4 | 4 | 100% | 0 | 0% |
| Grade II | 35 | 35 | 100% | 0 | 0% |
| Grade III | 28 | 26 | 92.9% | 2 | 7.1% |

TABLE 2

Anti-p40 Antibody [BC28] staining lung ADC

| Grade | Number of Specimens | Number of Positive Specimens | % Positive | Number of Negative Specimens | % Negative |
|---|---|---|---|---|---|
| Grades I, II & III | 71 | 0 | 0% | 71 | 100% |
| Grade I | 5 | 0 | 0% | 5 | 100% |
| Grade II | 44 | 0 | 0% | 44 | 100% |
| Grade III | 22 | 0 | 0% | 22 | 100% |

TABLE 3

Anti-p40 Antibody [BC28] staining neoplastic tissues

| Pathology | Number of Specimens | Number of Positive Specimens | % Positive | Number of Negative Specimens | % Negative |
|---|---|---|---|---|---|
| Head and neck squamous cell carcinoma | 59 | 46 | 78.0% | 13 | 22% |
| Urothelial carcinoma | 48 | 41 | 85.4% | 7 | 14.6% |
| Breast cancer | 65 | 18 | 27.6% | 47 | 72.3% |
| Prostate cancer | 12 | 0 | 0% | 12 | 100% |

Table 3 shows an example of the sensitivity of the anti-p40 antibody [BC28] in several other neoplastic tissues. Of the 59 cases of head and neck squamous cell carcinoma stained with BC28, 46 (about 78%) were found to be positive. BC28 was also highly sensitive in urothelial carcinoma of the bladder, staining 41/48 (about 85.4%) cases positive. Loss of p40 expression may be expected in breast cancer and prostate cancer. Of the 65 cases of breast cancer stained with BC28, 47 cases (about 72.3%) were negative for p40. In prostate cancer, none of the 12 cases tested were positive for p40. Additionally, 15 cases of prostate tissue, containing benign glands and prostatic intraepithelial neoplasia, were stained with BC28 and compared to p63 [4A4]. Representative areas were compared for the same specimen stained with BC28 and p63 by two separate investigators who found BC28 to be equivalent, or perhaps superior to p63 in staining intensity and sharpness, with perhaps less background; however p63 stained striated muscle and BC28 was negative. Perhaps the absence of staining of striated muscle with BC28 is an advantage.

The sensitivity of anti-p40 antibody [BC28], compared to RP anti-p40 antibody and anti-p63 antibody [4A4], may be demonstrated by staining various cases of lung squamous cell carcinoma with each antibody (Table 4). Using the same criteria, anti-p40 antibody [BC28] identified 65/67 specimens as positive (about 97%). By comparison, RP anti-p40 stained 34/41 (about 83%) of cases of lung squamous cell carcinoma as positive and anti-p63 [4A4] stained 35/41 (about 85%) of cases as positive. Greater specificity may be observed for BC28, compared to RP anti-p40 and 4A4 on cases of lung adenocarcinoma. BC28 did not stain any of the 71 cases of lung adenocarcinoma that were evaluated, therefore, perhaps resulting in no false positives. By comparison, staining with RP anti-p40 resulted in 1/50 (about 2%) cases as positive and 5/50 (about 10%) of cases were found positive when using 4A4.

TABLE 4

Comparison of anti-p40 antibody [BC28], RP anti-p40, and anti-p63 [4A4]

| Lung cancer phenotype | p40 [BC28] | RP p40 | p63 [4A4] |
| --- | --- | --- | --- |
| Squamous cell | 65/67 | 34/41 | 35/41 |
| carcinoma | 97% | 83% | 85% |
| Adenocarcinoma | 0/71 | 1/50 | 5/50 |
|  | 0% | 2% | 10% |

Anti-p40 antibody [BC28] may be highly specific perhaps when evaluated on a variety of normal (Table 5) tissues. Staining of normal tissues with p40 may be observed in the expected tissues based on the presence of squamous epithelium (for example, skin, esophagus, and bladder or the like) and glandular tissues (for example, breast and prostate or the like). Such staining may be expected and anti-p40 antibody [BC28] may not stain any other normal or neoplastic tissues, which may demonstrate its high specificity.

Anti-p40 antibodies such as the monoclonal mouse anti-p40 antibody [BC28] may offer distinct advantages with its improved sensitivity, specificity, and staining properties, perhaps even as compared to RP anti-p40 antibody and monoclonal mouse anti-p63 antibody [4A4]. FIGS. 2, 52 and FIGS. 3, 53 show a comparison of BC28 with RP anti-p40 antibody staining serial sections of the same specimen of lung squamous cell carcinoma, perhaps demonstrating the greater staining intensity and specificity of BC28. For example, the specimen of FIGS. 2 and 52 may exhibit strong nuclear staining with BC28 and no apparent staining in stromal tissue, while the staining of the same specimen with RP anti-p40 antibody FIGS. 3 and 53 may be less intense and result in weak staining in the stromal tissue. One important advantage of BC28 may be improved specificity against lung adenocarcinoma, perhaps even as compared to RP anti-p40 antibody or 4A4. For example, FIGS. 5 and 55 shows a case of lung adenocarcinoma stained with RP anti-p40 antibody, resulting in positive staining; however, staining the same specimen with BC28 (FIGS. 4 and 54) is entirely negative, perhaps demonstrating the superior specificity of BC28. The anti-p40 antibody BC28 may also offer an advantage by not staining intraalveolar macrophages in lung tissue. For example, RP anti-p40 antibody may stain intraalveolar macrophages moderately to strongly (FIGS. 16 and 66). In contrast, BC28 may stain the macrophages of the same specimen either weakly, or perhaps not at all (FIGS. 17 and 67), possibly demonstrating superior specificity of BC28 and even cleaner staining pattern. These examples demonstrate the advantages of BC28 and perhaps show that BC28 has several advantages over known antibodies, including superior sensitivity or specificity, possibly resulting in cleaner staining patterns, with less background or undesirable cytoplasmic staining.

TABLE 5

Anti-p40 antibody [BC28] staining of normal tissues

| Tissue | # positive/total tissues |
| --- | --- |
| Adrenal gland | 0/3 |
| Bladder, urinary | 2/3 |
| Bone marrow | 0/1 |
| Eye | 0/1 |
| Breast | 3/3 |
| Brain, cerebellum | 0/3 |
| Brain, cerebral cortex | 0/3 |
| Fallopian tube | 0/3 |
| Esophagus | 3/3 |
| Stomach | 0/3 |
| Intestine, small intestine | 0/3 |
| Intestine, colon | 0/3 |
| Intestine, rectum | 0/3 |
| Heart | 0/3 |
| kidney | 0/6 |
| Liver | 0/3 |
| Lung | 0/3 |
| Ovary | 0/3 |
| Pancreas | 0/3 |
| Parathyroid | 0/3 |
| Pituitary gland | 0/2 |
| Placenta | 1/3 |
| Prostate | 3/3 |
| Skin | 1/1 |
| Spinal Cord | 0/2 |
| Spleen | 0/2 |
| Skeletal Muscle | 0/3 |
| Testis | 0/3 |
| Thymus | 0/3 |
| Thyroid | 0/3 |
| Inflammatory Tonsillitis* | 3/3 |
| Ureter | 3/3 |
| Uterus cervix | 3/3 |
| Uterus endometrium | 0/3 |

*B-cells and T-cells are negative. Only normal squamous epithelium is positive.

Results of Western blots with mouse monoclonal anti-p40 antibody BC28

Figure 31:
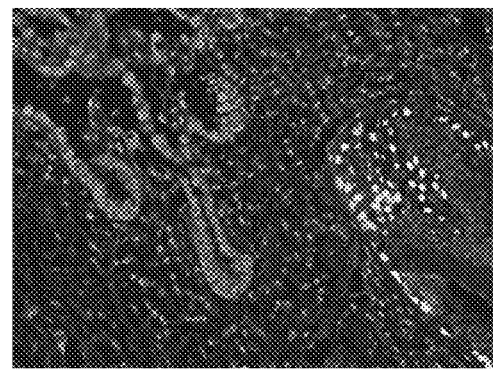
FIG. 31 shows a black and white version of an example of the antibody cocktail DSG-3+p40 [BC28]+Napsin A staining a specimen of lung adenocarcinoma. Staining of Napsin A (red) is cytoplasmic. Staining of DSG-3 (brown, membranous) and p40 (brown, nuclear) may be reduced, or perhaps restricted to normal lung tissue, in this sample.
Figure 32:
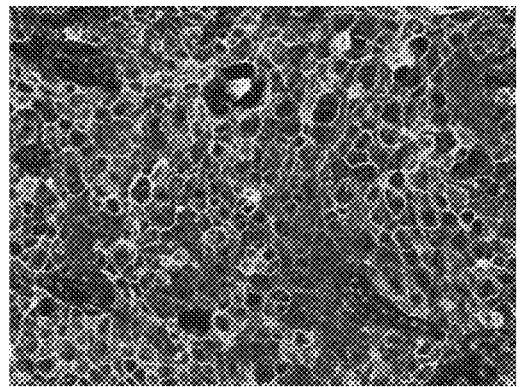
FIG. 32 shows a black and white version of an example of the antibody cocktail DSG-3+p40 [BC28]+Napsin A staining a specimen of lung squamous cell carcinoma. Staining of DSG-3 (brown) is membranous. Staining of p40 (brown, nuclear) and Napsin A (red, cytoplasmic) may be reduced, or perhaps absent, in this sample.
Figure 33:
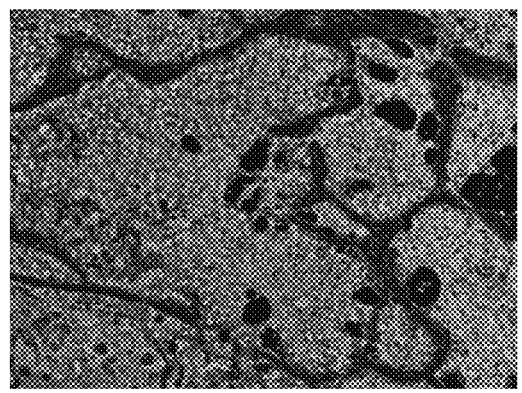
FIG. 33 shows a black and white version of an example of the antibody cocktail DSG-3+p40 [BC28]+Napsin A staining a specimen of lung squamous cell carcinoma. Staining of DSG-3 (brown) is membranous and staining of p40 (brown) in nuclear. Napsin A (red, cytoplasmic) may be reduced, or perhaps restricted to normal lung tissue, in this sample.
Figure 34:
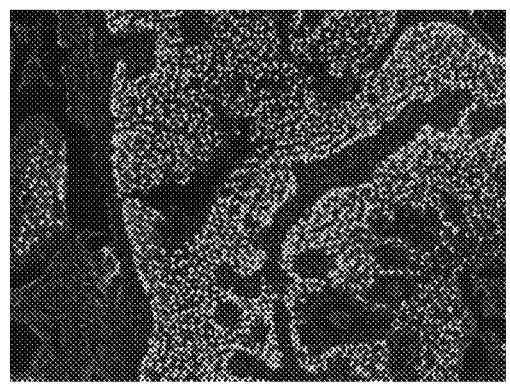
FIG. 34 shows a black and white version of an example of the antibody cocktail DSG-3+p40 [BC28]+Napsin A staining a specimen of lung squamous cell carcinoma. Staining of p40 (brown) in nuclear. Staining of DSG-3 (brown, membranous) and/or Napsin A (red, cytoplasmic) may be reduced, or perhaps absent, in this sample.

Binding of BC28 to p40 protein may be demonstrated by Western blot (FIG. 31, left panel, lane 2). The absence of similar binding of BC28 to TAp63 protein may also be shown by Western blot (FIGS. 48 and 98, left panel, lane 3). Conversely, the anti-p63 antibody 4A4 may bind both p40 protein and TAp63 protein (FIGS. 48 and 98, right panel, lanes 2 and 3). The greater specificity of BC28 (binding of p40, but not TAp63) may be an advantage that contributes to its superior properties.

In some embodiments of the present invention, anti-p40 antibodies such as the mouse monoclonal anti-p40 antibody BC28 may be suitable for use in many variations of the above protocols and other methods known to those in the art. Specimens stained with BC28 may be archived using a permanent mounting media and a coverslip. The antibody BC28 may also be used in an automated staining instrument, using standard protocols. One can also envision the use of many alternative detection methods (e.g., fluorescence), detection enzymes (e.g., alkaline phosphatase (AP), beta-galactosidase, or the like), and perhaps even chromogens (e.g., Fast Red, Fast Blue, 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide, or the like), generally known to those in the art.

An epitope of an anti-p40 antibody such as mouse monoclonal anti-p40 antibody, or a portion thereof, may be a useful antigen for the production of new monoclonal antibodies, including production in species other than mouse (e.g. rabbit, goat, horse, chicken, etc.) as one skilled in the art would understand.

While the use of anti-p40 antibodies such as BC28 in immunohistochemistry of formalin-fixed paraffin embedded tissues may be described here, its utility in other immunoassays may be readily envisioned and are meant to be included in this application. In particular, it may be well known that many of the same reagents used in IHC of FFPE may also be used in IHC of frozen-tissue sections. Anti-p40 antibodies such as BC28 may also be useful in other immunoassays, including ELISA, perhaps using generally known methods.

In another aspect of the invention, perhaps related to IHC, an anti-p40 antibody may be used in conjunction with one or more additional primary antibodies as part of a cocktail, to perform a "double-stain" procedure (also described as multi-stain or even multiplex). Such "double-stain" procedures may be generally well known in the art; however, the best combinations of primary antibodies for a particular diagnostic application may not be known.

In this method, anti-p40 antibodies such as a mouse monoclonal anti-p40 antibody BC28 could be combined with one or more antibodies in a single primary antibody cocktail, perhaps suitable for simultaneous application to a specimen. The antibodies may be derived from a mouse host or a rabbit host or the like. The antibodies may be monoclonal or polyclonal. In embodiments, an antibody cocktail may be used in a double-stain IHC procedure to produce two or more colored stains that may identify the presence or absence of target protein antigens in the tissue specimen. For example, in embodiments where an antibody cocktail may be comprised of mouse and rabbit antibodies, a detection system may include an anti-mouse antibody conjugated to horseradish peroxidase (HRP) and perhaps even an anti-rabbit antibody conjugated to alkaline phosphatase (AP) may be used to produce the two-color stain. 3,3'-diaminobenzidine (DAB) may be used to produce a brown stain, perhaps facilitated by HRP, and it may identify the presence or absence, and/or location, of mouse antibodies bound in the specimen; Fast Red may be used to produce a fuchsia/red stain, perhaps facilitated by AP, and it may identify the presence or absence, and/or location, of rabbit antibodies in the specimen. In other embodiments, a detection system may include an anti-mouse antibody conjugated to AP and an anti-rabbit antibody conjugated to HRP which may be used to produce a two-color stain that may identify the presence or absence, and/or location of the mouse antibodies with a red stain and the rabbit antibodies with a brown stain, perhaps when Fast Red and DAB may be used as chromogens. In some embodiments, an anti-mouse antibody conjugated to HRP and perhaps an anti-rabbit antibody conjugated to AP may be applied to the specimen as a cocktail, in a single solution, or they may be applied in separate, sequential steps.

The anti-mouse or anti-rabbit antibodies comprising the antibody-enzyme conjugates may be derived from a different host species, including, but not limited to mouse, rabbit, chicken, horse, rat, goat, sheep, or the like. A primary antibody may be from a variety of host species, including, but not limited to mouse, rabbit, chicken, horse, rat, goat, sheep, or the like. In embodiments, an antibody may include an antibody-enzyme conjugate and a primary antibody could be obtained from two different host species. Chromogens other than DAB and/or Fast Red may be used as well.

Multiple alternatives to a double-staining method are possible, including but not limited to the use of more than two antibodies, the use of species other than mouse and rabbit, other chromogens and detection systems, a different order of detection steps, and perhaps even modifications resulting in three or more colors (which may require a denaturing step).

Embodiments of the present invention may provide a composition having at least two antibodies or fragments thereof, perhaps as a cocktail, where at least one of the two antibodies or fragments thereof specifically binds to at least p40. This may provide a method for detecting at least two different proteins in a biological sample perhaps by contacting a biological sample with a composition comprising at least two antibodies or fragments thereof, where at least one of the at least two antibodies or fragments thereof may bind specifically to at least p40, to form an antigen-antibody complex and an antigen-antibody complex may be detected. A composition may have at least one first primary antibody and at least one second primary antibody.

At least one of the antibodies or fragments thereof may specifically bind to at least p40 and may even have a positive indication cut-off value of greater than 1% of stained cells. As mentioned herein, a positive indication cut-off value may provide a percentage of stained cells needed to indicate a positive staining result. Other cut-off value may include but are not limited to greater than about 1% of stained cells, greater than about 2% of stained cells, greater than about 3% of stained cells, greater than about 4% of stained cells, greater than about 5% of stained cells, greater than about 6% of stained cells, greater than about 7% of stained cells, greater than about 8% of stained cells, greater than about 9% of stained cells, and perhaps even greater than about 10% of stained cells, or more, or the like.

In embodiments, the present invention may provide a composition with at least two antibodies or fragments thereof which may be capable of providing different visualization results such as different color results. As discussed in other embodiments, below, a composition may provide that at least one other of an at least two antibodies or fragments thereof may bind specifically to DSG-3, CK4, Napsin A, HMWCK, p504s, CK5/14, CK7/18, CK8/18, Uroplakin II, Uroplakin III, GATA-3, and any combination thereof, or the like. Antibodies, compositions thereof, perhaps with anti-p40 antibodies may provide a detection system including but not limited to SCC carcinoma detection composition, bladder detection composition, breast carcinoma detection composition, prostate carcinoma detection composition, and any combination thereof, or the like.

In some embodiments, a single color stain may be used for a primary antibody cocktail. In one example, if the primary antibody cocktail is comprised of antibodies all derived from the same host species, then a single detection system may be used to stain for the presence of all of the antibodies with a single color. The presence or absence of each antibody may be determined based on cellular localization, or perhaps such determination is not necessary and the staining may be interpreted effectively without identifying the presence or absence of each antibody. For example, mouse monoclonal anti-p40 antibody BC28 may be combined with mouse monoclonal Desmoglein-3 (DSG-3) [BCH] in a primary antibody cocktail and used in an IHC procedure with anti-mouse conjugated HRP detection and DAB for visualization, to produce a brown stain. In another aspect, a primary antibody cocktail comprised of two or more antibodies from different host species may be used in a similar manner to produce a single color stain. For example, mouse monoclonal anti-p40 BC28 may be combined with rabbit monoclonal anti-CK20 antibody EPR1622Y and used in an IHC procedure with anti-mouse conjugated HRP and anti-rabbit conjugated HRP, and DAB for visualization, to produce a brown stain.

Certain steps of an IHC procedure may be performed sequentially or simultaneously, perhaps by using a cocktail of reagents, as known to those skilled in the art. For example, antibodies described in a primary antibody cocktail may alternatively be applied in sequential steps of one or more antibodies. Similarly, detection reagents may be applied simultaneously in reagent cocktail or separate reagents in sequential steps.

In some embodiments, a first primary antibody may be applied, followed by a first antibody-enzyme conjugate and first chromogen, and then a denaturing step, before proceeding to application of a second primary antibody, followed by a second antibody-enzyme conjugate and a second chromogen. In this manner, a double-stain of two different colors may be achieved using primary antibodies derived from the same species.

As well known to those in the art, certain steps of an IHC procedure may be performed sequentially or simultaneously, perhaps by using a cocktail of reagents, as known to those skilled in the art. For example, antibodies described in a primary antibody cocktail may alternatively be applied in sequential steps of one or more antibodies. Similarly, detection reagents may be applied simultaneously in reagent cocktail or separate reagents in sequential steps.

Antibodies that may be useful for diagnosis when combined with an anti-p40 antibody such as a mouse monoclonal anti-p40 antibody BC28 in a primary antibody cocktail for use in multi-stain procedures include:

| Antibody Combination and (Host Species) | Possible Staining Pattern (cellular localization, stain color*) | Possible Diagnostic Utility | Detection System Used in Example and FIG. No. |
| --- | --- | --- | --- |
| DSG-3 (Mouse) CK5 (Mouse) p40 [BC28] (Mouse) Napsin A (Rabbit) | DSG-3 (Membrane, Brown) CK5 (Cytoplasmic, Brown) p40 (Nuclear, Brown) Napsin A (Cytoplasmic, Red) | DSG-3 and/or CK5 and/or p40 staining may be observed in lung SCC; Napsin A staining may be observed in lung ADC | DS#2 FIGS. 26, 27, 76, 77 |
| DSG-3 (Mouse) CK5 (Mouse) p40 [BC28] (Mouse) | DSG-3 (Membrane, Brown) CK5 (Cytoplasmic, Brown) p40 (Nuclear, Brown) | DSG-3 and/or CK5 and/or p40 staining may be observed in lung SCC | Goat anti-mouse-HRP FIGS. 28, 29, 78, 79 |
| DSG-3 (Mouse) p40 [BC28] (Mouse) Napsin A (Rabbit) | DSG-3 (Membrane, Brown) p40 (M) (Nuclear, Brown) Napsin A (Cytoplasmic, Red) | DSG-3 and/or p40 staining may be observed in SCC; Napsin A staining may be observed in ADC. | DS#2 FIGS. 30-34 and 80-84 |
| DSG-3 (Mouse) p40 [BC28] (Mouse) | DSG-3 (Membrane, Brown) p40 (Nuclear, Brown) | DSG-3 and/or p40 staining may be observed in lung SCC | Goat anti-mouse-HRP FIGS. 35, 85 |
| p40 [BC28] (Mouse) CK5 (Rabbit) | p40 (Nuclear, Brown) CK5 (Cytoplasmic, Red) | CK5 and/or p40 staining may be observed in SCC. | DS#2 FIGS. 36, 37, 86, 87 |
| p40 [BC28] (Mouse) Napsin A (Rabbit) | p40 (Nuclear, Brown) Napsin A (Cytoplasmic, Red) | p40 staining may be observed in lung SCC; Napsin A staining may be observed in lung ADC | DS#2 FIGS. 38, 39, 88, 89 |
| p40 [BC28] (Mouse) HMWCK (Mouse) P504S (Rabbit) | p40 [BC28] (Nuclear, Brown) HMWCK (Cytoplasmic, Brown) P504S (Cytoplasmic, Red) | p40 and/or HMWCK staining may be decreased, or perhaps absent, in prostate cancer P504S staining may be observed in prostate cancer | DS#2 FIGS. 40, 90 |
| p40 [BC28] (Mouse) CK5/14 (Mouse) P504S (Rabbit) | p40 [BC28] (Nuclear, Brown) CK5/14 (Cytoplasmic, Brown) P504S (Cytoplasmic, Red) | p40 and/or CK5/14 staining may be decreased, or perhaps absent, in prostate cancer P504S staining may be observed in prostate cancer | DS#2 FIGS. 41, 91 |
| p40 [BC28] (Mouse) CK5/14 (Mouse) CK7/18 (Rabbit) | p40 [BC28] (Nuclear, Brown) CK5/14 (Cytoplasmic, Brown) CK7/18 (Cytoplasmic, Red) | Staining pattern may be useful to identify breast lesions, such as carcinoma in situ and perhaps distinguish benign from neoplastic lesions | DS#2 FIGS. 42, 43, 92, 93 |

Figure 44:
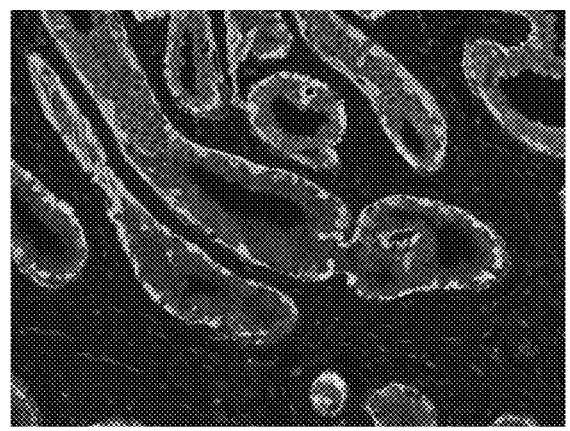
FIG. 44 shows a black and white version of an example of an antibody cocktail of p40 [BC28]+CK5/14+CK8/18 staining a specimen of breast tissue, perhaps abnormal tissue, or perhaps even breast cancer. Staining of p40 (brown) is nuclear and perhaps reduced, or absent, in this sample. Staining of CK5/14 (brown) and CK8/18 (red) is cytoplasmic.
Figure 45:
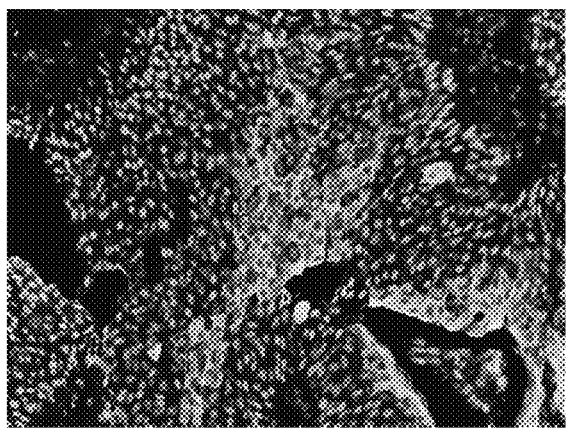
FIG. 45 shows a black and white version of an example of an antibody cocktail of p40 [BC28]+Uroplakin II+Uroplakin III staining a specimen of urothelial carcinoma. Staining of p40 (brown) is nuclear. Staining of Uroplakin II (brown) and Uroplakin III (brown) is cytoplasmic and membranous.
Figure 46:
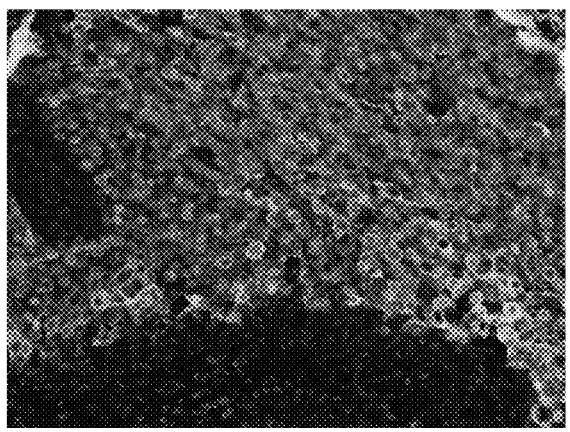
FIG. 46 shows a black and white version of an example of an antibody cocktail of p40 [BC28]+Uroplakin II+Uroplakin III+GATA-3 staining a specimen of urothelial carcinoma. Staining of p40 (brown) and GATA-3 (red) is nuclear. Staining of Uroplakin II (brown) and Uroplakin III (brown) is cytoplasmic and membranous.
Figure 47:
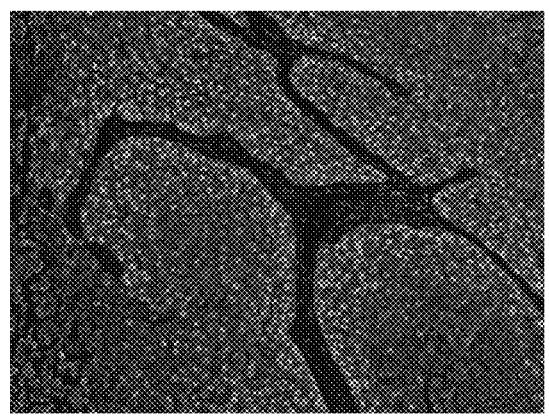
FIG. 47 shows a black and white version of an example of an antibody cocktail of p40 [BC28]+CK5 staining a specimen of lung squamous cell carcinoma. Staining of p40 (brown) is nuclear and staining of CK5 (brown) is cytoplasmic.
Figure 94:
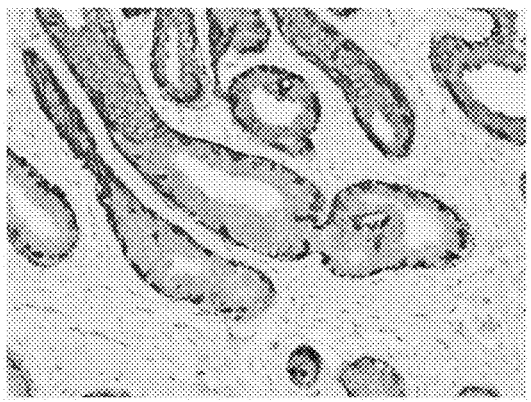
FIG. 94 shows the color version of FIG. 44 of an example of an antibody cocktail of p40 [BC28]+CK5/14+CK8/18 staining a specimen of breast tissue, perhaps abnormal tissue, or perhaps even breast cancer. Staining of p40 (brown) is nuclear and perhaps reduced, or absent, in this sample. Staining of CK5/14 (brown) and CK8/18 (red) is cytoplasmic.
Figure 95:
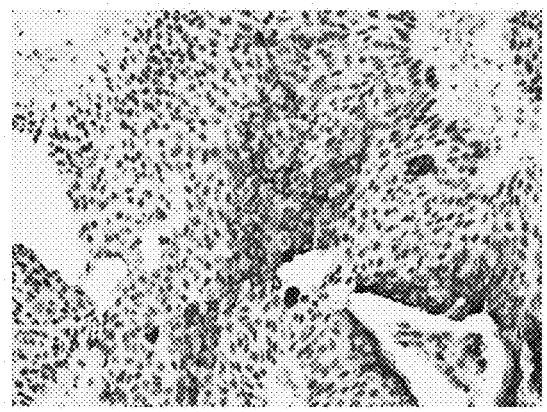
FIG. 95 shows the color version of FIG. 45 of an example of an antibody cocktail of p40 [BC28]+Uroplakin II+Uroplakin III staining a specimen of urothelial carcinoma. Staining of p40 (brown) is nuclear. Staining of Uroplakin II (brown) and Uroplakin III (brown) is cytoplasmic and membranous.
Figure 96:
FIG. 96 shows the color version of FIG. 46 of an example of an antibody cocktail of p40 [BC28]+Uroplakin II+Uroplakin III+GATA-3 staining a specimen of urothelial carcinoma. Staining of p40 (brown) and GATA-3 (red) is nuclear. Staining of Uroplakin II (brown) and Uroplakin III (brown) is cytoplasmic and membranous.
Figure 97:
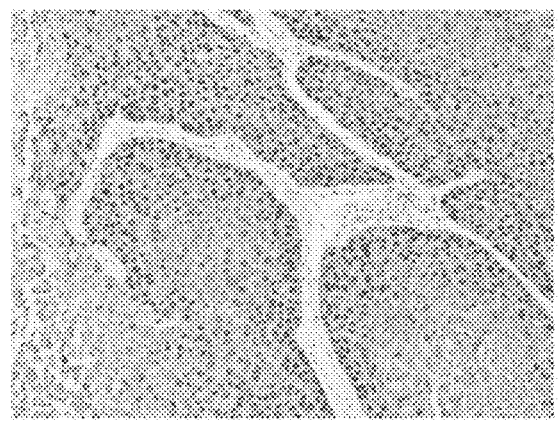
FIG. 97 shows the color version of FIG. 47 of an example of an antibody cocktail of p40 [BC28]+CK5 staining a specimen of lung squamous cell carcinoma. Staining of p40 (brown) is nuclear and staining of CK5 (brown) is cytoplasmic.

| Antibody Combination and (Host Species) | Possible Staining Pattern (cellular localization, stain color*) | Possible Diagnostic Utility | Detection System Used in Example and FIG. No. |
|---|---|---|---|
| p40 [BC28] (Mouse) CK5/14 (Mouse) CK8/18 (Rabbit) | p40 [BC28] (Nuclear, Brown) CK5/14 (Cytoplasmic, Brown) CK8/18 (Cytoplasmic, Red) | Staining pattern may be useful to identify breast lesions, such as carcinoma in situ and perhaps distinguish benign from neoplastic lesions | DS#2 FIGS. 44, 94 |
| p40 [BC28] (Mouse) and/or Uroplakin II [BC21] (Mouse) and/or Uroplakin III [BC17] (Mouse) | p40 [BC28] (Nuclear, Brown) Uroplakin II (Membrane and cytoplasmic, Brown) Uroplakin III (Membrane and cytoplasmic, Brown) | p40 and/or Uroplakin II and/or Uroplakin III staining may be observed in bladder cancer. | Goat anti-mouse-HRP FIGS. 45, 95 |
| p40 [BC28] (Mouse) and/or Uroplakin II [BC21] (Mouse) and/or Uroplakin III [BC17] (Mouse) and/or GATA-3 (Rabbit) | p40 [BC28] (Nuclear, Brown) Uroplakin II (Membrane and cytoplasmic, Brown) Uroplakin III (Membrane and cytoplasmic, Brown) GATA-3 (Nuclear, Red) | p40 and/or Uroplakin II and/or Uroplakin III and/or GATA-3 staining may be observed in bladder cancer. | DS#2 FIGS. 46, 96 |
| p40 [BC28] (Mouse) CK5 (Mouse) | p40 (Nuclear, Brown) CK5 (Cytoplasmic, Brown) | CK5 and/or p40 staining may be observed in SCC. | Goat anti-mouse-HRP FIGS. 47, 97 |

*The listed color of each stain may be a result of a detection system that may include an anti-mouse antibody perhaps conjugated to HRP and even an anti-rabbit antibody perhaps conjugated to AP, perhaps even with DAB and Fast Red as chromogens, which may result in brown staining for mouse antibodies and red staining for rabbit antibodies (referred to as DS#2). Alternatively, the detection system may include an anti-mouse antibody perhaps conjugated to AP and even an anti-rabbit antibody perhaps conjugated to HRP, perhaps even with DAB and Fast Red as chromogens, which may result in red staining for mouse antibodies and brown staining for rabbit antibodies (referred to as DS#1). In some instances, two colors may not be necessary because the antigens may be distinguished by cellular localization of staining, or perhaps it is not diagnostically significant to determine which antigen is staining. Other color combinations may be obtained using other detection systems or chromogens and all are meant to be included in this disclosure.

Other examples cocktails may be provided in PCT patent application no. PCT/US2013/076203, filed Dec. 18, 2013, entitled "Antibody Cocktail Systems and Methods for Classification of Histologic Subtypes in Lung Cancer," hereby incorporated by reference herein.

IHC double-stain method with an antibody cocktail of DSG-3, CK5, p40 [BC28] and Napsin A: Immunohistochemistry, perhaps to produce a "double-stain" or a "multiplex procedure," using antibody cocktails such as DSG-3+CK5+p40 [BC28]+Napsin A may be performed on formalin-fixed paraffin embedded (FFPE) tissue samples using procedures generally known to those in the art, as generally exemplified by the following non-limiting examples (e.g., washes with Tris-buffered saline, pH about 7.6, between steps):

1) Sections (~5 μm) of formalin fixed paraffin-embedded tissues may be mounted on commercially available microscope slides perhaps coated with polylysine.
2) Sections may be deparaffinized (using xylenes or a xylene-substitute) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Diva, Decloaking Chamber; Biocare Medical) and may be heated to about 125° C. for about 30 seconds. [Other antigen retrieval methods known to those skilled in the art (e.g., steamer, microwave oven, enzyme, or the like) may also be acceptable.] Tissues may be allowed to cool for about 10 minutes and then may be rinsed with deionized water.
4) The antibody cocktail of DSG-3+CK5+p40 [BC28]+Napsin A may be applied in a phosphate-buffered solution (pH about 6.0) with bovine serum albumin as carrier protein for about 30 minutes.
5) Detection of the antibodies perhaps with a cocktail of goat anti-mouse horseradish peroxidase (HRP) conjugated secondary antibody and goat anti-rabbit alkaline phosphatase (AP) conjugated secondary antibody (MACH 2 Double Stain #2, Biocare Medical) with an incubation of about 30 minutes.
6) In perhaps a final detection step, Fast Red chromogen with naphthol phosphate substrate, perhaps in a buffer of about pH 8.3 (Vulcan Fast Red, Biocare Medical) may be applied for about 20 minutes, which may produce a fuschia/red chromogenic product as a stain. Subsequently, 3,3'-diaminobenzidine (DAB) in buffer perhaps containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of the sites of antigen expression for each antibody. The presence of p40, DSG-3 and CK5 antibodies may be determined by brown staining. The presence of Napsin A antibodies may be determined by red staining.
7) Slides may be briefly counterstained perhaps in a modified Mayer's hematoxylin.

IHC single-stain method with an antibody cocktail of DSG-3, CK5 and p40 [BC28]: Immunohistochemistry using an antibody cocktail such as DSG-3+CK5+p40 [BC28] may be performed on formalin-fixed paraffin embedded (FFPE) tissue samples using procedures generally known to those in the art, as generally exemplified by the following non-limiting examples (e.g., washes with Tris-buffered saline, pH about 7.6, between steps):
1) Sections (~5 µm) of formalin fixed paraffin-embedded tissues may be mounted on commercially available microscope slides perhaps coated with polylysine.
2) Sections may be deparaffinized (using xylenes or a xylene-substitute) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Diva, Decloaking Chamber; Biocare Medical) and may be heated to about 125° C. for about 30 seconds. [Other antigen retrieval methods known to those skilled in the art (e.g., steamer, microwave oven, enzyme, or the like) may also be acceptable.] Tissues may be allowed to cool for about 10 minutes and then may be rinsed with deionized water.
4) The antibody cocktail of DSG-3+CK5+p40 [BC28] may be applied in a phosphate-buffered solution (pH about 6.0) with bovine serum albumin as carrier protein for about 30 minutes.
5) Detection of the antibodies perhaps with a cocktail of goat anti-mouse horseradish peroxidase (HRP) conjugated secondary antibody (MACH 2 Mouse-HRP Polymer Detection, Biocare Medical) with an incubation of about 30 minutes. Alternatively, detection of the anbtibodies perhaps with a horseradish peroxidase (HRP) conjugated secondary antibody (MACH 4 Universal HRP-Polymer Detection, Biocare Medical) may be accomplished in two steps. An initial application of a rabbit anti-mouse IgG antibody for about 10 minutes may be followed by incubation with a goat anti-rabbit-HRP conjugate for about 10 minutes.
6) In perhaps a final detection step, 3,3'-diaminobenzidine (DAB) in buffer perhaps containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of the sites of antigen expression for each antibody. The presence of p40, DSG-3 and CK5 antibodies may be determined by brown staining.
7) Slides may be briefly counterstained perhaps in a modified Mayer's hematoxylin.

Figure 26:
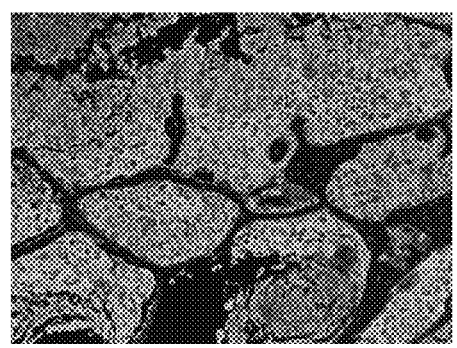
FIG. 26 shows a black and white version of an example of DSG-3+CK5+p40 [BC28]+Napsin A staining a specimen of lung squamous cell carcinoma. Staining of DSG-3 (brown) is membranous; staining of CK5 (brown) is cytoplasmic; staining of p40 (brown) is nuclear. Staining of Napsin A may be reduced, or perhaps restricted to residual normal lung in this specimen.
Figure 27:
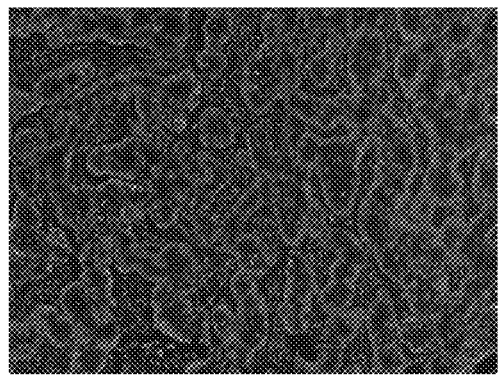
FIG. 27 shows a black and white version of an example of DSG-3+CK5+p40 [BC28]+Napsin A staining a specimen of lung adenocarcinoma. Staining of Napsin A (red) is cytoplasmic. Staining of DSG-3, CK5 and p40 (brown) may be reduced, or perhaps absent, in this sample.
Figure 76:
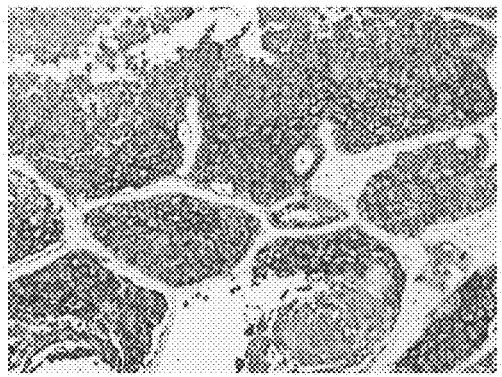
FIG. 76 shows the color version of FIG. 26 of an example of DSG-3+CK5+p40 [BC28]+Napsin A staining a specimen of lung squamous cell carcinoma. Staining of DSG-3 (brown) is membranous; staining of CK5 (brown) is cytoplasmic; staining of p40 (brown) is nuclear. Staining of Napsin A may be reduced, or perhaps restricted to residual normal lung in this specimen.
Figure 77:
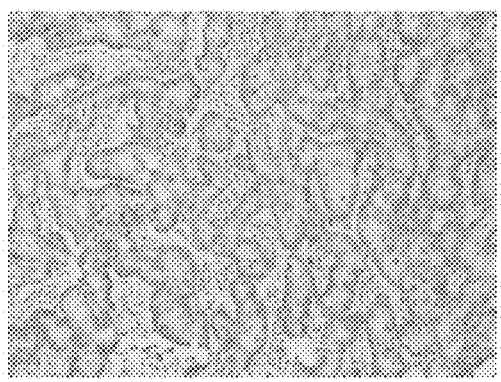
FIG. 77 shows the color version of FIG. 27 of an example of DSG-3+CK5+p40 [BC28]+Napsin A staining a specimen of lung adenocarcinoma. Staining of Napsin A (red) is cytoplasmic. Staining of DSG-3, CK5 and p40 (brown) may be reduced, or perhaps absent, in this sample.

Results of IHC Staining with DSG-3, CK5, p40 [BC28] and Napsin A: Using the above double-stain protocol, FFPE tissues may be stained with a cocktail of DSG-3, p40 [BC28], CK5 and Napsin A. An example of staining of lung SCC is shown in FIGS. 26 and 76. The presence of DSG-3, p40, and/or CK5 antibodies may result in brown staining. Red staining of Napsin A may be reduced or absent, or perhaps restricted to residual normal lung tissue. An example of staining of lung ADC is shown in FIGS. 27 and 77. The presence of Napsin A may result in the red staining. Brown staining from p40, DSG-3, and/or CK5 may be reduced, or absent (e.g., see FIGS. 27 and 77).

Figure 28:
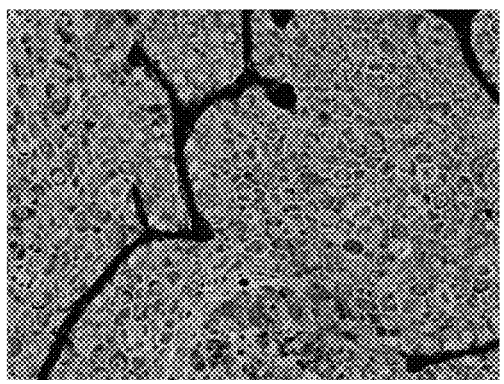
FIG. 28 shows a black and white version of an example of DSG-3+CK5+p40 [BC28]+staining a specimen of lung squamous cell carcinoma. Staining of DSG-3 (brown) is membranous; staining of CK5 (brown) is cytoplasmic; staining of p40 (brown) is nuclear.
Figure 29:
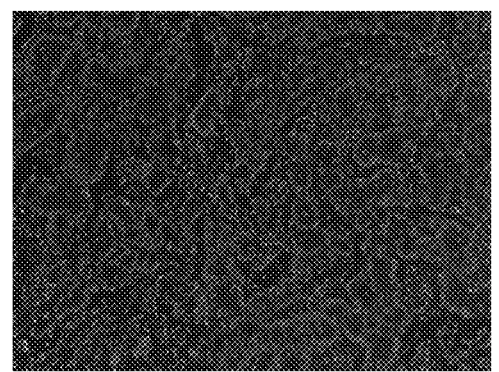
FIG. 29 shows a black and white version of an example of DSG-3+CK5+p40 [BC28] staining a specimen of lung adenocarcinoma. Staining of DSG-3, CK5 and p40 (brown) may be reduced, or perhaps absent, in this sample.
Figure 30:
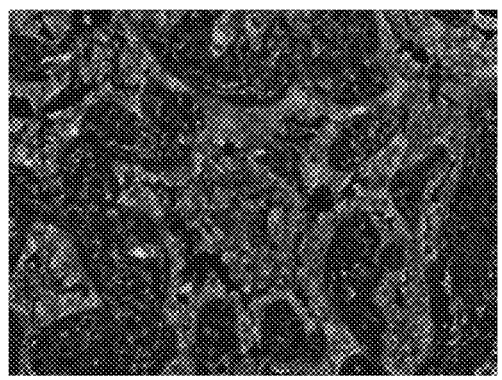
FIG. 30 shows a black and white version of an example of the antibody cocktail DSG-3+p40 [BC28]+Napsin A staining a specimen of lung adenocarcinoma. Staining of Napsin A (red) is cytoplasmic. Staining of DSG-3 (brown, membranous) and p40 (brown, nuclear) may be reduced, or perhaps absent, in this sample.
Figure 78:
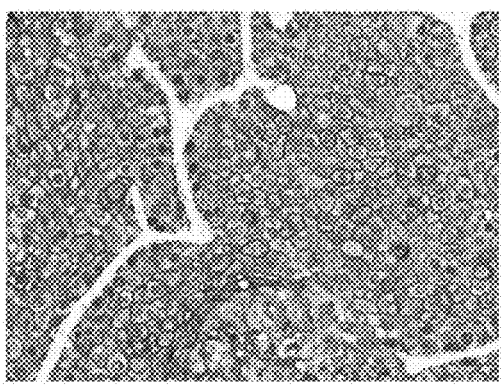
FIG. 78 shows the color version of FIG. 28 of an example of DSG-3+CK5+p40 [BC28] staining a specimen of lung squamous cell carcinoma. Staining of DSG-3 (brown) is membranous; staining of CK5 (brown) is cytoplasmic; staining of p40 (brown) is nuclear.
Figure 79:
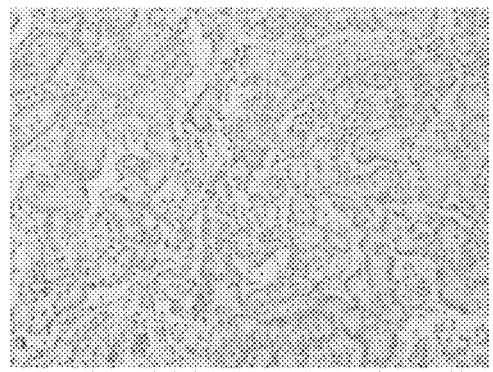
FIG. 79 shows the color version of FIG. 29 of an example of DSG-3+CK5+p40 [BC28] staining a specimen of lung adenocarcinoma. Staining of DSG-3, CK5 and p40 (brown) may be reduced, or perhaps absent, in this sample.
Figure 80:
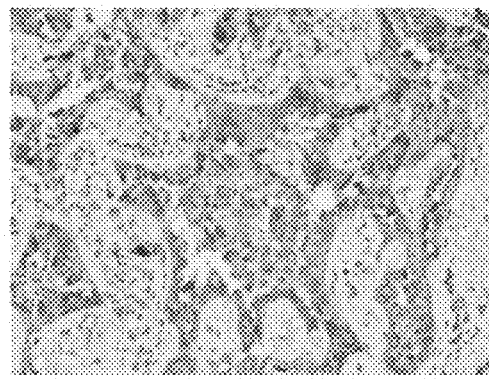
FIG. 80 shows the color version of FIG. 30 of an example of the antibody cocktail DSG-3+p40 [BC28]+Napsin A staining a specimen of lung adenocarcinoma. Staining of Napsin A (red) is cytoplasmic. Staining of DSG-3 (brown, membranous) and p40 (brown, nuclear) may be reduced, or perhaps absent, in this sample.
Figure 81:
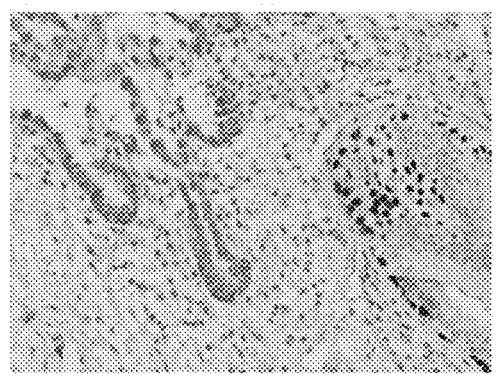
FIG. 81 shows the color version of FIG. 31 of an example of the antibody cocktail DSG-3+p40 [BC28]+Napsin A staining a specimen of lung adenocarcinoma. Staining of Napsin A (red) is cytoplasmic. Staining of DSG-3 (brown, membranous) and p40 (brown, nuclear) may be reduced, or perhaps restricted to normal lung tissue, in this sample.
Figure 82:
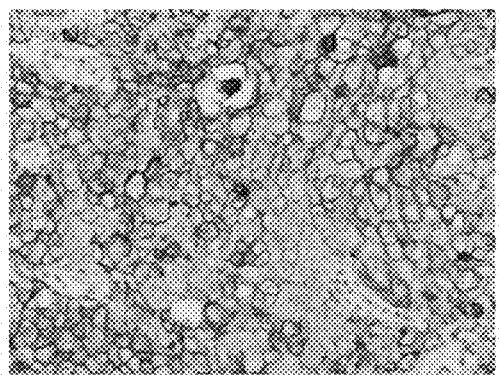
FIG. 82 shows the color version of FIG. 32 of an example of the antibody cocktail DSG-3+p40 [BC28]+Napsin A staining a specimen of lung squamous cell carcinoma. Staining of DSG-3 (brown) is membranous. Staining of p40 (brown, nuclear) and Napsin A (red, cytoplasmic) may be reduced, or perhaps absent, in this sample.
Figure 83:
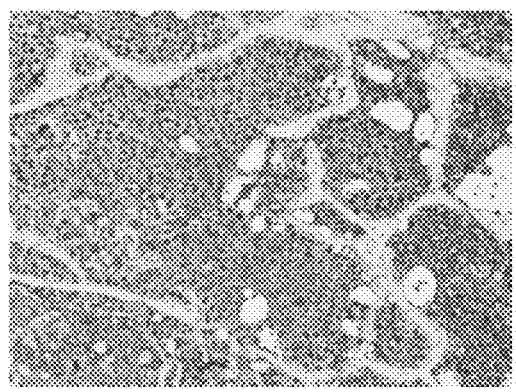
FIG. 83 shows the color version of FIG. 33 of an example of the antibody cocktail DSG-3+p40 [BC28]+Napsin A staining a specimen of lung squamous cell carcinoma. Staining of DSG-3 (brown) is membranous and staining of p40 (brown) in nuclear. Napsin A (red, cytoplasmic) may be reduced, or perhaps restricted to normal lung tissue, in this sample.
Figure 84:
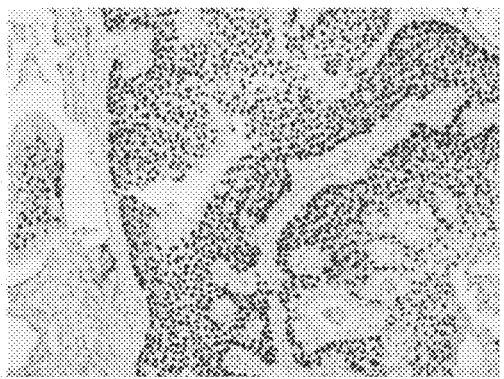
FIG. 84 shows the color version of FIG. 34 of an example of the antibody cocktail DSG-3+p40 [BC28]+Napsin A staining a specimen of lung squamous cell carcinoma. Staining of p40 (brown) in nuclear. Staining of DSG-3 (brown, membranous) and/or Napsin A (red, cytoplasmic) may be reduced, or perhaps absent, in this sample.

Results of IHC Staining with DSG-3, CK5, and p40 [BC28]: Using the above single-stain protocol, FFPE tissues may be stained with a cocktail of DSG-3, p40 [BC28], and CK5. An example of staining of lung SCC is shown in FIGS. 28 and 78. The presence of DSG-3, p40, and/or CK5 antibodies may result in brown staining. In this example, using a single-color stain for detection, such as goat anti-mouse HRP, is acceptable because the presence of DSG-3, p40, or CK5 all are indicative of squamous cell carcinoma. An example of staining of lung ADC is shown in FIGS. 29 and 79. Brown staining from DSG-3, p40, and/or CK5 may be reduced, or absent (e.g., see FIGS. 29 and 79), or even restricted to residual normal lung tissue.

Results of IHC Staining with DSG-3, p40 (M) and Napsin A: Using the above double-stain protocol, FFPE tissues may be stained with a cocktail of DSG-3, p40 (M) (e.g., mouse monoclonal [BC28]) and Napsin A. Examples of staining of ADC are shown in FIGS. 20A and 20B. The presence of Napsin A may result in the red staining. Brown staining from p40 or DSG-3 may be reduced, or absent (e.g., see FIGS. 30, 80, 31 and 81), or even restricted to residual normal lung tissue (e.g., see FIGS. 31 and 81). Examples of staining of SCC are shown in FIGS. 32, 82, 33, 83, 34, and 84. The presence of DSG-3 or p40 antibodies may result in brown staining. Red staining of Napsin A may be reduced or absent, or perhaps restricted to residual normal lung tissue (e.g., see FIGS. 33 and 83).

Figure 35:
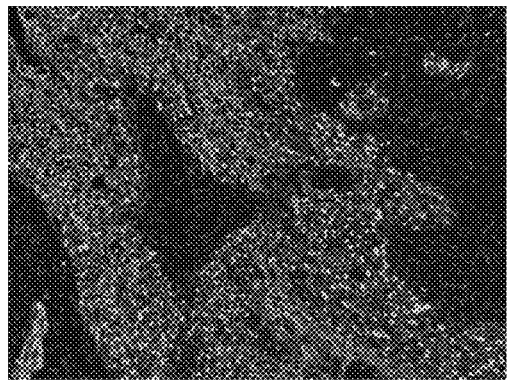
FIG. 35 shows a black and white version of an example of the antibody cocktail DSG-3+p40 [BC28] staining a specimen of lung squamous cell carcinoma. Staining of DSG-3 (brown) is membranous and staining of p40 (brown) in nuclear.
Figure 85:
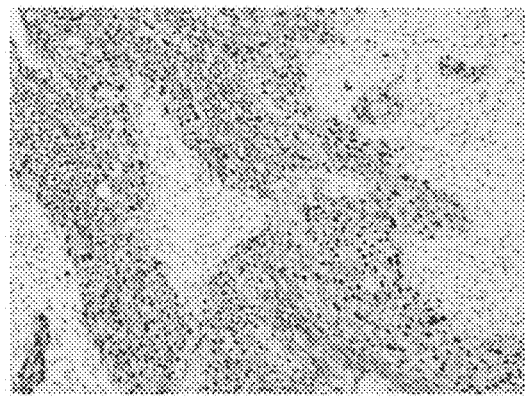
FIG. 85 shows the color version of FIG. 35 of an example of the antibody cocktail DSG-3+p40 [BC28] staining a specimen of lung squamous cell carcinoma. Staining of DSG-3 (brown) is membranous and staining of p40 (brown) in nuclear.

Results of IHC Staining with DSG-3 and p40 (M): Using the above single-stain protocol, with a detection system of goat anti-mouse HRP, FFPE tissues may be stained with a cocktail of DSG-3 and p40 (M). An example of staining of SCC is shown in FIGS. 35 and 85. The presence of DSG-3 and/or CK5 antibodies may result in the brown staining.

Figure 36:
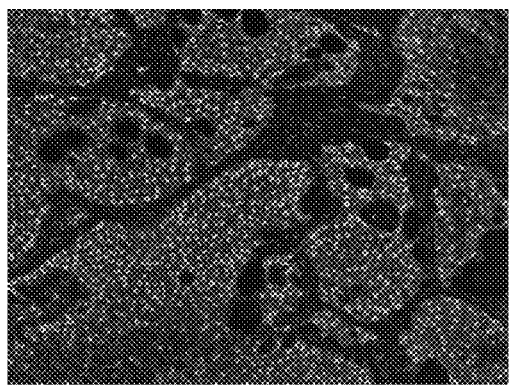
FIG. 36 shows a black and white version of an example of the antibody cocktail p40 [BC28]+CK5 (RM) staining a specimen of lung squamous cell carcinoma. Staining of p40 (brown) is nuclear and staining of CK5 (red) is cytoplasmic.
Figure 37:
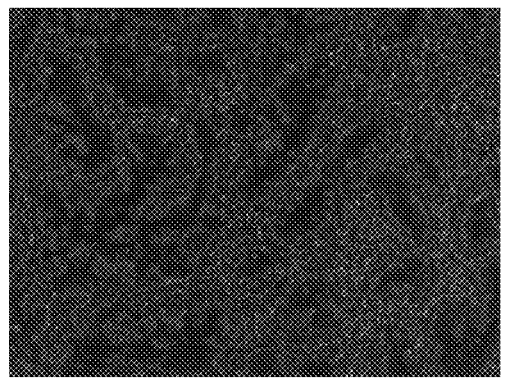
FIG. 37 shows a black and white version of an example of the antibody cocktail p40 [BC28]+CK5 (RM) staining a specimen of lung adenocarcinoma. Staining of p40 (brown, nuclear) and CK5 (red, cytoplasmic) may be reduced, or perhaps absent, in this sample.
Figure 86:
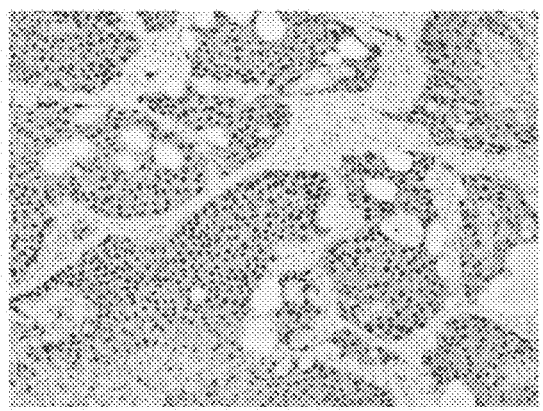
FIG. 86 shows the color version of FIG. 36 of an example of the antibody cocktail p40 [BC28]+CK5 (RM) staining a specimen of lung squamous cell carcinoma. Staining of p40 (brown) is nuclear and staining of CK5 (red) is cytoplasmic.
Figure 87:
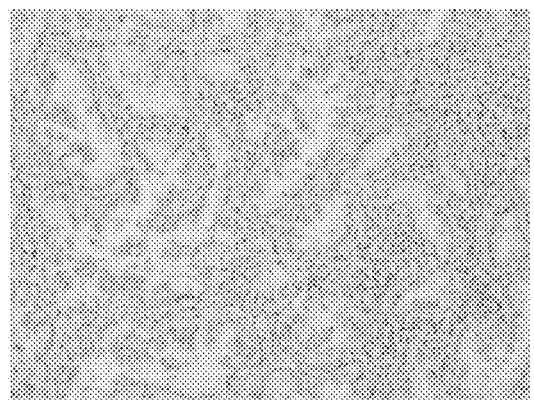
FIG. 87 shows the color version of FIG. 37 of an example of the antibody cocktail p40 [BC28]+CK5 (RM) staining a specimen of lung adenocarcinoma. Staining of p40 (brown, nuclear) and CK5 (red, cytoplasmic) may be reduced, or perhaps absent, in this sample.

Results of IHC Staining with p40 (M) and CK5 (RM): Using the above double-stain protocol, FFPE tissues may be stained with a cocktail of p40 [BC28] and CK5 (RM) (e.g., rabbit monoclonal [EP1601Y]). An example of staining of lung SCC is shown in FIGS. 36 and 86. The presence of p40 (M) antibodies may result in the brown staining and the presence of CK5 (RM) antibodies results in the red staining. An example of staining of lung ADC is shown in FIGS. 37 and 87. No brown or red staining may be observed, suggesting perhaps the absence of p40 and CK5.

Figure 38:
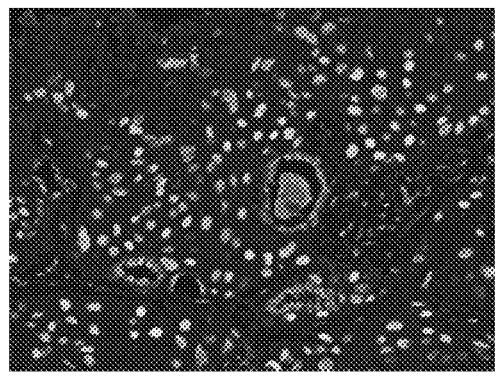
FIG. 38 shows a black and white version of an example of the antibody cocktail of p40 [BC28]+Napsin A staining a specimen of lung squamous cell carcinoma. Staining of p40 (brown) in nuclear. Napsin A (red, cytoplasmic) may be reduced, or perhaps restricted to normal lung tissue, in this sample.
Figure 39:
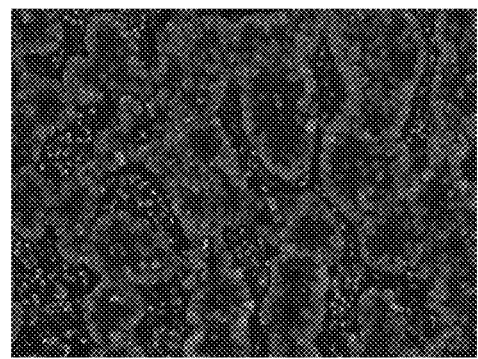
FIG. 39 shows a black and white version of an example of the antibody cocktail of p40 [BC28]+Napsin A staining a specimen of lung adenocarcinoma. Staining of Napsin A (red) is cytoplasmic. Staining of p40 (brown, nuclear) may be reduced, or perhaps absent, in this sample.
Figure 88:
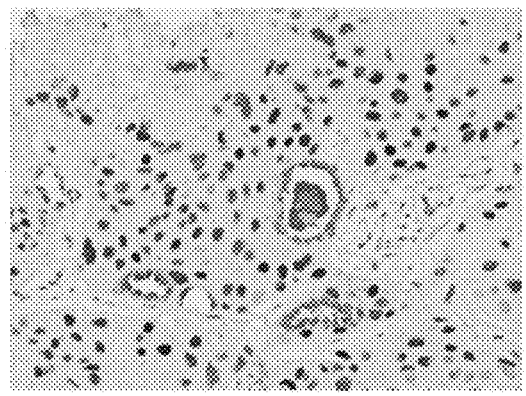
FIG. 88 shows the color version of FIG. 38 of an example of the antibody cocktail of p40 [BC28]+Napsin A staining a specimen of lung squamous cell carcinoma. Staining of p40 (brown) in nuclear. Napsin A (red, cytoplasmic) may be reduced, or perhaps restricted to normal lung tissue, in this sample.
Figure 89:
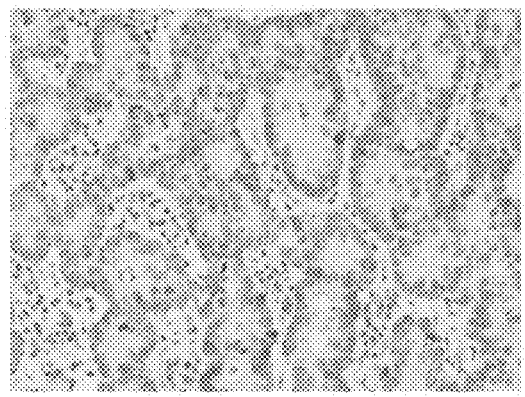
FIG. 89 shows the color version of FIG. 39 of an example of the antibody cocktail of p40 [BC28]+Napsin A staining a specimen of lung adenocarcinoma. Staining of Napsin A (red) is cytoplasmic. Staining of p40 (brown, nuclear) may be reduced, or perhaps absent, in this sample.

Results of IHC Staining with p40 (M) and Napsin A: Using the above double-stain protocol, FFPE tissues may be stained with a cocktail of p40 (M) (e.g., mouse monoclonal [BC28]) and Napsin A. An example of staining of SCC is shown in FIGS. 38 and 88. The presence of p40 antibodies may result in brown staining. Red staining of Napsin A may be reduced or absent, or perhaps restricted to residual normal lung tissue. An example of staining of ADC is shown in FIGS. 39 and 89. The presence of Napsin A may result in the red staining. Brown staining from p40 may be reduced, or absent.

Figure 40:
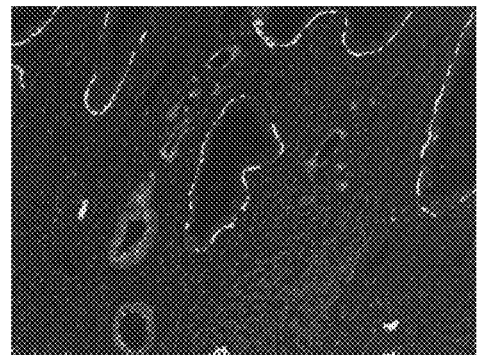
FIG. 40 shows a black and white version of an example of an antibody cocktail of p40 [BC28]+HMWCK+P504S staining a specimen of prostate, which may contain areas of perhaps normal prostate, perhaps prostatic adenocarcinoma and perhaps even prostatic intraepithelial neoplasia (PIN). Staining of p40 (brown) is nuclear. Staining of HMWCK (brown) is cytoplasmic. Staining of P504S (red) is cytoplasmic, and perhaps granular.
Figure 90:
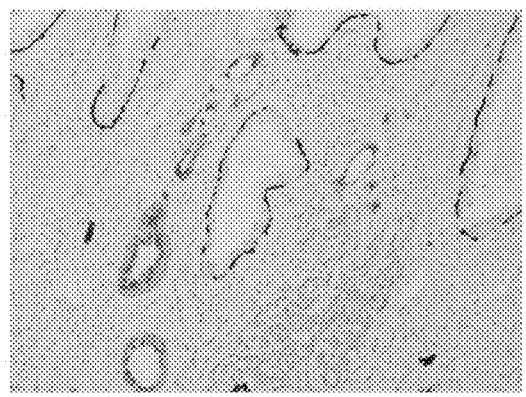
FIG. 90 shows the color version of FIG. 40 of an example of an antibody cocktail of p40 [BC28]+HMWCK+P504S staining a specimen of prostate, which may contain areas of perhaps normal prostate, perhaps prostatic adenocarcinoma and perhaps even prostatic intraepithelial neoplasia (PIN). Staining of p40 (brown) is nuclear. Staining of HMWCK (brown) is cytoplasmic. Staining of P504S (red) is cytoplasmic, and perhaps granular.

Results of IHC Staining with p40 [BC28], HMWCK, and P504S: Using the above double-stain protocol, FFPE tissues may be stained with a cocktail of p40 [BC28], HMWCK (e.g. mouse monoclonal clone 34(3E12), and P504S (perhaps also known as AMACR, e.g. rabbit monoclonal anti-AMACR [13H4], or a rabbit polyclonal antibody). An example of staining of prostate tissue is shown in FIGS. 40 and 90. The presence of p40 and or HMWCK antibodies may result in brown staining. The presence of P504S antibodies may result in red staining. The tissue may contain normal prostate glands, areas of prostate cancer, or perhaps prostatic intraepithelial neoplasia (PIN).

Figure 41:
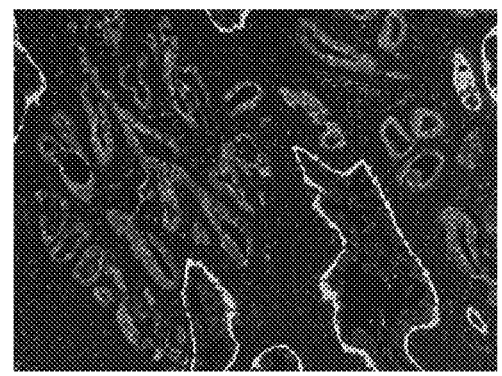
FIG. 41 shows a black and white version of an example of an antibody cocktail of p40 [BC28]+CK5/14+P504S staining a specimen of prostate, which may contain areas of perhaps normal prostate, perhaps prostatic adenocarcinoma and perhaps even prostatic intraepithelial neoplasia (PIN). Staining of p40 (brown) is nuclear. Staining of CK5/14 (brown) is cytoplasmic. Staining of P504S (red) is cytoplasmic, and perhaps granular.
Figure 42:
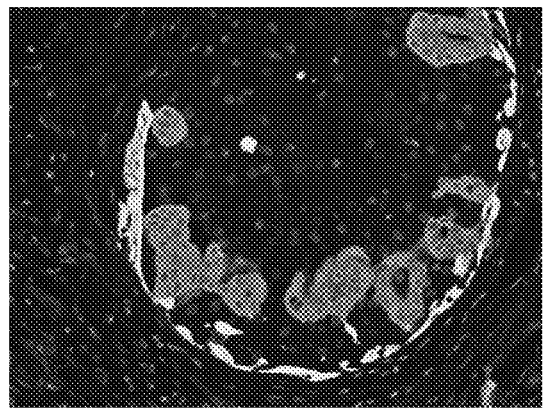
FIG. 42 shows a black and white version of an example of an antibody cocktail of p40 [BC28]+CK5/14+CK7/18 staining a specimen of breast tissue, perhaps abnormal tissue, or perhaps even breast cancer. Staining of p40 (brown) is nuclear. Staining of CK5/14 (brown) is cytoplasmic. Staining of CK7/18 (red) is cytoplasmic.
Figure 91:
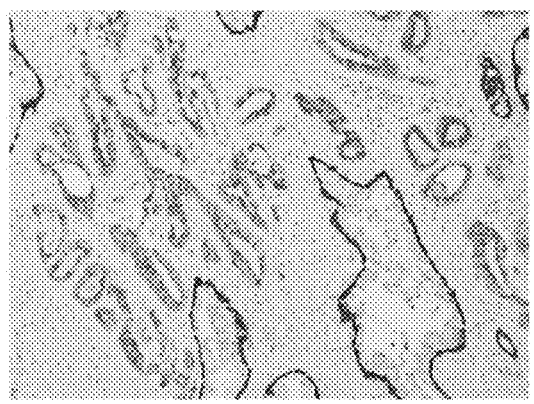
FIG. 91 shows the color version of FIG. 41 of an example of an antibody cocktail of p40 [BC28]+CK5/14+P504S staining a specimen of prostate, which may contain areas of perhaps normal prostate, perhaps prostatic adenocarcinoma and perhaps even prostatic intraepithelial neoplasia (PIN). Staining of p40 (brown) is nuclear. Staining of CK5/14 (brown) is cytoplasmic. Staining of P504S (red) is cytoplasmic, and perhaps granular.
Figure 92:
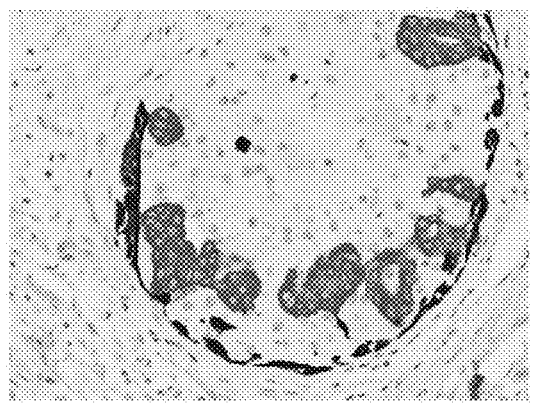
FIG. 92 shows the color version of FIG. 42 of an example of an antibody cocktail of p40 [BC28]+CK5/14+CK7/18 staining a specimen of breast tissue, perhaps abnormal tissue, or perhaps even breast cancer. Staining of p40 (brown) is nuclear. Staining of CK5/14 (brown) is cytoplasmic. Staining of CK7/18 (red) is cytoplasmic.

Results of IHC Staining with p40 [BC28], CK5/14, and P504S: Using the above double-stain protocol, FFPE tissues may be stained with a cocktail of p40 [BC28], CK5/14 (e.g. a combination of anti-CK5 clone [XM26] and anti-CK14 clone [LL002]), and P504S (perhaps also known as AMACR, e.g. rabbit monoclonal anti-AMACR [13H4] or a rabbit polyclonal antibody). An example of staining of prostate tissue is shown in FIGS. 41 and 91. The presence of p40 and or CK5/14 antibodies may result in brown staining. The presence of P504S antibodies may result in red staining.

The tissue may contain normal prostate glands, areas of prostate cancer, or perhaps prostatic intraepithelial neoplasia (PIN). The examples in FIGS. 40, 90, 41, and 91 are representative of instances where cytokeratin markers may be interchangeable. In these examples, HMWCK and CK5/14 are both effective cytokeratin markers and may be considered effectively equivalent.

Figure 43:
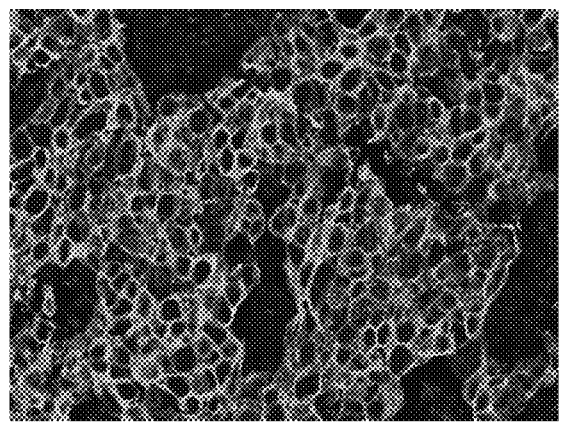
FIG. 43 shows a black and white version of an example of an antibody cocktail of p40 [BC28]+CK5/14+CK7/18 staining a specimen of breast tissue, perhaps abnormal tissue, or perhaps even breast cancer. Staining of p40 (brown) is nuclear and perhaps reduced, or absent, in this sample. Staining of CK5/14 (brown) and CK7/18 (red) is cytoplasmic and membranous. The staining pattern observed is perhaps bimodal staining.
Figure 93:
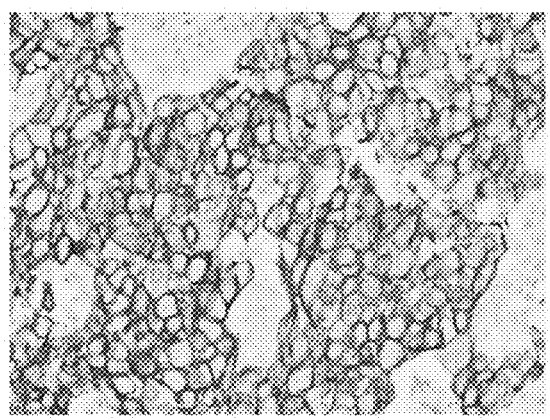
FIG. 93 shows the color version of FIG. 43 of an example of an antibody cocktail of p40 [BC28]+CK5/14+CK7/18 staining a specimen of breast tissue, perhaps abnormal tissue, or perhaps even breast cancer. Staining of p40 (brown) is nuclear and perhaps reduced, or absent, in this sample. Staining of CK5/14 (brown) and CK7/18 (red) is cytoplasmic and membranous. The staining pattern observed is perhaps bimodal staining.

Results of IHC Staining with p40 [BC28], CK5/14, and CK7/18: Using the above double-stain protocol, FFPE tissues may be stained with a cocktail of p40 [BC28], CK5/14 (e.g. a combination of anti-CK5 clone [XM26] and anti-CK14 clone [LL002]), and CK7/18 (e.g. a combination of rabbit monoclonal anti-CK7 antibody [BC1] and rabbit monoclonal anti-CK18 antibody clone [E431-1]). An example of staining of breast tissue, perhaps breast cancer, is shown in FIGS. 42, 92, 43, and 93. The presence of p40 and or CK5/14 antibodies may result in brown staining. The presence of CK7/18 antibodies may result in red staining. FIGS. 43 and 93 may be an example of bimodal staining. The antibody cocktail of p63+CK5/14+CK7/18 may have been shown to be useful in clinical diagnosis. (e.g., see article, "Atypical ductal hyperplasia: interobserver and intraobserver variability." Jain R K, Mehta R, Dimitrov R, Larsson L G, Musto P M, Hodges K B, Ulbright T M, Hattab E M, Agaram N, Idrees M T, Badve S. Mod Pathol. 2011 July; 24(7):917-23, hereby incorporated by reference herein.) An antibody cocktail that uses p40 in place of p63 (e.g. p40 [BC28]+CK5/14+CK7/18) may be similarly useful for diagnosis, perhaps even offering the advantages of p40 [BC28].

Results of IHC Staining with p40 [BC28], CK5/14, and CK8/18: Using the above double-stain protocol, FFPE tissues may be stained with a cocktail of p40 [BC28], CK5/14 (e.g. a combination of anti-CK5 clone [XM26] and anti-CK14 clone [LL002]), and CK8/18 (e.g. a combination of rabbit monoclonal anti-CK8 antibody [EP17] and rabbit monoclonal anti-CK18 antibody clone [E431-1]). An example of staining of breast tissue, perhaps breast cancer, is shown in FIGS. 44 and 94. The presence of p40 and or CK5/14 antibodies may result in brown staining. The presence of CK8/18 antibodies may result in red staining.

Results of IHC Staining with p40 [BC28], Uroplakin II and Uroplakin III: Using the above single-stain protocol, FFPE tissues may be stained with a cocktail of p40 [BC28], Uroplakin II [BC21] and Uroplakin III [BC17]. An example of staining of bladder tissue, perhaps urothelial carcinoma, is shown in FIGS. 45 and 95. The presence of p40, Uroplakin II, and/or Uroplakin III antibodies may result in brown staining. The example of FIGS. 45 and 95 is an instance where a single-color stain, perhaps using goat anti-mouse HRP, is useful because p40, Uroplakin II or Uroplakin III all are indicative of urothelial carcinoma.

Results of IHC Staining with p40 [BC28], Uroplakin II, Uroplakin III, and GATA-3: Using the above double-stain protocol, FFPE tissues may be stained with a cocktail of p40 [BC28], Uroplakin II [BC21], Uroplakin III [BC17], and GATA-3 (e.g. rabbit anti-GATA-3 antibody). An example of staining of bladder tissue, perhaps urothelial carcinoma, is shown in FIGS. 46 and 96. The presence of p40, Uroplakin II, and/or Uroplakin III antibodies may result in brown staining. The presence of GATA-3 may result in red staining.

Results of IHC Staining with p40 (M) and CK5 (M): Using the above single-stain protocol, FFPE tissues may be stained with a cocktail of p40 [BC28] and CK5 (M) (e.g., mouse monoclonal [XM26]). An example of staining of lung SCC is shown in FIGS. 47 and 97. The presence of p40 and/or CK5 antibodies may result in the brown staining.

In many embodiments, antibodies that bind cytokeratin markers may be used in different combinations, and in some cases, interchangeably, as known to those skilled in the art. For example, CK5 may perhaps be interchangeable with CK5/6 or CK5/14. Similarly, HMWCK (high molecular weight cytokeratin) may be used interchangeably with CK5/6 or CK5/14. In another example, CK7 may be used interchangeably with CK8.

Other embodiments may include primary antibody cocktails comprised of p40 [BC28] with other combinations of antibodies, including variations on the example cocktails. In some embodiments, other host species may be used. Embodiments that lack one or more of the antibodies included in the listed examples may also be useful.

In some embodiments, anti-p40 antibodies other than BC28 may also be useful. Rabbit polyclonal or rabbit monoclonal anti-p40 antibodies may be used in some embodiments. In other embodiments, a mouse monoclonal anti-p40 antibody clone other than BC28 may be similarly useful, and perhaps interchangeable with BC28.

In many cases, but perhaps particularly in cases of lung cancer, diagnosis may often be performed on limited tissue samples from cytology or a biopsy, and it may be important to conserve tissue for further molecular testing; therefore, an efficient approach to diagnosis that consumes minimal tissue, but provides optimal specificity and/or sensitivity may be preferred. A method that provides useful diagnostic information, while consuming minimal tissue from the specimen, perhaps by the application of multiple antibodies to the same ample, perhaps through use of an antibody cocktail, or by the sequential application of antibodies, or conceivably by the feature of improved sensitivity or specificity, may be used.

An anti-p40 antibody such as a mouse monoclonal anti-p40 antibody BC28 may be specific for detection of p40 and may be useful in immunohistochemical procedures for diagnosis of several types of cancers in human tissue samples. In particular, anti-p40 antibody such as BC28 has advantages over RP anti-p40 antibody and anti-p63 antibody [4A4], including but not limited to greater specificity and cleaner staining, including the absence of staining of some cases of lung adenocarcinoma, as well as perhaps a lack of staining of macrophages.

Determination of p40 levels may be a useful prognostic factor and indicator of patient outcomes. Loss of p40 expression, as determined by IHC, has been associated with aggressive bladder cancer and shown to be predictive of patient survival (see Matsumoto K et. al. *Urology*, 2008; 72:444-449, and Ohtsuka Y et. al. *BJU Int*, 2006; 97:1322-1326, hereby incorporated by reference herein). As such, the various systems and methods as discussed herein may provide a detection system such as but not limited to detection of cancer, diagnose or even prognose cancer, predict an outcome of cancer, assess efficacy of treatment of cancer, predict recurrence of cancer, or the like. As mentioned herein, use of an antibody or fragment thereof may be performed on an automated staining device. Detection may be made automatically, manually, by image analysis, or the like. Detection may utilize a method including but not limited to immunohistochemistry (IHC), IHC of FFPE, IHC of frozen-tissue sections, immunocytochemistry, ELISA, or the like.

Figure 50:
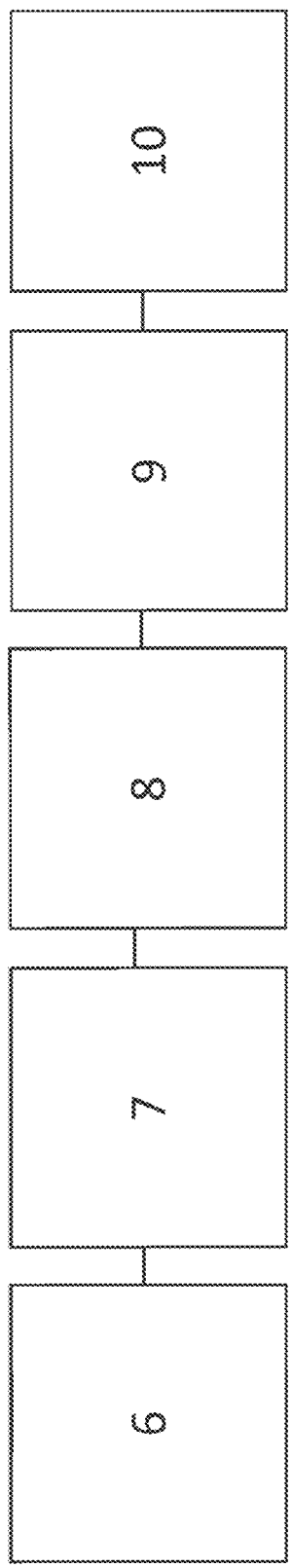
FIG. 50 shows an example of a schematic summary of an immunoassay method in accordance with various embodiments of the present invention.

As but one example of an immunoassay method, embodiments of the present invention may provide obtaining tissue from an animal or human to be tested (6), fixing or freezing said tissue (7), treating said fixed or frozen tissue to unmask epitopes to p40 (8), contacting said treated tissue with an antibody or fragment thereof as discussed herein in an amount and under conditions such that an antibody or fragment thereof binds to a p40 protein if the protein is present in said tissue (9); and perhaps even detecting the presences of said bound antibodies (10), as schematically represented in FIG. 50.

Figure 49:
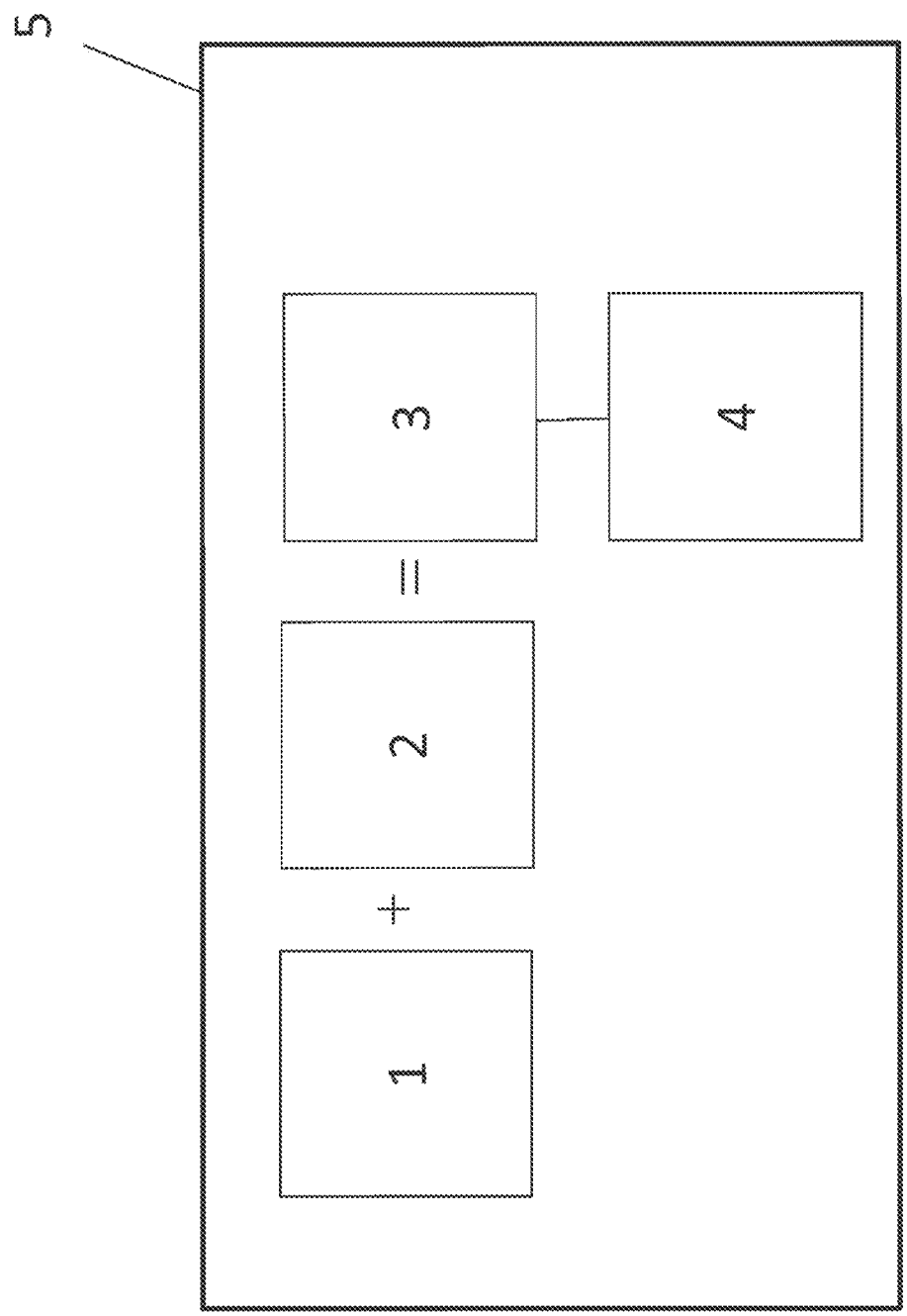
FIG. 49 shows an example of a schematic summary of a kit in accordance with various embodiments of the present invention.

FIG. 49 shows a schematic summary of various embodiments of the present invention including a kit (5) which may provide an antibody, fragment thereof, portion thereof, in a composition or even in a cocktail, perhaps even provided from a hybridoma, the antibody (1) or the like may be contacted with a biological sample (2) to form at least one antibody-antigen complex (3) which may then be detected with a detector (4).

The present invention may provide, in embodiments, a diagnostic or even prognostic test kit which may include an antibody or fragment thereof (as discussed herein) with an antibody detection element of the antibody or fragment thereof perhaps when bound to an antigen. This may provide a method of contacting a biological sample with an antibody or fragment thereof and even detecting binding of, or even the presence of the antibody or fragment thereof bound to a protein or with an antigen in the biological sample perhaps using an antibody detection element. Embodiments may provide an immunoassay method for detecting p40 protein in a mammal or human perhaps by obtaining a tissue from an animal or a human to be tested, contacting the tissue with an antibody or fragment thereof in accordance with the various embodiments presented herein perhaps in an amount and under conditions such that the antibody or fragment thereof may bind to a p40 protein if the protein is present in the tissue; and even detecting the presence of bound antibodies. A biological sample may include but is not limited to blood, urine, urothelial tissue, transitional cell tissue, bladder tissue, normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue, breast tissue, or the like perhaps depending on the antibody or even cocktail being used.

It is noted that of the numerous applications and methods that use anti-p63 antibodies currently known to those in the art, the anti-p63 antibody may be replaced with an anti-p40 antibody (e.g. BC28), perhaps with equivalent, or even perhaps superior, results.

It is noted that use of terms such as p40, p40 antibody, BC28, or the like may relate to anti-p40 antibodies or the like as appropriate as one skilled in the art would understand.

As can be easily understood from the foregoing, the basic concepts of the present invention may be embodied in a variety of ways. It involves both antibody techniques as well as devices to accomplish the appropriate antibody. In this application, the antibody techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detection" or "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

| I. U.S. PATENT DOCUMENTS | | | |
|---|---|---|---|
| Patent Number | Kind Code | Issue Date | Name of Patentee or Applicant of cited Document |
| 7,468,425 | B2 | 2008 Dec. 23 | Sidransky, et al. |
| 6,946,256 | B1 | 2005 Sep. 20 | McKeon, et al. |

| II. NON-PATENT LITERATURE DOCUMENTS |
|---|
| Jain, r., et al.; Atypical ductal hyperplasia: interobserver and intraobserver variability, Modern Pathology (2011) 24, 917-923 |
| Tacha, d., et al.; An Innunohistochemical Analysis of a Newly Developed, Mouse Monoclonal p40 (BC28) in Lung, Bladder, Skin, Breast, Prostate, and Head and Neck Cancers; 2014 College of American Pathologists, pg 1-7, posted February 2014 |
| Khoury M. P. et al. p53 Isoforms: An Intracellular Microprocessor? Genes Cancer. 2011 April; 2(4): 453-65 |
| Murray-Zmijewski F. et al. p53/p63/p73 isoforms: an orchestra of isoforms to harmonise cell differentiation and response to stress, Cell Death Differ. 2006 June; 13(6): 962-72 |
| Kaghad M. et al. Monoallelically expressed gene related to p53 at 1p36, a region frequently deleted in neuroblastoma and other human cancers, Cell. 1997 Aug. 22; 90(4): 809-19 |
| Trink B. et al. A new human p53 homologue, Nat Med. 1998 July; 4(7): 747-8 |
| Osada M. et al. Cloning and functional analysis of human p51, which structurally and functionally resembles p53, Nat Med. 1998 July; 4(7): 839-43 |
| Yang A. et al. p63, a p53 homolog at 3q27-29, encodes multiple products with transactivating, death-inducing, and dominant-negative activities, Mol Cell. 1998 September; 2(3): 305-16 |
| Senoo M. et al. A second p53-related protein, p73L, with high homology to p73, Biochem Biophys Res Commun. 1998 Jul. 30; 248(3): 603-7 |
| Hibi K. et al. AIS is an oncogene amplified in squamous cell carcinoma, Proc Natl Acad Sci USA. 2000 May 9; 97(10): 5462-7 |
| Nobre A. R. et al. p40: A p63 Isoform Useful for Lung Cancer Diagnosis - A Review of the Physiological and Pathological Role of p63, Acta Cytol. 2013; 57(1): 1-8 |
| Bishop J. A. et al. p40 (ΔNp63) is superior to p63 for the diagnosis of pulmonary squamous cell carcinoma, Mod Pathol. 2012 March; 25(3): 405-15 |
| Nonaka D. A study of ΔNp63 expression in lung non-small cell carcinomas, Am J Surg Pathol. 2012 June; 36(6): 895-9 |
| Pelosi G, et al. ΔNp63 (p40) and thyroid transcription factor-1 immunoreactivity on small biopsies or cellblocks for typing non-small cell lung cancer: a novel two-hit, sparing-material approach, J Thorac Oncol. 2012 February; 7(2): 281-90 |
| Brown A. F. et al. Tissue-Preserving Antibody Cocktails to Differentiate Primary Squamous Cell Carcinoma, Adenocarcinoma, and Small Cell Carcinoma of Lung, Arch Pathol Lab Med. 2013 Jan. 4 |
| Karni-Schmidt O. et al. Distinct expression profiles of p63 variants during urothelial development and bladder cancer progression, Am J Pathol. 2011 March; 178(3): 1350-60 |
| Signoretti S. et al. p63 is a prostate basal cell marker and is required for prostate development, Am J Pathol. 2000 December; 157(6): 1769-75 |
| Nylander K. et al. Differential expression of p63 isoforms in normal tissues and neoplastic cells, J Pathol. 2002 December; 198(4): 417-27 |
| Barbareschi M, et al. p63, a p53 homologue, is a selective nuclear marker of myoepithelial cells of the human breast, Am J Surg Pathol. 2001 August; 25(8): 1054-60 |
| U.S. Provisional Pat. application No. 61/770,956, Filed Feb. 28, 2013, entitled "Systems and Methods for Anti-p40 Antibodies", |
| PCT patent application no. PCT/US2013/076203, filed Dec. 18, 2013, entitled "Antibody Cocktail Systems and Methods for Classification of Histologic Subtypes in Lung Cancer" |
| PCT patent application no. PCT/US2013/062043, filed Sep. 26, 2013, entitled "Anti-Uroplakin II Antibodies Systems and Methods" |

Thus, the applicant(s) should be understood to have support to claim and make a statement of invention to at least: i) each of the antibody devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. Each claim may be amended to include "or any other claim" and such amendment will be fully supported by the original application. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention and the incorporated claims can "depend on any other claim", and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An isolated antibody produced by the hybridoma deposited with the American Type Culture Collection (ATCC) under ATCC Patent Deposit Designation No. PTA-120163 or isolated antigen binding fragment of the isolated antibody, wherein the antibody or antigen binding fragment thereof specifically binds p40 comprising SEQ ID NO:4.

2. A composition comprising the isolated antibody or isolated antigen binding fragment thereof of claim 1 and at least one additional isolated antibody or isolated antigen binding fragment thereof, wherein the at least one additional isolated antibody or isolated antigen binding fragment thereof specifically binds to an antigen selected from the group consisting of DSG-3, CK4, CK5, Napsin A, HMWCK, p504S, CK5/14, CK7/18, CK8/18, Uroplakin II, Uroplakin III and GATA-3.

3. The isolated antibody or isolated antigen binding fragment thereof of claim 1, wherein the isolated antibodies or isolated antigen binding fragments thereof comprises a light chain variable region comprising the amino acid sequence encoded by a nucleic acid sequence consisting of SEQ ID NO: 2 and a heavy chain variable region comprising the amino acid sequence encoded by a nucleic acid sequence consisting of SEQ ID NO: 1.

4. The composition according to claim 2 wherein the isolated antigen binding fragment and the at least one additional isolated antibody or isolated antigen binding fragment of the isolated antigen binding fragment are derived from at least two different species.

5. The composition according to claim 4 wherein said at least two different species is selected from a group consisting of mouse, rabbit, goat, horse, chicken and human.

6. The composition according to claim 2 wherein the isolated antibody or isolated antigen binding fragment thereof and the at least one additional isolated antibodies or isolated antigen binding fragments thereof each bind specifically to proteins selected from a group consisting of:
p40 and DSG-3 and CK5 and Napsin A;
p40 and DSG-3 and CK5;
p40 and Napsin A;
p40 and HMWCK and p504s;
p40 and p504s and CK5/14;
p40 and CK5/14 and CK7/18;
p40 and CK5/14 and CK8/18;
p40 and Uroplakin II and Uroplakin III; and
p40 and Uroplakin II and Uroplakin III and GATA-3.

7. The composition according to claim 2 wherein the isolated antibody or the isolated antigen binding fragment thereof and said at least one additional isolated antibodies or isolated antigen binding fragments thereof each bind specifically to proteins selected from a group consisting of:
p40 and DSG-3 and Napsin A;
p40 and DSG-3; and
p40 and CK5.

8. A kit comprising:
the isolated antibody or isolated antigen binding fragment thereof of claim 1; and
an antibody detection reagent of said isolated antibody or isolated antigen binding fragment thereof of claim 1 when bound to the p40 antigen.

9. The isolated antibody or isolated antigen binding fragment thereof of claim 1, wherein the isolated antibody or isolated antigen is conjugated with a label.

10. The antibody according to claim 9 wherein said label is selected from a group consisting of a radioactive element, magnetic particles, radioisotope, fluorescent dye, enzyme, toxin, signal, stain, detection enzymes, horseradish peroxidase (HRP), alkaline phosphatase (AP), beta-galactosidase, chromogens, Fast Red, 3,3'-diaminobenzidine, 3-amino-9-ethylcarbazole, 5-bromo-4-chloro-3-indolyl phosphate, 3,3', 5,5'-tetramethylbenzidine, 5-bromo-4-chloro-3-indolyl-β-D-glucuronide, and any combination thereof.

11. A method for detecting p40 in a biological sample comprising the steps of:
(a) providing the kit of claim 8; and
(a) detecting binding of said isolated antibody or said isolated antigen binding fragment thereof with the p40 antigen with an immunoassay comprising:
(i) contacting the biological sample with the isolated antibody or isolated antigen binding fragment thereof produced by the hybridoma deposited with the American Type Culture Collection (ATCC) under ATCC Patent Deposit Designation No. PTA-120163, wherein the antibody or antigen fragment thereof specifically binds p40 comprising SEQ ID NO:4 to form a complex; and
(ii) detecting the complex with the antibody detecting element provided in the kit, wherein the immunoassay is selected from the group consisting of immunohistochemistry (IHC), IHC of FFPE, IHC of frozen-tissue sections, immunocytochemistry, and ELISA.

12. The method for detecting p40 in a biological sample according to claim 11 wherein said biological sample comprises lung tissue, bladder tissue, breast tissue, and prostate tissue.

13. The method for detecting p40 in a biological sample according to claim 11 wherein said biological sample is selected from a group consisting of a normal tissue, neoplastic tissue, bladder tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue and breast tissue.

* * * * *

SEQUENCE LISTING

<160> NUMBER OF SEQ ID NOS: 5

<210> SEQ ID NO 1
<211> LENGTH: 348
<212> TYPE: DNA
<213> ORGANISM: Mus musculus

<400> SEQUENCE: 1

```
ggagtgaagc tggtggagtc tgggggaggc tttgtgaagc tggagggtc cctgacactc        60
tcctgtgctg cctctggatt cactttcagt atctatgcca tgtcttgggt tcgccagact      120
ccagagaaga ggctggagtg ggtcacatcc attagtagtg gtgatgacat cttctatcca      180
gacaatttga agggccaatt caccatctcc agagataatg ccaggaacat cctgtacctg      240
caaatgagca gtctgaggtc tgaggacacg gccatatatt actgtgtaag acatggttac      300
aatgctacgg actactgggg tcaaggaacc tcagtcaccg tctcctca                    348
```

<210> SEQ ID NO 2
<211> LENGTH: 337
<212> TYPE: DNA
<213> ORGANISM: Mus musculus

<400> SEQUENCE: 2

```
gatgttttga tgacccaaac tccactctcc ctgcctgtca gtcttggaga tcaagcctcc       60
atctcttgca gatctagtca gagcattgta tatagtaatg gaaacaccta tttagaatgg      120
tacctgcaga aaccaggcca gtctccaaaa ctcctgatct acaaagtttc caatcgattt      180
tctggggtcc cagacaggtt cagtggcagt ggatcaggga cagatttcac actcaagatc      240
agcagagtgg aggctgagga tctgggagtt tattactgct ttcaaggttc acatgttcct      300
ttcacgttcg gctcggggac aaagttggaa ataaaac                                337
```

<210> SEQ ID NO 3
<211> LENGTH: 17
<212> TYPE: PRT
<213> ORGANISM: Homo sapiens

<400> SEQUENCE: 3

Met Leu Tyr Leu Glu Asn Asn Ala Gln Thr Gln Phe Ser Glu Pro Gln
1               5                   10                  15

Tyr

<210> SEQ ID NO 4
<211> LENGTH: 9
<212> TYPE: PRT
<213> ORGANISM: Homo sapiens

<400> SEQUENCE: 4

Met Leu Tyr Leu Glu Asn Asn Ala Gln
1               5

<210> SEQ ID NO 5
<211> LENGTH: 13
<212> TYPE: PRT
<213> ORGANISM: Homo sapiens

<400> SEQUENCE: 5

Glu Asn Asn Ala Gln Thr Gln Phe Ser Glu Pro Gln Tyr
1               5                   10